(12) United States Patent
Aszodi et al.

(10) Patent No.: US 8,148,540 B2
(45) Date of Patent: Apr. 3, 2012

(54) HETEROCYCLIC COMPOUNDS, THEIR PREPARATION AND THEIR USE AS MEDICAMENTS, IN PARTICULAR AS ANTI-BACTERIAL AGENTS

(75) Inventors: Joseph Aszodi, Tuscon, AZ (US); Maxime Lampilas, St. Cloud (FR); Branislav Musicki, Paris (FR); David Alan Rowlands, Poissy (GB); Pascal Colette, Le Canet (FR)

(73) Assignee: AstraZeneca, Södertälje (SE)

( * ) Notice: Subject to any disclaimer, the term of this patent is extended or adjusted under 35 U.S.C. 154(b) by 1011 days.

(21) Appl. No.: 11/810,981

(22) Filed: Jun. 7, 2007

(65) Prior Publication Data

US 2007/0299108 A1   Dec. 27, 2007

Related U.S. Application Data

(62) Division of application No. 10/480,019, filed as application No. PCT/FR02/01877 on Jun. 4, 2002, now Pat. No. 7,288,549.

(30) Foreign Application Priority Data

Jun. 8, 2001   (FR) ...................... 01 07520

(51) Int. Cl.
  *C07D 513/00*   (2006.01)
  *C07D 513/02*   (2006.01)
  *C07D 223/16*   (2006.01)
(52) U.S. Cl. .................. 548/153; 546/114; 540/593
(58) Field of Classification Search .................. 546/114; 540/593; 548/153
  See application file for complete search history.

(56) References Cited

U.S. PATENT DOCUMENTS

| 3,629,265 | A | 12/1971 | Grethe |
| 3,654,282 | A | 4/1972 | Fourneau et al. |
| 7,288,549 | B2 * | 10/2007 | Aszodi et al. ................. 514/292 |

FOREIGN PATENT DOCUMENTS

| EP | 0 702 004 A2 | 9/1995 |
| WO | WO 90/15058 | 12/1990 |
| WO | WO 95/09175 | 4/1995 |
| WO | WO 95/18129 | 7/1995 |
| WO | WO 96/29327 | 9/1996 |
| WO | WO 97/23484 | 7/1997 |
| WO | WO 99/01434 | 1/1999 |
| WO | WO 99/16442 | 4/1999 |
| WO | WO 99/52875 | 10/1999 |
| WO | WO 00/12507 | 3/2000 |
| WO | WO 00/37458 | 6/2000 |
| WO | WO 01/25228 A1 | 4/2001 |
| WO | WO 02/051231 A1 | 7/2002 |

OTHER PUBLICATIONS

XP-001181463, Hanna P. E et al, Journal of Medicinal Chemistry, vol. 17, No. 9, pp. 1020-1023, 1974.
XP-002224122, Bishan Zhou, Organic Letters, 43-46, 2002.
XP-002224127, Nagasaka Tatsuo et al, Chemical Abstracts Service, Database Caplus (online), Dec. 21, 1993.
XP-002224128, Moon M. W et al, Chemical Abstracts Service, Database Caplus (online), Drug design and Discovery, 9(3-4), 313-22, 1993.

* cited by examiner

*Primary Examiner* — Nizal Chandrakumar

(57) ABSTRACT

The invention relates to new heterocyclic compounds of general formula (I), and their salts with a base or an acid:

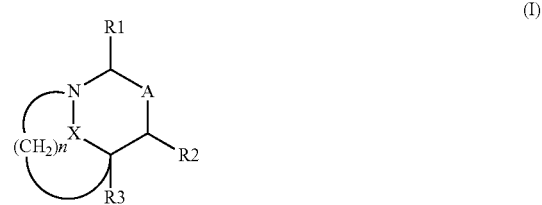

The invention also relates to a process for the preparation of these compounds as well as their use as medicaments, in particular as anti-bacterial agents.

4 Claims, No Drawings

HETEROCYCLIC COMPOUNDS, THEIR PREPARATION AND THEIR USE AS MEDICAMENTS, IN PARTICULAR AS ANTI-BACTERIAL AGENTS

This application is a division of U.S. patent application Ser. No. 10/480,019 filed Dec. 5, 2003, now U.S. Pat. No. 7,288,549 which is a 371 of PCT/FR02/01877 filed Jun. 4, 2002.

The invention relates to new heterocyclic compounds, their preparation and their use as medicaments, in particular as anti-bacterial agents.

In the journal J. Org. Chem., Vol. 37, No. 5, 1972, pages 697 to 699 the preparation of a bicyclic derivative with molecular formula $C_{10}H_{18}N_2O$ is in particular described.

In the journal J. Org. Chem., Vol. 45, No. 26, 1980, pages 5325-5326 the preparation of bicyclic derivatives with molecular formulae $C_6H_9NO_2$ and $C_7H_{11}NO_2$ is in particular described.

In the journal Chemical Reviews, 1983, vol. 83, No. 5, pages 549 to 555 the preparation of bicyclic derivatives with molecular formulae $C_{10}H_{18}N_2O$ and $C_7H_{12}N_2O$ is in particular described.

In the journal Angew. Chem. Int. Ed. 2000, 39, n° 3, pages 625 to 628 the preparation of a compound with molecular formula $C_{12}H_{12}N_2O$ is in particular described.

No particular use of these compounds in the therapeutic field has been described in these documents.

A subject of invention is the compounds corresponding to the following formula (I):

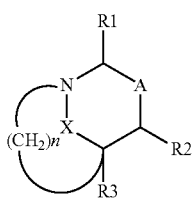

in which:

$R_1$ represents a hydrogen atom, a COOH, CN, COOR, $CONR_6, R_7, (CH_2), R_5$ or

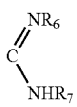

radical,

R is chosen from the group constituted by an alkyl radical containing from 1 to 6 carbon atoms, optionally substituted by a pyridyl or carbamoyl radical, a —$CH_2$-alkenyl containing a total of 3 to 9 carbon atoms, aryl containing from 6 to 10 carbon atoms or aralkyl radical containing from 7 to 11 carbon atoms, the ring of the aryl or aralkyl radical being optionally substituted by an OH, $NH_2$, $NO_2$, alkyl containing from 1 to 6 carbon atoms, alkoxy radical containing from 1 to 6 carbon atoms or by one or more halogen atoms, $R_6$ and $R_7$ being identical or different are chosen from the group constituted by a hydrogen atom, an alkyl containing from 1 to 6 carbon atoms, aryl containing from 6 to 10 carbon atoms and aralkyl radical containing from 7 to 11 carbon atoms, optionally substituted by a carbamoyl, ureido or dimethylamino radical, and an alkyl radical containing from 1 to 6 carbon atoms substituted by a pyridyl radical, n' is equal to 1 or 2 and $R_5$ is chosen from the group constituted by a COOH, CN, OH, $NH_2$, CO—$NR_6R_7$, COOR, OR, OCOH, OCOR, OCOOR, OCONHR, $OCONH_2$, NHR, NHCOH, NHCOR, $NHSO_2R$, NH—COOR, NH—CO—NHR ou $NHCONH_2$, R, $R_6$ and $R_7$ being as defined above;

$R_2$ represents a hydrogen atom or a $(CH_2)_{n'_1}R_5$ group, $n'_1$ being equal to 0, 1 or 2, and $R_5$ being as defined above;

$R_3$ represents a hydrogen atom or an alkyl radical containing from 1 to 6 carbon atoms;

A represents a bond between the two carbon carriers of $R_1$ and $R_2$ or a

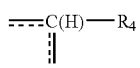

group, $R_4$ representing a hydrogen atom or a $(CH_2)_{n'_1}R_5$ group, n', and $R_5$ being as defined above, the dotted line representing an optional bond with one or other of the carbon carriers of the substituents $R_1$ and $R_2$;

n is equal to 1 or 2;

X represents a divalent —C(O)—B— group attached to the nitrogen atom by the carbon atom, B represents a divalent —O—$(CH_2)_{n''}$— group attached to the carbonyl by the oxygen atom, an —$NR_8$—$(CH_2)_{n''}$— or —$NR_8$—O— group attached to the carbonyl by the nitrogen atom, n" is equal to 0 or 1 and $R_8$ is chosen from the group constituted by a hydrogen atom, an OH, R, OR, Y, OY, $Y_1$, $OY_1$, $Y_2$, $OY_2$, $Y_3$, $OCH_2CH_2SO_mR$, $OSiR_aR_bR_c$ and $SiR_aR_bR_c$ radical, $R_a$, $R_b$ and $R_c$ individually representing a linear or branched alkyl radical containing from 1 to 6 carbon atoms or an aryl radical containing from 6 to 10 carbon atoms, R being as defined above and m being equal to 0, 1 or 2;

Y is chosen from the group constituted by the COH, COR, COOR, $CONH_2$, CONHR, CONHOH, $CONHSO_2R$, $CH_2COOH$, $CH_2COOR$, $CH_2CONHOH$, $CH_2CONHCN$, $CH_2$ tetrazole, protected $CH_2$ tetrazole, $CH_2SO_3H$, $CH_2SO_2R$, $CH_2PO(OR)_2$, $CH_2PO(OR)(OH)$, $CH_2PO(R)(OH)$ and $CH_2PO(OH)_2$ radicals, $Y_1$ is chosen from the group constituted by the $SO_2R$, $SO_2NHCOH$, $SO_2NHCOR$, $SO_2NHCOOR$, $SO_2NHCONHR$, $SO_2NHCONH_2$ and $SO_3H$ radicals, $Y_2$ is chosen from the group constituted by the $PO(OH)_2$, $PO(OR)_2$, PO(OH)(OR) and PO(OH)(R) radicals, $Y_3$ is chosen from the group constituted by the tetrazole radicals, tetrazole substituted by the R radical, squarate, NH or NR tetrazole, NH or NR tetrazole substituted by the R radical, $NHSO_2R$ and $NRSO_2R$, R being as defined above; it being understood that when n is equal to 1 and A represents a

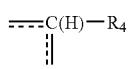

group in which $R_4$ is a hydrogen atom and either X represents the —C(O)—O—$(CH_2)_{n''}$ group in which n" is 0 or 1, or X represents the —CO—$NR_8$—$(CH_2)_{n''}$ group in which n" is 1 and $R_8$ is the isopropyl group, or X represents the —CO—$NR_8$—$(CH_2)_{n''}$ group in which n" is 0 and $R_8$ is hydrogen or phenyl, All three of $R_1$, $R_2$ and $R_3$ cannot represent a hydrogen atom at the same time.

A subject of the invention is also the salts of these compounds which can be obtained with bases or organic or inorganic acids, together with the internal salts in which form certain compounds may, under certain conditions, be present.

The asymmetrical carbon atoms contained in the compounds of formula (I) can independently from one other have the R, S or RS configuration, and a subject of the invention is also therefore, the compounds of formula (I) presented in the form of pure enantiomers or pure diastereoisomers or in the form of a mixture of enantiomers in particular racemates, or diastereoisomer mixtures.

A result of the latter is that the substituents $R_1$, $R_2$, and $R_4$ taken individually on one hand and X on the other hand can be in cis and/or trans position in relation to the ring on which they are fixed and that a subject of the invention is therefore the compounds of formula (I) presented in the form of cis isomers or trans isomers or of mixtures.

By alkyl radical containing from 1 to 6 carbon atoms, is meant a methyl, ethyl, propyl, isopropyl, as well as linear or branched butyl, pentyl or hexyl radical.

By —$CH_2$-alkenyl radical containing from 3 to 9 carbon atoms, is meant for example an allyl radical, or a butenyl, pentenyl or hexenyl radical.

By aryl radical containing from 6 to 10 carbon atoms, is meant a phenyl or naphthyl radical.

By aralkyl radical containing from 7 to 11 carbon atoms, is meant a benzyl, phenethyl or methylnaphthyl radical.

By alkyloxy radical containing from 1 to 6 carbon atoms, is meant in particular a methoxy, ethoxy, propoxy, isopropoxy, as well as butoxy, isobutoxy, sec-butoxy or tert-butoxy radical.

By halogen atom, is meant a fluorine, chlorine, bromine or iodine atom.

By radical squarate, is understood the radical of formula:

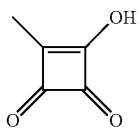

Among the acid salts of the products of formula (I), those formed with inorganic acids, such as hydrochloric, hydrobromic, hydriodic, sulphuric or phosphoric acids or with organic acids such as formic, acetic, trifluoroacetic, propionic, benzoic, maleic, fumaric, succinic, tartaric, citric, oxalic, glyoxylic, aspartic, alkanesulphonic, such as methane and ethane sulphonic, arylsulphonic acids, such as benzene and paratoluenesulphonic acid can be mentioned amongst others.

Among the base salts of the products of formula (I), those formed with inorganic bases such as, for example, sodium, potassium, lithium, calcium, magnesium or ammonium hydroxide or with organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine, or also phosphonium salts, such as the alkyl-phosphoniums, aryl-phosphoniums, alkyl-aryl-phosphoniums, alkenyl-aryl-phosphoniums or quaternary ammonium salts such as tetra-n-butyl-ammonium salt can be mentioned amongst others.

Among the compounds of formula (I), a particular subject of the invention are those in which n is equal to 1 as well as those in which A represents a

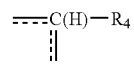

group as defined above, and in particular among these, those in which $R_4$ represents a hydrogen atom.

Among the compounds of formula (I), a particular subject of the invention is also those in which X represents a —CO—B divalent group in which B represents an —$NR_8$—$(CH_2)_{n''}$— group as defined above and more particularly, among these, those in which $R_8$ is a $Y_1$ or $OY_1$ group, in which $Y_1$ is as defined above.

Among the compounds of formula (I), a quite particular subject of the invention is the compounds with the following names:

trans-7-oxo-6-(sulphooxy)-1,6-diazabicyclo[3,2,1]octane-2-carboxamide and its base salts, in particular sodium, trans-7-oxo-N-(phenylmethyl)-6-(sulphooxy)-1,6-diazabicyclo[3,2,1]octane-2-carboxamide and its base salts, in particular sodium, trans-7-oxo-N-(4-pyridinyl methyl)-6-(sulphooxy)-1,6-diazabicyclo[3,2,1]octane-2-carboxamide and its base salts, in particular sodium, trans-7-oxo-N-(3-pyridinyl methyl)-6-(sulphooxy)-1,6-diazabicyclo[3,2,1]octane-2-carboxamide and its base salts, in particular sodium, trans-7-oxo-N-(2-amino 2-oxo ethyl)-6-(sulphooxy)-1,6-diazabicyclo[3,2,1]octane-2-carboxamide and its base salts, in particular sodium, phenylmethyl trans-7-oxo-6-(sulphooxy)-1,6-diazabicyclo[3,2,1] octane-2-carboxylate.

Another subject of the invention is also a process allowing the preparation of the compounds of formula (I).

This process is characterized in that it comprises:

a) a stage during which a compound of formula (II) is reacted with a carbonylation agent, if appropriate in the presence of a base:

(II)

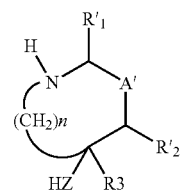

in which:

$R'_1$ represents a hydrogen atom or a CN, protected COOH COOR', $(CH_2)n'R'_5$, $CONR_6$, $R_7$ or protected

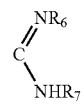

radical;

$R_6$ and $R_7$ being as above defined and R' and $R'_5$ having the definitions of R and $R_5$ above respectively, in which the reactive functions optionally present are protected;

R'$_2$ represents a hydrogen atom or a (CH$_2$)n'$_1$R'$_5$ group, n'$_1$ and R'$_5$ being as defined above;

R$_3$ is as defined previously;

A' represents a bond between the two carbon carriers of R'$_1$ and R'$_2$ or a

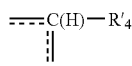

group, R'$_4$ representing a hydrogen atom or a (CH$_2$)n'$_1$R'$_5$ group, n'$_1$ and R'$_5$ being as defined above, the dotted line representing an optional bond with one or other of the carbon carriers of substituents R'$_1$ and R'$_2$;

n is as defined previously;

HZ represents an HO—(CH$_2$)n''—, HNR'$_8$—(CH$_2$)$_{n''}$— or HNR'$_8$—O— group, n'' being as defined previously and R'$_8$ representing a hydrogen atom, protected OH, an R', OR' radical, a Y' or OY' radical, Y' being chosen from COH, COR', COOR', CONH$_2$, CONHR', protected CONHOH, CONHSO$_2$R', protected CH$_2$COOH, CH$_2$COOR', protected CH$_2$CONHOH, CH$_2$CONHCN, CH$_2$ tetrazole groups substituted by R', CH$_2$SO$_2$R', CH$_2$PO(OR')$_2$, protected CH$_2$SO$_3$, protected CH$_2$PO(OR')OH, protected CH$_2$PO(R')OH, protected CH$_2$PO(OH)$_2$, a Y'$_1$ or OY'$_1$ radical, Y'$_1$ being chosen from the SO$_2$R', SO$_2$NHCOH, SO$_2$NHCOR', SO$_2$NHCOOR', SO$_2$NHCONH$_2$, SO$_2$NHCONHR' and protected SO$_3$H groups, a Y'$_2$ or OY'$_2$ radical, Y'$_2$ representing a protected PO(OH)$_2$, protected PO(OH) (OR'), protected PO(OH)(R') or PO(OR')$_2$ group, or a Y'$_3$ radical, Y'$_3$ being chosen from the protected tetrazole, tetrazole substituted by the R' radical, NH or NR' protected tetrazole, NH or NR' tetrazole substituted by the R' radical, NHSO$_2$R' and NR'SO$_2$R groups, R' being as defined above;

with a view to obtaining an intermediate compound of formula:

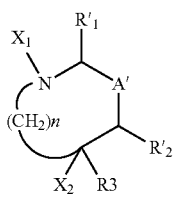

(III)

in which:

R'$_1$, R'$_2$, R$_3$, A' and n have the same meanings as above and either X$_1$ is a hydrogen atom and X$_2$ represents a —Z—CO—X$_3$ group, X$_3$ representing the remainder of the carbonylation agent, or X$_2$ is a —ZH group and X$_1$ represents a CO—X$_3$ group, X$_3$ being as defined previously;

b) a stage during which the intermediate obtained previously is cyclized, in the presence of a base;

and in that:

c) if appropriate, stage a) is preceded and/or stage b) is followed by one or more of the following reactions, in an appropriate order:

protection of the reactive functions,
deprotection of the reactive functions,
esterification,
saponification,
sulphation,
phosphation
amidation,
acylation,
sulphonylation;
alkylation;
introduction of a double bond;
formation of a urea group;
introduction of a tetrazole group;
reduction of carboxylic acids;
dehydration of amide to nitrile;
salification;
ion exchange;
resolution or separation of diasterisomers;
sulphide oxidation to sulphoxide and/or sulphone.

As carbonylation agent, a reagent such as phosgene, diphosgene, triphosgene, an aryl chloroformate such as phenyl chloroformate or p-nitrophenyl chlorformate, an aralkyle chloroformate such as benzyl chloroformate, an alkyl chloroformate such as methyl chloroformate, an alkenyl chloroformate such as allyl chloroformate, an alkyl dicarbonate such as tert-butyl dicarbonate, carbonyl-diimidazole and their mixtures can be used.

The reaction preferably takes place in the presence of a base or a mixture of bases which neutralise the acid formed. It can in particular be an amine such as triethylamine, diisopropylethylamine, pyridine, or dimethylaminopyridine. However, the reaction can also be carried out using the starting product of formula II as a base. An excess is thus used. An example is given in the experimental part.

If appropriate, the product of formula II is used in the form of an acid salt, for example a hydrochloride or a trifluoroacetate.

As a base in stage b), amines, or also hydrides, alcoholates, amides or carbonates of alkali or alkaline-earth metals can also be used.

The amines can be chosen for example from the list above.

As hydride, sodium or potassium hydride can in particular be used.

As an alkali metal alcoholate, potassium t-butylate is preferably used.

As an alkali metal amide, lithium bis(trimethylsilyl) amide can in particular be used.

As carbonate, sodium or potassium carbonate or bicarbonate can in particular be used.

If appropriate, the intermediate of formula III can be obtained in the form of an acid salt generated during the carbonylation reaction and in particular a hydrochloride. It is then used in the cyclization reaction in this form.

Optionally, cyclization can be carried out without isolation of the intermediate of formula III.

The reactions mentioned in stage c) are in general standard reactions, well known to a person skilled in the art.

The reactive functions which are suitable, optionally, for protecting are the carboxylic acid, amine, amide, hydroxy and hydroxylamine functions.

Protection of the acid function is in particular carried out in the form of alkyl esters, allyl, benzyl, benzhydryl or p-nitrobenzyl esters.

Deprotection is carried out by saponification, acid hydrolysis, hydrogenolysis, or also cleavage using soluble compounds of Palladium O.

Examples of these protections and deprotections are provided hereafter in the experimental part.

Protection of the amines and amides is in particular carried out in the form of benzylated derivatives, in the form of carbamates, in particular allyl, benzyl, phenyl or tertbutyl, or also in the form of silylated derivatives such as tertbutyl dimethyl, trimethyl, triphenyl or also diphenyl tertbutyl-silyl derivatives.

Deprotection is carried out, depending on the nature of the protective group, by sodium or lithium in liquid ammonia, by hydrogenolysis or using soluble compounds of Palladium O, by the action of an acid, or by the action of tetrabutylammonium fluoride.

Examples are provided hereafter in the experimental part.

Protection of the hydroxylamines is carried out in particular in the form of benzyl or allyl ethers.

Cleavage of the ethers is carried out by hydrogenolysis or using soluble compounds of Palladium O.

An illustration is provided hereafter in the experimental part.

Protection of the alcohols is carried out in a standard manner, in the form of ethers, esters or carbonates. The ethers can be alkyl or alkoxyalkyl ethers, preferably methyl or methoxyethoxymethyl ethers, aryl or preferably aralkyl ethers, for example benzyl, or silylated ethers, for example the silylated derivatives mentioned above. The esters can be any cleavable ester known to a person skilled in the art and preferably acetate, propionate or benzoate or p-nitrobenzoate. The carbonates can for example be methyl, tertbutyl, allyl, benzyl or p-nitrobenzyl carbonates.

Deprotection is carried out by means known to a person skilled in the art, in particular saponification, hydrogenolysis, cleavage by soluble compounds of Palladium O, hydrolysis in acid medium or also, for the silylated derivatives, treatment by tetrabutylammonium fluoride.

Examples are provided in the experimental part.

The sulphation reaction is carried out by the action of $SO_3$-amine complexes such as $SO_3$-pyridine or $SO_3$-dimethylformamide, by operating in pyridine, the salt formed, for example the pyridine salt, can then be exchanged for example by a salt of another amine, of a quaternary ammonium or of an alkali metal. Examples are provided in the experimental part.

The phosphation reaction is carried out for example by the action of a chlorophosphate such as dimethyl, dibenzyl or diphenyl chlorophosphate.

The amidation reaction is carried out from the start with carboxylic acid using an activation agent such as alkyl chloroformate or EDCI, by the action of ammonium hydroxide or of an appropriate amine or of their acid salts. Examples are provided hereafter in the experimental part.

The acylation and sulphonylation reactions are carried out on the hydroxyureas by the action of an appropriate halide or carboxylic acid anhydride or of an appropriate sulphonic acid halide respectively. Several examples are provided hereafter in the experimental part.

The alkylation reaction is carried out by the action of an alkyl or substituted alkyl halide on the hydroxylated derivatives, in particular by a free or esterified carboxy radical. Illustrations are provided hereafter in the experimental part.

The optional final introduction of a double bond, which is then preferably situated between the carbon atoms carrying $R_4$ and $R_1$, is carried out by the action of a halogenated derivative of selenium then oxidation, according to methods known to a person skilled in the art. An example appears hereafter in the experimental part.

The formation of a urea group, which relates to the substituent $R_8$ is preferably carried out by the action of an appropriate isocyanate on the free NH. An example appears hereafter in the experimental part.

The introduction of a tetrazole group is carried out by the action of a halogenated derivative, preferably fluorinated, of the protected tetrazole. Deprotection can be carried out by hydrogenolysis.

The reduction of acids to alcohols can be carried out by the action of a borane or via an intermediate mixed anhydride, by the action of an alkaline borohydride. The mixed anhydride is prepared for example using an alkyl chloroformate. An example is provided in the experimental part.

The dehydration of amide to nitrile can take place under carbonylation and cyclization reaction conditions.

Oxidation of sulphides to sulphoxides and/or sulphones can be carried out by means of a peracid such as metachloroperbenzoic acid or perphtalic acid or of any other appropriate reagent known by those skilled in the art.

Salification by acids is optionally carried out by the addition of an acid in soluble phase to the compound. Salification by bases can concern either the compounds comprising an acid function, in particular a carboxy function, or those comprising a sulphooxy function or phosphoric acid derivative or those comprising a heterocycle having an acid character. In the first case, the operation is carried out by adding an appropriate base such as those mentioned previously. In the second case, the pyridinium salt is directly obtained during the action of the $SO_3$-pyridine compound and the other salts are obtained from this pyridinium salt. In either case, it can also be carried out by ion exchange on resin. Examples of salification appear hereafter in the experimental part.

Separation of enantiomers and diasterisomers can be carried out according to techniques known to a person skilled in the art, in particular chromatography.

As well as via the processes described previously, the compounds of formula (I) can of course be obtained by methods which use at the start a compound of formula (II) in which $R'_1$, A', $R'_2$, $R_3$ and HZ have the values which lead directly (without conversion) to those of the compounds that need to be prepared. If appropriate, those with these values which will contain reactive functions such as those mentioned above are then protected, deprotection occurring following cyclization stage b or at any other appropriate moment in the synthesis. Protection and deprotection is then carried out as described above.

Such methods are provided hereafter in the experimental part.

The products of general formula (I) have a very good antibiotic activity on gram(+)bacteria such as staphylococci. Their effectiveness on gram (−) bacteria, in particular on coliform bacteria is particularly notable.

These properties render said products as well as their acid salts and pharmaceutically acceptable bases suitable for use as medicaments in the treatment of germ sensitive infections, in particular staphylococcia, such as staphylococcal septicemias, malignant staphylococcia of the face or skin, pyoderma, septic or suppurative wounds, anthrax, phlegmons, erysipelas, acute, primative or post-influenzal staphylococcia, broncho-pneumonia, pulmonary suppurations.

These products can also be used as medicaments in the treatment of colibacilloses and related infections, in proteus, klebsiella and salmonella infections and in other conditions caused by gram (−) bacteria.

A subject of the present invention is therefore also, as medicaments and in particular antibiotic medicaments, the products of formula (I) as defined above as well as their salts with pharmaceutically acceptable acids and bases.

A more particular subject of the invention is, as medicaments, the products of formula (I) as described above in which n is equal to 1 as well as those in which A represents a

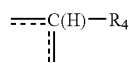

group as defined above, and in particular those in which $R_4$ is a hydrogen atom.

A quite particular subject of the invention is, as medicaments, the products of formula (I) in which X represents a divalent —CO—B group in which B represents an —$NR_8$—($CH_2$)n''— group as defined above and more particularly, among these, those in which $R_8$ represents a $Y_1$ or $OY_1$ group, in which $Y_1$ is as defined above.

Among the compounds of formula (I), a quite particular subject of the invention is, as medicaments, the compounds with the following names:

trans-7-oxo-6-(sulphooxy)-1,6-diazabicyclo[3,2,1]octane-2-carboxamide and its base salts, in particular sodium, trans-7-oxo-N-(phenylmethyl)-6-(sulphooxy)-1,6-diazabicyclo[3,2,1]octane-2-carboxamide and its base salts, in particular sodium, trans-7-oxo-N-(4-pyridinyl methyl)-6-(sulphooxy)-1,6-diazabicyclo[3,2,1]octane-2-carboxamide and its base salts, in particular sodium, trans-7-oxo-N-(3-pyridinyl methyl)-6-(sulphooxy)-1,6-diazabicyclo[3,2,1]octane-2-carboxamide and its base salts, in particular sodium, trans-7-oxo-N-(2-amino 2-oxo ethyl)-6-(sulphooxy)-1,6-diazabicyclo[3,2,1]octane-2-carboxamide and its base salts, in particular sodium, phenylmethyl trans-7-oxo-6-(sulphooxy)-1,6-diazabicyclo [3,2,1]octane-2-carboxylate.

A subject of the invention is also the pharmaceutical compositions containing at least one of the compounds according to the invention as defined above as active ingredient.

These compositions can be administered by buccal, rectal, parenteral, in particular intramuscular route, or by local route in a topical application on the skin and the mucous membranes.

The compositions according to the invention can be solids or liquids and be presented in pharmaceutical forms commonly used in human medicine such as for example, plain or sugar-coated tablets, gelatin capsules, granules, suppositories, injectable preparations, ointments, creams, gels; they are prepared according to usual methods. The active ingredient(s) can be incorporated with the excipients usually used in these pharmaceutical compositions, such as talc, gum arabic, lactose, starch, magnesium stearate, cocoa butter, aqueous or non aqueous vehicles, fatty matter of animal or vegetable origin, paraffin derivatives, glycols, various wetting, dispersing or emulsifying agents, preservatives.

These compositions can in particular be presented in the form of a powder intended to be dissolved extemporaneously in an appropriate vehicle, for example, apyrogenic sterile water.

The administered dose varies according to the illness treated, the patient in question, the administration route and the product considered. It can be, for example, between 0.250 g and 10 g per day, by oral route in man, with the product described in Example 1 or also between 0.25 g and 10 g per day by intramuscular or intravenous route.

The products of formula (I) can also be used as disinfectants for surgical instruments.

Finally, a subject of the invention is the products of formulae (III), as defined previously as well as their salts with acids and in particular their hydrochlorides, as new industrial products and in particular as intermediate products necessary for the preparation of the products of formula (I).

The products of formula (II) are known or can be prepared according to methods known to a person skilled in the art. References to the literature as well as preparations are provided hereafter in the experimental part.

The following examples illustrate the invention, without however limiting its scope.

EXAMPLES

In the examples which follow the following abbreviations have been used:
DEAD: diethyl azodicarboxylate
TEA: triethylamine
DMAP: 4-dimethylamino-pyridine
EDCI: 1-(3-dimethylamino-propyl)-3-ethylcarbo-diimide hydrochloride
THF: tetrahydrofuran
AIBN: 2,2'-azo-bis-isobutyronitril
M: molecular molar weight
MS: mass spectrometry
EI: electronic impact
SIMS: secondary ion mass spectrometry
FAB: fast atom bombardment Example 1 diphenylmethyl cis-7-oxo-6-oxa-1-azabicyclo[3,2,1]octane-4-propanoate 3.16 g (10.6 mmoles) of the hydrochloride of 3-oxo-1-(phenylmethyl)-4-piperidinepropanoic acid (M=297.7 g) (described in the Japanese Patent Application J54098-772) is mixed with 100 ml of ethanol and cooled down to 10° C. Under a stream of nitrogen, 1.84 g of $NaBH_4$ is added over 15 minutes, whilst maintaining the temperature between 8 and 13° C. The temperature is left to rise to ambient temperature and the reaction medium is left in contact for 1 hour 30 minutes. Another 380 mg of $NaBH_4$ is added and the reaction medium is left to react overnight at ambient temperature.

The solvent is evaporated off under reduced pressure, the residue is taken up in 50 ml of water and the pH is adjusted from 10 to 2 using concentrated hydrochloric acid. The reaction medium is evaporated again under reduced pressure. The solid residue (approximately 10.8 g) is washed twice with 100 ml of ethanol then the solvent is evaporated off under reduced pressure.

3.10 g of the hydrochloride of 3-hydroxy-1-(phenylmethyl)-4-piperidinepropanoic acid (M=299.7 g) is thus obtained, which corresponds to a yield of 97%.

The 3.10 g (10.3 mmoles) of the compound obtained previously, is diluted with 100 ml of ethanol then added to 900 mg of Pd/C at 10% by prehydrogenated weight and in 30 ml of ethanol.

The reaction medium is left under a hydrogen atmosphere at normal pressure overnight, then the catalyst is eliminated by filtration and the ethanol is eliminated by evaporation under reduced pressure.

1.90 g of the hydrochloride of trans-3-hydroxy-4-piperidinepropanoic acid (M=209.6 g) is obtained i.e. a yield of 88%.

1.79 g (8.54 mmoles) of the compound obtained previously is mixed with 20 ml of ethanol and 20 ml of water.

Then concentrated soda is added until the pH is approximately 8.5.

Then, 1 ml of allyl chloroformate and concentrated soda are added so as to keep the pH between 8 and 9.

The reaction mixture is extracted with ethyl acetate w then the aqueous phase is acidified to pH 2 by the addition of concentrated hydrochloric acid and re-extracted with ethyl acetate. After drying and evaporation of the solvent under reduced pressure, 1.69 g of crude product is obtained which is taken up in a mixture of dichloromethane and ethanol, then the solvent is filtered and again evaporated under reduced pressure.

1.40 g of trans-3-hydroxy-1-[(2-propenyloxy) carbonyl]-4-piperidinepropanoic acid (M=257 g), i.e. a yield of 60% is thus obtained.

3.24 g (12.6 mmoles) of the hydroxy-acid above and 6.4 g of triphenylphosphine are dissolved in 60 ml of THF at 0° C. under a nitrogen atmosphere. 2.5 ml of DEAD is then added and after 15 minutes the reaction mixture is evaporated under reduced pressure in order to obtain 12 g of crude product. The reaction medium is purified by chromatography on silica by progressively eluting with a mixture of dichloromethane and ethyl acetate 9/1, 8/2, 7/3 to separate the cis and trans lactones.

2.72 g of cis lactone in a mixture with reduced DEAD and phosphine oxide is thus obtained.

This product is again placed in solution in 10 ml of DME and 8 ml of a 1N NaOH solution is added. After 1 hour of contact, the reaction mixture is extracted twice with ethyl acetate, then acidified to pH 2 with 2N HCl, and re-extracted with ethyl acetate. After drying and evaporating the solvent under reduced pressure, 1.07 g of hydroxy-acid is obtained.

1.0 g of crude hydroxy-acid is dissolved in a mixture of 5 ml of dichloromethane and 2 ml of methanol, then treated with an excess of diphenyldiazomethane in dichloromethane, until the starting product disappears. The solvent is evaporated off under reduced pressure and the product is purified by chromatography in order to produce 1.39 g of diphenylmethyl cis-3-hydroxy-1-[(2-propenyloxy)carbonyl]-4-piperidinepropanoate (M=423 g), i.e. an overall yield of 26%.

1.2 g (2.83 mmoles) of the product obtained previously is then dissolved under a nitrogen atmosphere in 23 ml of dichloromethane. Then 390 μl of acetic acid then 860 μl of $Bu_3SnH$ and 70 mg of $Pd(PPh_3)_4$ are added.

The solvent is evaporated off under reduced pressure in order to obtain 3.82 g of crude product which is washed with petroleum ether. 1.27 g of product is obtained which is filtered on silica with dichloromethane, then with a 95/5 then 90/10 mixture of dichloromethane and methanol. 0.87 g of diphenylmethyl cis-3-hydroxy-4-piperidinepropanoate (M=339 g) is thus obtained, i.e. a yield of 77%.

400 mg (1.00 mmole) of the compound obtained previously is dissolved in 25 ml of dichloromethane, 80 μl of diphosgene ($Cl_3COCOCl$), 336 μl of TEA, 144 mg of DMAP are added.

The reaction medium is left to react at ambient temperature for five hours 30 minutes, then diluted with dichloromethane, followed by washing with an aqueous solution of tartaric acid at 10%, then with a solution of sodium phosphate buffer at pH 7, the organic phase is dried over sodium sulphate, then the solvent is evaporated off under reduced pressure. 380 mg of crude product is thus obtained.

Purification is carried out by chromatography on silica, eluting with a dichloromethane/ethyl acetate mixture 95/5 with 0.1% water.

184 mg of the compound of the title (M=365.43 g), i.e. a yield of 50% is obtained.

NMR Spectrum of the Proton

In $CDCl_3$, at 300 MHz, chemical shifts of the peaks in ppm and multiplicity:

1.60 to 1.88 (m): $NCH_2$—$CH_2$—CH; 2.48 (m): $CH_2$—C$H_2$—CO; 2.78 (d)—$\overline{2.90}$ ($\overline{m}$)—$\overline{3.33}$ to 3.47 (m): C$\overline{H_2}$—N—$CH_2$; 4.50 (d): CHO—$CH_2$; 6.89 (s): $CO_2C$ $\overline{H}(C_6H_5)_2$; $\overline{7.33}$ (m): $(C_6H_5)_2$.

IR ($CHCl_3$): 1784, 1734, 1600, 1585, 1496 cm$^{-1}$

MS(positive electrospray) m/z: $[M]^+=365$

Example 1a

Cis-7-oxo-6-oxa-1-azabicyclo[3,2,1]octane-4-propanoic acid 176 mg (0.482 mmoles) of the product obtained previously is dissolved in 10 ml of acetone. 90 mg of Pd/C is added at 10% by weight.

The reaction medium is left to react under a hydrogen atmosphere at normal pressure for 3 hours. 25 mg of catalyst are also added and the reaction is left to continue for 1 hour 15 minutes.

The catalyst is filtered out then the solvent is evaporated off under reduced pressure in order to obtain 146 mg of product.

The product is reacted in 10 ml of acetone with 35 mg of Pd/C at 10% by weight under a hydrogen atmosphere and the reaction is left to complete for 1 hour.

The catalyst is then separated out by filtration and the filtrate is evaporated under reduced pressure. 137 mg of crude product is obtained which is crystallized from a mixture of ethyl ether and petrol ether. 75 mg of the sought product (M=199 g), is thus obtained i.e. a yield of 78%.

NMR Spectrum of the Proton

In $CDCl_3$, at 250 MHz, chemical shifts of the peaks in ppm and multiplicity:

1.30 to 1.63 (m) and 1.88 (m): $NCH_2$—$CH_2$—CH; 2.25 (t): $CH_2$—$CH_2$—CO; 3.06 (m) and 3.$\overline{38}$ (m): $\overline{CH_2}$—$\overline{N}$—$CH_2$; 4.65 (d): $\overline{C}$—CHO—$CH_2$; 12.08 (s): Mobile $\overline{H}$.

IR (Nujol): 1785, 1717 cm$^{-1}$

MS (FAB) m/z: $[M+H]^+=200$; 159

Example 2 diphenylmethyl trans-7-oxo-6-oxa-1-azabicyclo[3,2,1]octan-4-acetate 94 mg (0.259 mmoles) of the hydrochloride of diphenylmethyl trans-3-hydroxy-4-piperidine-acetate compound (M=361.87 g) (described in Eur. J. Med. Chem—Chim. Ther—1982-17(6)531-5) and 7 ml of dichloromethane are mixed together under an inert atmosphere.

The reaction medium is cooled down using an ice bath and 19 μl of diphosgene is infected. The reaction medium is agitated for 25 minutes, then 72 μl of TEA is injected. The reaction medium is agitated at ambient temperature for 30 minutes and the solvent is evaporated off under reduced pressure.

The reaction medium is then taken up in 7 ml of toluene.

36 μl of TEA then 31 mg of DMAP are added.

The reaction medium is heated for 15 minutes at 100° C., then left to return to ambient temperature, followed by washing with 2 times 4 ml of tartaric acid at 10% in water, then with 4 ml of water saturated with sodium chloride.

The reaction medium is dried over magnesium sulphate and filtered, the solvent is then evaporated off under reduced pressure.

78 mg of oil is obtained which is chromatographed on silica, with a 95/5 mixture of dichloromethane and ethyl acetate as eluent.

35.7 mg of expected compound (M=351.405 g), in the form of white crystals is thus obtained, i.e. a yield of 39%.

Example 2a

Trans-7-oxo-6-oxa-1-azabicyclo[3,2,1]octan-4-acetic acid 38.7 mg (0.110 mmoles) of the product obtained in Example 2 as well as 2 ml of acetone and 38 mg of Pd/C catalyst at 10% by weight are mixed together under an inert atmosphere.

The reaction medium is placed under a hydrogen atmosphere at normal pressure.

The reaction medium is left to react for 45 minutes, then the catalyst is eliminated by filtration and the solvent is evaporated off under reduced pressure.

32.6 mg of crude product is thus obtained.

Recrystalization is carried out from ethyl ether in order to obtain 14.2 mg of white crystals of the expected compound ($C_8H_{10}NO_4$—M=185.181 g), i.e. a yield of 69%.

Example 3 diphenylmethyl cis-7-oxo-6-oxa-1-azabicyclo [3,2,1]octan-4-acetate 1.5 g (5.78 mmoles) of trans-1-[(1,1-dimethylethoxy)carbonyl]-3-hydroxy-4-piperidineacetic acid (described in Eur. J. Med. Chem—Chim. Ther—1982-17(6)531-5), 7 ml of dichloromethane, 3.03 g of triphenylphosphine and 22 ml of tetrahydrofuran are mixed together.

A solution of 0.91 ml of DEAD in 2.5 ml of tetrahydrofuran is added. The reaction medium is left to react for 3 hours 20 minutes, then 8.7 ml of 1N soda is added and agitation is carried out for 1 hour 15 minutes.

Followed by extracting twice with ethyl acetate, then adjusting to pH 2 with 2N hydrochloric acid, then extracting three times with ethyl acetate.

The organic phases are combined and washed with water saturated with sodium chloride, then dried over magnesium sulphate, filtered and the solvent is evaporated off under reduced pressure.

1.37 g of white crystals of 1,1-dimethylethyl (3a.alpha., 7a.alpha.)-hexahydro-2-oxo-furo[2,3-c]pyridine-6(2H)-carboxylate ($C_{12}H_{21}NO_5$—M=259.304 g) is thus obtained, i.e. a yield of 91%.

1.37 g (5.28 mmoles) of the compound obtained previously and 32 ml of dichloromethane are mixed together under an inert atmosphere.

An excess of a solution of diphenyldiazomethane in dichloromethane is introduced, until the starting product disappears.

The solvent is then evaporated off under reduced pressure and 2.81 g of crude product is thus obtained which is purified by chromatography on silica, using dichloromethane, then a 95/5 dichloromethane/ethyl acetate mixture as eluent.

2.00 g of white crystals of diphenylmethyl cis-1-[(1,1-dimethylethoxy)carbonyl]-3-hydroxy-4-piperidineacetate, (M=425.528 g) is obtained, i.e. a yield of 89%.

0.6 g (1.41 mmoles) of the compound obtained previously and 1.93 ml of a solution of hydrogen chloride in methanol at 7.3 mol/l are introduced, The reaction medium is agitated at ambient temperature and after 15 minutes, 1 ml of dichloromethane is added.

After another 15 minutes, the reaction medium is evaporated under reduced pressure.

Dichloromethane is also added, then the reaction medium is again evaporated. This operation is repeated several times.

The product is then crystallized from ethyl ether.

0.44 g of the hydrochloride of diphenylmethyl cis-3-hydroxy-4-piperidineacetate with molecular formula formula, $C_{20}H_{23}NO_3$, HCl (M=361.871 g) is thus obtained, i.e. a yield of 86%.

This reaction also leads to the formation of variable quantities of (3a.alpha., 7a.alpha.)-hexahydro-furo[2,3-c]pyridin-2(3H)-one lactone hydrochloride, (M=177.6 g).

0.28 g (0.77 mmoles) of the compound $C_{20}H_{23}NO_3$, HCl obtained previously and 19 ml of dichloromethane are mixed together under an inert atmosphere.

60 µl of diphosgene is added at 0° C. and agitation is carried out. After 25 minutes 0.32 ml of TEA is introduced. 94 mg of DMAP is then added and the reaction medium is left to return to ambient temperature.

The reaction medium is agitated for 4 hours 15 minutes, then washed successively with an aqueous solution of tartaric acid at 10% then with water saturated with sodium chloride.

Followed by drying over magnesium sulphate, filtering and the solvent is evaporated off under reduced pressure.

0.265 g of expected compound, with molecular formula C21H21 NO4 (M=351.405 g) is thus obtained i.e. a yield of 98%.

NMR Spectrum of the Proton

In $CDCl_3$, at 250 MHz, chemical shifts of the peaks in ppm and multiplicity:

1.82 (m): $NCH_2$—$CH_2$; 2.30 to 2.70 (m): CO—$CH_2$—CH; 2.93 (d)—2.99 (dt) and $\overline{3}$.45 (m): $CH_2$—N—$CH_2$; 4.60 (d): CH—$\underline{CHO}$—$CH_2$; 6.87 (s): $CO_2\underline{CH}(C_6H_5)_2$; 7.10 to 7.35 (m): $(C_6\overline{H}_5)_2$.

IR ($C\overline{H}Cl_3$)=1786, 1734; 1600, 1587, 1496 cm$^{-1}$.

MS (SIMS)m/z: [M+Na]$^+$374$^+$.

Example 3a cis-7-oxo-6-oxa-1-azabicyclo[3,2,1]octan-4-acetic acid 55 mg (0.156 mmoles) of the product obtained in Example 3, 3 ml of ethyl acetate and 55 mg of Pd/C catalyst at 10% by weight are mixed together.

The reaction medium is placed under a hydrogen atmosphere at normal pressure.

The reaction medium is left to react for 1 hour 30 minutes, then the catalyst is filtered out and the solvent is evaporated off under reduced pressure. 38 mg of crude product is thus obtained which is crystallized from a mixture of pentane and ethyl ether.

In this manner 16 mg of white crystals of expected compound (M=185.181 g) is recovered, i.e. a yield of 55%.

NMR Spectrum of the Proton

In $CDCl_3$, at 250 MHz, chemical shifts of the peaks in ppm and multiplicity:

1.63 to 1.86 (m) and 1.91 (m): $NCH_2$—$CH_2$; 2.27 to 2.49 (m) and 2.54 (dd): CO—$CH_2$—CH; 2.98 (d) and 3.54 (d): C$\underline{H}_2$—N—$CH_2$—$CH_2$; 3.04 (dt) and 3.41 (dd): $CH_2$—N—C$\overline{H}_2$—$CH_2$; 4.71 (d)

$\overline{\text{—}}$CH—$\underline{\text{CHO}}$—$CH_2$—

IR (Nujol): 1784, 1734, 1686 cm$^{-1}$.

MS (SIMS) m/z: [M+H]$^+$=186$^+$, 167$^+$.

Example 3b methyl cis-7-oxo-6-oxa-1-azabicyclo[3,2,1]octan-4-acetate 78 mg (0.421 mmoles) of the compound obtained in Example 3a is then dissolved in 1 ml of dichloromethane.

An excess of diazomethane is added dropwise until a yellow coloration remains, then the solvent is evaporated off under reduced pressure.

80 mg of crude product is thus obtained which is purified by chromatography on silica, eluting with a dichloromethane/ethyl acetate mixture 95/5.

8.2 mg of expected compound (M=199.208 g) is thus obtained i.e. a yield of 10%.

Example 4 cis-7-oxo-6-oxa-1-azabicyclo[3,2,1]octan-4-acetonitrile 67 mg (0.38 mmoles) of (3a.alpha., 7a.alpha.)-hexahydrofuro[2,3-c]pyridin-2(3H)-one hydrochloride (M=177.6 g) prepared in Example 3 is dissolved in 1 ml of an ammonia solution at 4.17 mol/l in methanol.

The reaction medium is agitated for 5 hours, the solvent is evaporated off under reduced pressure, then 1 ml of the ammonia solution in methanol is again added and the reaction is left to continue for 18 hours.

The solvent is evaporated off under reduced pressure and 79 mg of cis-3-hydroxy-4-piperidineacetamide with molecular formula C7H14O2N2 (M=158 g) is thus obtained.

75 mg of the compound obtained above in solution in 9 ml of dichloromethane is mixed under an inert atmosphere.

The reaction medium is cooled by an ice bath and 30 µl of diphosgene is introduced.

The reaction medium is kept at 0-5° C. for 40 minutes, then 0.16 ml of TEA is introduced and 5 minutes afterwards, 46 mg of DMA.

Agitation is carried out for 4 hours at ambient temperature.

The reaction medium is washed twice with 2 ml of tartaric acid at 10% in water, then with 2 ml of a saturated aqueous solution of sodium chloride.

The reaction medium is dried over MgSO4, filtered and the solvent is evaporated off under reduced pressure. 35 mg of crude product is thus obtained that is taken up in a 30/70 mixture of ethyl acetate and dichloromethane. The impurities are filtered out and the filtrate is evaporated under reduced pressure.

23 mg of expected compound (M=166.18 g) is thus obtained in the form of oil, i.e. a yield of approximately 26%.

IR (Nujol): 2241, 1777 cm$^{-1}$
MS (EI) m/z: [M]$^+$=166, 137, 82, 55, 42.

Example 5

3-benzoyl-1,3-diazabicyclo[2,2,1]heptan-2-one 1.01 g (5.43 mmoles) of 1,1-dimethylethyl 3-amino-1-pyrrolidinecarboxylate (M=186.25 g) (described in the Patent Application WO 9801426) and 10 ml of dichloromethane are mixed together under an inert atmosphere, the solution is cooled down to 0° C., then 0.76 ml of TEA is added dropwise.

Agitation is carried out for 15 minutes whilst maintaining the temperature at 0° C., then 0.63 ml of benzoyl chloride is added.

The reaction medium is left to return to ambient temperature, then diluted by adding 10 ml of dichloromethane.

The reaction medium is then washed with an aqueous solution of tartaric acid at 10%, followed by drying over magnesium sulphate, filtering and the dichloromethane is eliminated by evaporation under reduced pressure.

1.30 g of 1,1-dimethylethyl 3-(benzoylamino)-1-pyrrolidinecarboxylate (M=292.36 g) is thus obtained in the form of a yellow oil. The corresponding yield is 82%.

1.30 g (4.46 mmoles) of this compound is mixed with 10 ml of methanol.

The solution is cooled down to 0° C., then 6.12 ml of a solution of hydrogen chloride at 7.3 moles/l in methanol is introduced progressively.

The solvent is then evaporated off under reduced pressure.

1.01 g of N-(3-pyrrolidinyl)-benzamide hydrochloride (M=226.707 g) is thus obtained in the form of brown oil, i.e. a yield close to 100%.

1.01 g (4.46 mmoles) of the compound obtained previously, as well as 10 ml of dichloromethane are mixed together under an inert atmosphere.

The reaction medium is cooled down to 0° C., then 1.36 ml of TEA is added dropwise.

Agitation is carried out for 15 minutes, then 1.44 ml of diphosgene is added dropwise.

The reaction medium is kept at 0° C. for 30 minutes, then left to return to ambient temperature.

The reaction medium is then diluted with dichloromethane, washed with an aqueous solution of tartaric acid at 10%, then with water.

Followed by drying over magnesium sulphate, filtering and concentrating by evaporation of the solvent under reduced pressure in order to obtain 0.615 g of crude, product.

The crude product is purified by chromatography on silica eluting with a 90/10 mixture of dichloromethane/acetone.

In this way 0.320 g of the chloride of 3-(benzoylamino)-1-pyrrolidinecarboxylic acid which crystallizes is recovered. The corresponding yield is 28%.

0.585 g (2.31 mmoles) of the previous compound is then dissolved under an inert atmosphere in 18 ml of tetrahydrofuran.

The solution is cooled down to −78° C., then 2.55 ml of a 1 M solution of lithium bis(trimethylsilyl) amide is added dropwise to tetrahydrofuran.

A yellow solution is obtained which is kept at −78° C. for 20 minutes, then agitation is continued for 1 hour whilst the temperature is allowed to rise. At 0° C. 350 µl of acetic acid, then 5 ml of tartaric acid in solution at 10% in water are added. The reaction medium is diluted with ethyl acetate then washed with a solution of tartaric acid at 10% then with a phosphate buffer solution at pH=7, then with water.

The organic phase is dried over magnesium sulphate, filtered and concentrated by evaporation of the solvent under reduced pressure.

0.315 g of crude product is thus obtained, in the form of a yellow solid.

This crude product is purified by chromatography on silica eluting with a mixture of dichloromethane and ethyl acetate 90/10.

0.140 g of expected compound $C_{12}H_{12}N_2O_2$, (M=216.24 g), in the form of a white solid, i.e. a yield of 28% is in this way recovered.

IR (CHCl$_3$): 1801, 1775, 1675; 1620, 1603, 1582 cm$^{-1}$.
MS (positive electrospray) m/z: [M]$^+$=216, 105, 77.

Example 6

Potassium salt of trans-6-[(phenylmethoxy)carbonyl]-2-oxo-1,3-diazabicyclo[2,2,1]heptan-3-acetic acid 1 g (3.12 mmoles–M=186.25 g) of 1-(1,1-dimethylethyl) and 2-(phenylmethyl) trans-4-amino-1,2-pyrrolidinedicarboxylate (described in J. Org. Chem. 1991, 56, 3009-3016), 10 ml of tetrahydrofuran, 560 µl of allyl bromoacetate and 660 µl of TEA are mixed together.

The reaction medium is left to react under agitation at ambient temperature for 14 hours, then for 3 hours at 50° C.

Followed by diluting with ethyl acetate and washing with an aqueous solution of tartaric acid at 10%, then with a saturated aqueous solution of sodium chloride.

The organic phase is dried over magnesium sulphate, filtered then the solvent is evaporated off under reduced pressure.

1.21 g of crude product is thus obtained which is purified by chromatography on silica, eluting with a mixture of dichloromethane and ethyl acetate 80/20.

0.99 mg of 1-(1,1-dimethylethyl) and 2-(phenyl methyl) trans-4-[[[(2-propenyloxy)carbonyl]methyl]amino]-1,2-pyrrolidine dicarboxylate with molecular formula $C_{12}H_{30}N_2O_6$ (M=418 g) is thus recovered.

6 ml of a 4 M solution of hydrogen chloride in ethyl acetate, is added under a nitrogen atmosphere and at 0° C. to 0.99 g (2.36 mmoles) of the compound obtained previously. The reaction medium is then left to react at ambient temperature for 15 minutes.

The solvent is evaporated off under reduced pressure. A crude product is obtained which is crystallized from ethyl ether in order to obtain 0.95 g phenyl methyl trans-4-[[[(2-propenyloxy)carbonyl]methyl]amino]-2-pyrrolidinecarboxylate dihydrochloride, with molecular formula $C_{17}H_{23}N_2O_4$, 2HCl (M=394 g).

0.5 g of this product is dissolved in 20 ml of dichloromethane and 1.3 ml of 2N soda and 3 ml of water are added. The solution is left to settle, followed by extracting with dichloromethane, drying over magnesium sulphate, then filtering and the solvent is evaporated off under reduced pressure.

339 mg of free diamine is thus obtained. The corresponding yield is 83%.

100 mg (0.314 mmoles) of the diamine obtained previously is dissolved in 5 ml of acetonitrile at 0° C. and under a nitrogen atmosphere.

21 µl of diphosgene is added. After 15 minutes of contact, this solution is added, under a nitrogen atmosphere and over 4 hours, to a mixture containing 38 mg of DMAP and 88 µl of TEA in 10 ml of acetonitrile heated to 70° C.

After the addition is finished, the reaction mixture is again heated for one hour, then cooled down, diluted with ethyl acetate and washed successively with an aqueous solution of tartaric acid at 10%, then with a saturated aqueous solution of sodium chloride. After drying over sodium sulphate, filtration and evaporation of the solvents under reduced pressure, 58 mg of crude product is obtained. This product is purified by chromatography on silica eluting with a dichloramethane/ethyl acetate mixture 8/2 in order to produce 19 mg of 2-propenyl trans-6-[(phenylmethoxy)carbonyl]-2-oxo-1,3-diazabicyclo[2,2,1]heptan-3-acetate with molecular formula $C_{18}H_{20}N_2O_5$ (M=344.57 g), i.e. a yield of 17%.

24 mg (0.069 mmoles) of the previous compound is then dissolved in 250 µl of dichloromethane. 3 mg of Pd(PPh$_3$)$_4$ is introduced under a nitrogen atmosphere, then 150 µl of a 0.5 M solution of potassium ethyl-2-hexanoate in ethyl acetate is added. After several minutes, it forms a precipitate which is centrifuged and washed twice with 500 µl of ethyl acetate.

24 mg of expected compound $C_{15}H_{15}KN_2O_5$ (M=342 g), is obtained i.e. a quantitative yield.

NMR Spectrum of the Proton

In DMSO, at 300 MHz, chemical shifts of the peaks in ppm and multiplicity:

1.83 (ddd) and 2.56: N—CH$_2$—CHN—C$\underline{H}_2$; 2.50 and 2.79 (d):

N—CH2—CHN—CH$_2$; 3.23 (d) and 3.41 (d): =C—N—CH$_2$—C=O; 3.62 (ddd): O=C—CHN—CH$_2$; 4.13 (s): N—CH$_2$—CHN—CH$_2$; 5.16 (s): =C—O—CH$_2$—C$_6$H$_5$; 7.38 (m): C$_6$H$_5$—CH$_2$.

MS (positive electrospray) m/z: [2MK+H]$^+$=723, [2MK+Na]$^+$=707, [MK+K]$^+$=381, [MK+Na]$^+$=365; [MK+H]$^+$=343.

Example 7 methyl trans-3-benzoyl-2-oxo-1,3-diazabicyclo[2,2,1]heptane-6-carboxylate 0.471 g (1.93 mmole) of 1-(1,1-dimethylethyl) and 2-methyl trans-4-amino-1,2-pyrrolidinedicarboxylate (described in J. Org. Chem. 1991, 56, 3009-3016) and 3.5 ml of dry dichloromethane to dissolve it are mixed together under a nitrogen atmosphere.

The solution is cooled down to 0° C., then 269 µl of TEA is added dropwise.

The reaction medium is agitated for 15 minutes whilst maintaining at 0° C., then 224 µl of benzoyl chloride is added dropwise.

The temperature is then left to return to 20° C. over one hour.

The reaction medium is diluted with 30 ml of dichloromethane, then washed with an aqueous solution of tartaric acid at 10%, then a solution saturated with sodium bicarbonate, then with water.

The reaction medium is dried over magnesium sulphate, filtered, and concentrated by evaporation of the dichloromethane under reduced pressure.

0.6 g of a yellow oil is thus obtained which is purified by chromatography on silica using a dichloromethane/methanol mixture 99/1 as eluent.

In this way 0.499 g of 1-(1,1-dimethylethyl) and 2-methyl trans-4-(benzoylamino)-1,2-pyrrolidine dicarboxylate with molecular formula $C_{18}H_{24}N_2O_5$ (M=348 g) is recovered i.e. a yield of 74%.

0.400 g (1.15 mmole) of the compound obtained previously is mixed under a nitrogen atmosphere with 3 ml of ethyl acetate in order to dissolve the compound, then the solution is cooled down to 0° C., 2.89 ml of a solution of 4 mole/l of HCl in ethyl acetate is added.

At the end of 15 minutes, agitation is continued at ambient temperature for 1 hour.

The solvent is then eliminated by evaporation under reduced pressure.

In this way 0.350 g methyl trans-4-(benzoylamino)-2-pyrrolidinecarboxylate hydrochloride with molecular formula $C_{13}H_{15}N_2O_3$, HCl (M=284.744 g) is thus obtained in the form of a beige solid.

0.327 g (1.15 mmole) of the compound obtained previously, placed under a nitrogen atmosphere, is mixed with 4 ml of dichloromethane.

The suspension is then cooled down to 0° C., then 352 µl of TEA is added. The reaction medium is agitated for 15 minutes at 0° C., then 138 μl of diphosgene is added. Agitation is continued for 5 minutes at 0° C., then the reaction mixture is left to return to ambient temperature. It is also left to react for 30 minutes.

The reaction medium is then diluted with dichloromethane and washed with an aqueous solution of tartaric acid at 10%, then with water and dried over magnesium sulphate.

After filtering the solvent is eliminated by evaporation under reduced pressure. 0.360 g of crude product is thus obtained which is purified by chromatography on silica eluting with a dichloromethane/acetone mixture 95/5.

93.7 mg of methyl trans-4-(benzoylamino)-1-(chlorocarbonyl)-2-pyrrolidinecarboxylate hydrochloride ($C_{14}H_{14}N_2O_4$, HCl (M=310.74 g) is thus recovered, i.e. a yield of 26%.

93.7 mg (0.301 mmole) of the compound obtained previously, is mixed under a nitrogen atmosphere with 3 ml of tetrahydrofuran. The temperature of the solution is lowered to −78° C., then 332 μl of lithium bis(trimethylsilyl) amide in 1M solution is added dropwise into tetrahydrofuran and the reaction medium is kept at −78° C. for another 5 minutes.

The reaction medium is agitated for 30 minutes at ambient temperature.

The solution is then cooled down to 0° C., and 55 μl of acetic acid is added. 20 ml of ethyl acetate and 3 ml of a phosphate buffer at pH=7.0 is added. The solution is left to settle, followed by washing with water, drying over magnesium sulphate, filtering and concentrating by evaporation. 76 mg of a foam is thus obtained which is purified by chromatography on silica eluting with a dichloromethane/acetone mixture 97/3.

5 mg of pure expected compound, with molecular formula ($C_{14}H_{14}N_2O_4$, HCl (M=274.279 g), is recovered i.e. a yield of 6%.

IR (CHCl$_3$): 1805, 1779, 1743, 1669; 1603, 1589, 1486 cm$^{-1}$.
MS (EI) m/z: [M]$^+$=274, 215, 169, 105, 77.

Example 7a phenylmethyl trans-3-benzoyl-2-oxo-1,3-diazabicyclo[2,2,1]heptane-6-carboxylate The operation is carried out in a similar way to that indicated in Example 7, starting from 0.92 g of 1-(1,1-dimethylethyl) and 2-phenylmethyl trans-4-amino-1,2-pyrrolidinedicarboxylate (described in J. Org. Chem. 1991, 56, 3009-3016) in order to obtain the expected compound with an overall yield of 5.4% over 4 stages.

Example 8 phenylmethyl trans-2-oxo-3-(phenylsulphonyl)-1,3-diaza bicyclo[2,2,1]heptane-6-carboxylate 2.97 g (9.26 mmoles) of 1-(1,1-dimethylethyl) and 2-(phenylmethyl) trans-4-amino-1,2-pyrrolidinedicarboxylate (described in J. Org. Chem. 1991, 56, 3009-3016) with molecular formula $C_{17}H_{24}N_2O_4$ (M=320.392 g) are mixed together under a nitrogen atmosphere and 25 ml of dichloromethane is added. The reaction medium is cooled down to 5° C. and 1.3 ml of TEA is added. Agitation is carried out for 10 minutes and then 1.63 g of benzenesulphonyl chloride is added.

The reaction medium is left under agitation at 5° C. for 15 minutes, then the temperature of the reaction medium is left to rise to 20° C. for a duration of 45 minutes.

The reaction medium is diluted using dichloromethane, followed by washing with an aqueous solution of tartaric acid at 10%, then with phosphate buffer at pH=7.0, then with a saturated aqueous solution of sodium chloride. The reaction medium is dried over magnesium sulphate and the solvent is evaporated off under reduced pressure.

4.5 g of crude product is thus obtained which is chromatographed on silica eluting with a dichloromethane and ethyl acetate mixture 90/10.

4.06 g of 1-(1,1-dimethylethyl) and 2-(phenyl methyl) trans-4-[(phenylsulphonyl)amino]-1,2-pyrrolidinedicarboxylate with molecular formula $C_{23}H_{28}N_2O_6S$ (M=460, 552 g) is thus recovered, which corresponds to a yield of 95%.

3.83 g (8.31 mmoles) of the sulphonamide obtained previously is mixed with 10 ml of anhydrous methanol.

The solution is cooled down to 0° C. and 8.2 ml of a solution of 10 mol/l of hydrochloric acid in methanol is added at this temperature.

The solution is agitated at 0° C. for 5 minutes, then the temperature is left to rise to ambient temperature.

After 30 minutes, the methanol is evaporated off under reduced pressure, the reaction medium is taken up several times in methanol then in dichloromethane. The hydrochloride is then crystallized from ethyl ether.

In this way 3.2 g of phenylmethyl trans-4-[phenylsulphonyl) amino]-2-pyrrolidinecarboxylate hydro-chloride, with molecular formula $C_{18}H_{20}N_2O_4S$, HCl (M=396.896 g) is thus obtained, which corresponds to a yield of 96%.

2.78 g (7 mmoles) of the hydrochloride obtained previously is mixed under an inert atmosphere with 28 ml of dichloromethane.

The reaction medium is then cooled down to about 0-5° C., then 2.15 ml of TEA is added.

Agitation is continued for 15 minutes at a temperature comprised between 0 and 5° C., then 0.46 ml of diphosgene is added.

The reaction medium is kept at this temperature for 4 minutes, then a 10% aqueous solution of tartaric acid is added, the reaction medium is diluted using dichloromethane, decanted, washed with a saturated aqueous solution of sodium chloride, dried over magnesium sulphate, and concentrated under reduced pressure.

In this way 3.1 g of a yellow oil is obtained which is purified by chromatography on silica, eluting with a dichloromethane/ethyl acetate mixture 9/1.

1.82 g of phenylmethyl trans-1-(chlorocarbonyl)-4-[(phenylsulphonyl)amino]-2-pyrrolidinecarboxylate, with molecular formula $C_{19}H_{19}ClN_2O_5S$ (M=422.89 g) is recovered, which corresponds to a yield of 61%.

1.81 g (4.28 mmoles) of the carbamoyl chloride obtained previously is mixed under an inert atmosphere with 31 ml of tetrahydrofuran.

The solution obtained is cooled down to −70° C., then 4.7 ml of a 1M solution of lithium bis(trimethylsilyl) amide in tetrahydrofuran is added at this temperature over 10 minutes.

The reaction medium is agitated for 45 minutes at −70° C., then the temperature is left to rise to about 0° C. The reaction medium is kept at this temperature for 2 hours 30 minutes.

Then 295 μl of acetic acid is added.

The reaction medium is diluted with dichloromethane, then washed with a 10% aqueous solution of tartaric acid, with a phosphate buffer solution at pH=7 and with a saturated aqueous solution of sodium chloride.

Followed by drying over magnesium sulphate, and concentrating to dryness under reduced pressure.

The crude product is purified by chromatography on silica, using a dichloromethane/ethyl acetate mixture 95/5 as eluent.

In this way 244 mg of expected compound with molecular formula $C_{19}H_{18}N_2O_5S$ (M=386.429 g) is obtained, which corresponds to a yield of 14%.

NMR Spectrum of the Proton

In $CDCl_3$, at 400 MHz, chemical shifts of the peaks in ppm and multiplicity:

2.15 (m): O=C—CH—$CH_2$; 2.85 (d) and 3.08 (d): O=C—N—$CH_2$; 3.62 (m): $\overline{O}$=C—CH—N—$CH_2$; 4.94 (S): $O_2$S—N—$\overline{C}H$—$CH_2$; 5.16: $CO_2CH_2\overline{C}_6H_5$; 7.34 (m): $C_6H_5$; 7.57 (m)—7.68 (m) and 8.03(m): $\overline{SO}_2C_6H_5$.

IR ($CHCl_3$): 1780, 1743; 1586, 1499 $cm^{-1}$.

MS (positive electrospray) m/z: $[2M+Na]^+$=795; $[M+Na+CH_3CN]^+$=450; $[M+Na]^+$=409; $[M+H]^+$=387.

Example 9 phenylmethyl trans-3-benzoyl-4-methyl-2-oxo-1,3-diaza-bicyclo[2,2,1] heptane-6-carboxylate 18.69 g (58.52 mmoles) of 1-(1,1-dimethyl-ethyl) and of 2-(phenylmethyl) 4-oxo-1,2 pyrrolidinedicarboxylate (described in Chem. Pharm. Bull. 43(8)1302-1306 (1995)) with molecular formula $C_{17}H_{21}NO_5$ (M=319.361 g) and 500 ml of anhydrous ethyl ether are mixed together under an inert atmosphere.

A suspension of 10 g of $CeCl_3$ in 50 ml of anhydrous ethyl ether is added to the solution obtained.

The suspension is agitated for 30 minutes at 20° C., then cooled down to −60° C.

20 ml of a 3M solution of MeMgBr in ethyl ether is then added.

The reaction medium is left to react for 1 hour at −60° C., then the temperature is left to rise to 0° C. over 30 minutes. Neutralization is carried out with a 10% aqueous solution of $NH_4Cl$, followed by extracting with dichloromethane, filtering, the organic phase is washed with water, dried over magnesium sulphate, and concentrated to dryness under reduced pressure.

19.33 g of an oil is thus obtained which is purified by chromatography on silica eluting with a dichloromethane/terbutylmethyl-ether mixture 90/10.

7.21 g of 1-(1,1-dimethylethyl) and 2-(phenylmethyl) cis-4-hydroxy-4-methyl-1,2-pyrrolidinedicarboxylate, with molecular formula $C_{18}H_{25}NO_5$ (M=335.404 g) is obtained i.e. a yield of 36%, as well as 2.5 g of the alcohol epimer.

3.17 g (9.45 mmoles) of the compound obtained previously and 70 ml of dichloromethane are mixed together under an inert atmosphere. The reaction medium is cooled down to 5° C. and 2.3 ml of TEA, then 1.28 ml of methane sulphonyl chloride is added dropwise.

The reaction medium is agitated for 45 minutes at 5° C.

Followed by washing with a 10% aqueous solution of tartaric acid, then with a phosphate buffer solution at pH 7, then with water.

The organic phase is dried over magnesium sulphate and concentrated to dryness under reduced pressure.

3.9 g of an oil is thus obtained which is purified by chromatography on silica eluting with a dichloromethane/ethyl acetate mixture 90/10.

2.75 g of 1-(1,1-dimethylethyl) and 2-(phenyl-methyl) cis-4-methyl-4-[(methylsulphonyl) oxy]-1,2-pyrrolidine dicarboxylate with molecular formula $C_{19}H_{27}NO_7S$ (M=413.494 g) is recovered which corresponds to a yield of 70%.

A solution of 2.54 g (6.14 mmoles) of the mesylate obtained previously in 40 ml of dimethylformamide is prepared.

519 mg (7.98 mmoles) of $NaN_3$ is then added at 20° C., the reaction medium is heated at 50° C. for 2 hours. After cooling down, it is poured into 250 ml of water and extracted with 250 ml of dichloromethane. The organic phase is washed with water, then dried over magnesium sulphate and evaporated to dryness under reduced pressure.

2.4 g of crude product is obtained which is purified by chromatography on silica, with a dichloromethane/ethyl acetate mixture 95/5 as eluent.

1.66 g of 1-(1,1-dimethylethyl) and 2-(phenylmethyl) trans-4-azido-4-methyl-1,2-pyrrolidinedicarboxylate with molecular formula $C_{18}H_{24}N_4O_4$ (M=360.42 g) is thus recovered, (titre approximately 30% by weight) which corresponds to a yield of approximately 25%.

1.85 g of the azide obtained previously (i.e. approximately 1.7 mmole) is dissolved in 18 ml of toluene.

1.38 ml of Bu3SnH and 84 mg of AIBN are then added at 20° C.

The reaction medium is taken to 75° C. and kept at this temperature for 2 hours.

The toluene is evaporated off followed by re-dissolving in ethyl acetate. A saturated aqueous solution of potassium fluoride is agitated for 30 minutes at ambient temperature.

The reaction medium is filtered on clarcel, it is left to settle and the organic phase is dried over magnesium sulphate.

After evaporation of the solvent under reduced pressure, 3 g of an oil is obtained which is chromatographed on silica, eluting with a dichloromethane/methanol mixture 9/1.

560 mg of 1-(1,1-dimethylethyl) and 2-(phenylmethyl) trans-4-amino-4-methyl-1,2-pyrrolidinedicarboxylate with molecular formula $C_{18}H_{26}N_2O_4$ (M=334.419 g) is recovered. The yield is therefore quantitative.

578 mg (1.72 mmoles) of the amine obtained previously is mixed under an inert atmosphere with 30 ml of dichloromethane.

The reaction medium is cooled down to 5° C. and 290 μl of TEA, then 240 μl of benzoyl chloride are added dropwise.

Agitation is continued at 5° C. for 30 minutes.

The reaction medium is diluted with dichloromethane, washed with a 10% aqueous solution of tartaric acid, with a saturated aqueous solution of sodium carbonate, then with water, the organic phase is dried over magnesium sulphate, and the solvent is evaporated off under reduced pressure.

950 mg of an oil is thus obtained which is purified by chromatography eluting with a dichloromethane/ethyl acetate mixture 90/10.

In this way 732 mg of 1-(1,1-dimethylethyl) and 2-(phenylmethyl) trans-4-(benzoylamino)-4-methyl-1,2-pyrrolidinedicarboxylate with molecular formula $C_{25}H_{30}N_2O_5$ (M=438.528 g) is recovered, which corresponds to a yield of 97%.

636 mg (1.45 mmoles) of the amide obtained previously is dissolved in 1.9 ml of ethyl acetate, followed by cooling down to about 0-5° C. with an ice bath, then 3.2 ml of a hydrogen chloride solution at 4.6 mol/l in ethyl acetate is added.

The temperature is left to rise to 20° C., then after 1 hour, the solvent is evaporated off under reduced pressure.

The hydrochloride is then crystallized from ethyl ether.

In this way 570 mg of the hydrochloride of phenylmethyl trans- 4-(benzoylamino)-4-methyl-2-pyrrolidinecarboxylate with molecular formula $C_{20}H_{22}N_2O_3$, HCl (M=374.87 g), in the form of a white powder is recovered. The yield is therefore quantitative.

100 mg (0.267 mmole) of the hydrochloride obtained previously is dissolved under an inert atmosphere in 1.5 ml of dichloromethane.

The reaction medium is cooled down to about 0-5° C., then 90 µl of TEA is added.

The reaction medium is agitated for 15 minutes at 5° C., then 20 µl of diphosgene is added.

Agitation is continued for 30 minutes at 5° C.

Then, the reaction medium is treated with a 10% aqueous solution of tartaric acid, extracted with dichloromethane, the organic phase is washed with a saturated aqueous solution of sodium chloride, dried over magnesium sulphate, and the solvent is evaporated off under reduced pressure.

130 mg of an oil is thus obtained which is purified by chromatography on silica eluting with a dichloromethane/ethyl acetate mixture 9/1.

72 mg of phenylmethyl trans-4-(benzoylamino)-1-(chlorocarbonyl)-4-methyl-2-pyrrolidine-carboxylate with molecular formula $C_{21}H_{21}N_2O_4Cl$ (M=400.865 g) is then recovered, which corresponds to a yield of 67%.

373 mg (0.930 mmole) of the compound obtained previously is dissolved in 9 ml of tetrahydrofuran.

The solution is then cooled down to −70° C. and 1 ml of a 1 M solution in lithium bis(trimethylsilyl) amide tetrahydrofuran is added over 5 minutes.

The reaction medium is left to warm up to 0° C. over 45 minutes, then 69 µl of acetic acid is added.

The reaction medium is then diluted with dichloromethane, washed with a 10% aqueous solution of tartaric acid, then with a phosphate buffer solution at pH=7.0, and with a saturated aqueous solution of sodium chloride.

The organic phase is dried over magnesium sulphate, concentrated to dryness under reduced pressure, in order to obtain 330 mg of a crude product which is purified by chromatography on silica, eluting with a dichloromethane/ethyl acetate mixture 98/2 containing 0.1% TEA by volume.

In this way 123 mg of the expected compound with molecular formula C21H20N2O4 (M=364.404 g) is recovered, which corresponds to a yield of 36%.

NMR Spectrum of the Proton

In $CDCl_3$, at 300 MHz, chemical shifts of the peaks in ppm and multiplicity:

1.76 (s): $CH_3$; 2.11 (dd) and 2.73 (ddd): N—CH—$CH_2$; 2.93 (dt) and $\overline{3.00}$ (d): N—$CH_2$; 3.96 (ddd): N—CH—$C\overline{H}_2$; 5.21: $CO_2CH_2C_6H_5$; 7.36 (m): $CH_2C_6H_5$; 7.43 (t) and 7.57 (tt) and 7.72 (d): $COC_6H_5$.

IR($CHCl_3$) 1776, 1745, 1682; 1601, 1580, 1498 cm$^{-1}$.

MS (positive electrospray) m/z: [2M+Na]$^+$=751; [2M+H]$^+$=729; [M+Na]$^+$=387; [M+H]$^+$=365

Example 10

1-propenyltriphenylphosphonium salt of phenylmethyl trans-2-oxo-3-(sulphooxy)-1,3-diazabicyclo[2,2,1]heptane-6-carboxylate 15 g (46.71 mmoles) of 1-(1,1-dimethylethyl) and 2-(phenylmethyl) cis-4-hydroxy-1,2-pyrrolidinedicarboxylate (commercial product) with molecular formula $C_{17}H_{23}NO_5$ (M=321.377 g) is dissolved under an inert atmosphere in 225 ml of anhydrous dichloromethane.

5.42 ml of 2,6-lutidine is added to the solution. Followed by cooling down to −70° C., then 8.25 ml of trifluoromethanesulphonic anhydride is introduced over 5 minutes.

The reaction medium is agitated for 10 minutes at −70° C. then 4.43 g of O-allyl-hydroxyl-amine is introduced at −70° C.

The reaction mixture is then left at ambient temperature for 27 hours.

The reaction mixture is diluted with dichloromethane, then washed with a 10% aqueous solution of tartaric acid, with a saturated aqueous solution of $NaHCO_3$, and water.

The organic phase is dried over sodium sulphate, and the solvent is evaporated off under reduced pressure.

In this way 23 g of a crude oil is obtained which is purified by chromatography on silica, the eluent being successively a 95/5, 90/10, then 80/20 dichloromethane/ethyl acetate mixture.

7.18 g of 1-(1,1-dimethylethyl) and 2-(phenylmethyl) trans-4-[(2-propenyloxy)amino]-1,2-pyrrolidine-dicarboxylate with molecular formula $C_{20}H_{28}N_2O_5$ (M=376.456 g) is recovered, which corresponds to a yield of 40%.

3.25 g (8.63 mmoles) of the compound obtained previously is dissolved in 3.5 ml of ethyl acetate.

The reaction medium is cooled down to about 0-5° C., then 19 ml of a 4.6 mol/l solution of hydrogen chloride in ethyl acetate is added.

The reaction medium is left to react whilst agitating at about 0-5° C. for 40 minutes.

The solvent is evaporated off under reduced pressure, followed by taking up several times with diethyl ether, whilst extracting the liquid supernatant.

In this way 2.54 g of the hydrochloride is obtained in the form of a white precipitate, which is dissolved in 55 ml of dichloromethane under agitation. 7.3 ml of 2N soda is added. After decantation, the organic phase is dried over sodium sulphate.

The dichloromethane is evaporated off under reduced pressure.

2.12 g of phenylmethyl trans-4-[(2-propenyloxy) amino]-2-pyrrolidinecarboxylate with molecular formula $C_{15}H_{20}N_2O_3$ (M=276.337 g) is thus obtained in the form of an oil i.e. a yield of 89%.

4.14 g (15 mmoles) of the compound obtained previously is dissolved under an inert atmosphere in 1.5 l of acetonitrile.

The reaction medium is cooled down to about 0-5° C. and 1.14 ml of diphosgene is added. Agitation is carried out for 15 minutes whilst being maintained at 0-5° C., then 4.6 ml of TEA, and 1.83 g of DMAP in 80 ml of acetonitrile are added successively.

The temperature is left to rise to ambient temperature and the reaction medium is left to react for 26 hours, then half of the solvent is evaporated off under reduced pressure.

Then, the reaction medium is treated with a 10% aqueous solution of tartaric acid, then extracted with dichloromethane. The organic phase is washed using a saturated aqueous solution of sodium chloride, dried over magnesium sulphate and the solvent is evaporated off under reduced pressure.

43 g of crude product is thus obtained which is purified by chromatography on silica eluting with a dichloromethane/ethyl acetate mixture 90/10 containing 0.1% TEA.

312 mg of phenylmethyl trans-2-oxo-3-(2-propenyloxy)-1,3-diazabicyclo[2,2,1]heptane-6-carboxylate with molecular formula $C_{16}H_{18}N_2O_4$ (M=302.33 g) is recovered which corresponds to a yield of 7%.

70.2 mg (0.232 mmole) of the compound obtained previously is dissolved under an inert atmosphere in 2.3 ml of dichloromethane. 26.5 µl of acetic acid and 134 mg of Pd(P(Ph)$_3$)$_4$ are then introduced.

The reaction medium is left to react for 40 minutes at ambient temperature, then the temperature is lowered to −20° C. and 2.96 ml of a solution of an SO3-pyridine complex at 0.314 mol/l is added. The reaction medium is left to react for 2 hours and 30 minutes then dichloromethane is added and evaporation is carried out under reduced pressure, followed by taking up in 40 ml of dichloromethane and washing with 5 ml of water. The organic phase is separated and dried over sodium sulphate, then the solvent is evaporated off under reduced pressure.

In this way 280 mg of crude product is obtained which is purified by chromatography on silica, eluting successively with a dichloromethane/acetone mixture 80/20 containing 0.1% of TEA, then a dichloromethane/acetone mixture 50/50 containing 0.1% of TEA.

34.0 mg of expected compound, with molecular formula $C_{34}H_{33}N_2O_7SP$ (M=644.689 g) is recovered in the form of a yellow oil, i.e. a yield of 23%.

NMR Spectrum of the Proton

In $CDCl_3$, at 400 MHz, chemical shifts of the peaks in ppm and multiplicity:

2.00(m) and 2.48(m): $CH_2$—CH—C=O; 2.72(d) and 3.12(s): CH—$CH_2$—N; $\overline{3.75}$(m): $CH_2$—CH—C=$O_2$; 4.71(s) CH—$\overline{CH_2}$=N; 5.18 [AB] $CH_2$—$C_6H_5$; 7.35(m): $CH_2$—$\overline{C_6H_5}$ and 2.29(m): $CH_3$—$\overline{CH}$=CH; 6.62 and 7.21 $CH_3$—CH=CH; 7,60-7.85 $\overline{P(C_6H_5)}$3

MS (negative and positive electrospray) m/z:
[Manion]$^-$=341
[Mcation]$^+$=303

Example 11

1-propenyltriphenylphosphonium salt of methyl trans-2-oxo-3-(sulphooxy)-1,3-diazabicyclo[2,2,1]heptane-6-carboxylate The operation is carried out as in Example 10, but starting from 207 mg of 1-(1,1-dimethylethyl) and 2-methyl cis-4-hydroxy-1,2-pyrrolidinedicarboxylate.

12 mg of the desired product of formula $C_7H_{10}N_2O_7S$ (M=266.231 g) is thus obtained.

MS (negative and positive electrospray) m/z:
[Manion]$^-$=265
[Mcation]$^+$=303

Example 12a diphenylmethyl trans-7-oxo-6-oxa-1-azabicyclo[3,2,1]octane-3-carboxylate 8 ml of dichloromethane and 347 mg (1 mmole) of diphenylmethyl cis-5-hydroxy-3-piperidinecarboxylate hydrochloride (described in Acta Chem. Scand. Ser. B 35(4) 289-294) are mixed together under an inert atmosphere.

The reaction medium is cooled down to 0° C., then 346 µTEA and 72 µl of diphosgene are added.

The reaction medium is left to react for 15 minutes whilst maintaining the temperature at 0° C., then the solvent is evaporated off under reduced pressure, followed by taking up in 25 ml of dry toluene and filtering to eliminate the TEA hydrochloride.

553 µl of TEA is added to the filtrate and heating is carried out under reflux for 4 hours.

The reaction medium is then diluted with ethyl acetate and washed with an aqueous solution containing 10% tartaric acid, then with a saturated aqueous solution of sodium chloride, and the organic phase is dried over magnesium sulphate.

Evaporation under reduced pressure is carried out and 339 mg of crude product is recovered which is purified by chromatography on silica, eluting with a toluene/ethyl acetate mixture 70/30.

In this way 146 mg of the expected compound (M=337.378 g) is recovered, which corresponds to a yield of 43%.

NMR Spectrum of the Proton

In $CDCl_3$, at 250 MHz, chemical shifts of the peaks in ppm and multiplicity:

2.15 (ddd) and 2.73 (dq): N—$CH_2$—CHO—$CH_2$; 2.92 (tt) $O_2C$—CH—; 3.00 (d) and 3.4$\overline{5}$ (d): N—$CH_2$—$\overline{C}$HO; 3.48 (dd) an$\overline{d}$ 4.07 (dd): N—$CH_2$—CH—$\overline{CO_2}$; 4.79 (dt): N—$CH_2$—CHO; 6.90 (s) $\overline{CO_2}$—CH—$(C_6H_5)_2$; 7.33 (m): $(C_6H_5)$ 2-IR($\overline{CHCl_3}$): 1792, 1734; 1$\overline{6}$00, 1585, 1497 $cm^{-1}$ MS (EI) m/z: [M]$^+$=337, 292, 183, 167.

Example 12b trans-7-oxo-6-oxa-1-azabicyclo[3,2,1]octane-3-carboxylic acid 320 mg of the compound obtained in Example 12a, 17 ml of acetone and 70 mg of Pd/C catalyst at 20% by weight are mixed together.

Agitation is carried out under a hydrogen atmosphere at normal pressure.

At the end of 2 hours 30 minutes, 70 mg of catalyst is added and left to react for another 1 hour 30 minutes, then the reaction medium is filtered.

The solvent is evaporated off under reduced pressure and 350 mg of crude product is thus obtained which is crystallized from pentane.

Filtering is carried out and 158 mg of the sought product with molecular formula $C_7H_9NO_4$ (M=171.154 g) is thus recovered in the form of a grey solid. The corresponding yield is 89%.

NMR Spectrum of the Proton

In DMSO, at 300 MHz, chemical shifts of the peaks in ppm and multiplicity:

2.10 (ddd) and 2.43 (dm): N—$CH_2$—CHO—$CH_2$; 2.83 (tt): $O_2C$—CH—; 3.13 (d) and 3.27 (dm): N—$CH_2$—CHO; 3.40 (dd) an$\overline{d}$ 3.72 (d): N—$CH_2$—CH—$CO_2H$; 4.81 (m): N—$CH_2$—CHO; 12.54 (broad $\overline{s}$): $CO_2H$.
IR (nujol): $\overline{1}$782, 1692 $cm^{-1}$.

MS (EI) m/z: [M]$^+$=177, 155, 127, 82, 70.

Example 12c (4-nitrophenyl)methyl trans-7-oxo-6-oxa-1-azabicyclo[3,2,1] octane-3-carboxylate 30 mg (0.175 mmole) of the acid obtained in Example 12b and 0.5 ml of dichloromethane are mixed together under an inert atmosphere. 26.8 mg of 4-nitrobenzylic alcohol, 2.2 mg of DMAP and 37 mg of EDCI are then added.

The reaction medium is left to react whilst agitating for 2 hours at ambient temperature.

The organic phase is then diluted with dichloromethane, washed with a 10% aqueous solution of tartaric acid and a phosphate buffer solution at pH 7.

After drying the organic phase over sodium sulphate, and evaporation of the solvent under reduced pressure, 57 mg of crude product is obtained which is purified by chromatography on silica eluting with a toluene/ethyl acetate mixture 85/15.

The product is then crystallized from a mixture of ethyl ether and pentane in order to produce 34 mg of white crystals of the sought compound (M=306.277 g). The corresponding yield is 63.5%.

NMR Spectrum of the Proton

In $CDCl_3$, at 300 MHz, chemical shifts of the peaks in ppm and multiplicity:

2.14 (ddd) and 2.84 (dm): N—CH$_2$—CHO—CH$_2$; 2.90 (tt) O$_2$C—CH—; 3.10 and 3.49 (dm); N—CH$_2$—$\overline{\text{CHO}}$; 3.43 (dd) and 4.14 (bd): N—CH$_2$—CH—$\overline{\text{CO}_2}$; 5.27 [AB]: $\overline{\text{CO}_2}$—CH$_2$—C$_6$H$_5$; 7.56 and 8.24 [AA'BB']: C—C$_6$H$_5$—NO$_2$—

IR (CHCl$_3$): 1799, 1789, 1741; 1609, 1526, 1495 cm$^{-1}$.
MS (EI) m/z: [M]$^+$: 306, 170, 136, 126, 106, 82.

Example 13

6-(phenylmethyl)-1,6-diazabicyclo[3,2,1]octan-7-one

Stage A:
30.7 ml of TEA is added at about 0-5° C. to a solution of 20.71 g of 3-amino-pyridine in 200 ml of methylene chloride, then, 25.5 ml of benzoyl chloride is added dropwise over 15 minutes and the reaction medium is left to return to ambient temperature. After 1 hour under agitation, the reaction medium is washed with water, then with a saturated solution of sodium bicarbonate, then the organic phase is dried over sodium sulphate and the solvent is evaporated off under reduced pressure. 42.29 g of expected crystallized product (M=198.226 g) is obtained.

Stage B:
4.3 ml of concentrated hydrochloric acid and 500 mg of rhodium on aluminium at 5% by weight are added to a solution of 10 g of the product obtained in stage A in 200 ml of methanol. The reaction medium is placed under a hydrogen atmosphere at a pressure of 60-110 bars for 15 hours.

The reaction mixture is filtered, rinsed with methanol then the filtrate is concentrated under reduced pressure. The hydrochloride of the expected product is obtained in a mixture with 10% hydrochloride of the starting product.

The product is taken up in 250 ml of methylene chloride and 1.1 equivalent of 1N soda is added. After agitation for 15 minutes, the methylene chloride is decanted, the organic phase is washed with water, dried and evaporated under reduced pressure. The residue is chromatographed on silica eluting with a methylene chloride-methanol-triethylamine mixture 92/8/3.

7.4 g of expected crystallized product is obtained, i.e. a yield of 72%.

Stage C:
N-(phenylmethyl)-3-piperidinamine
20 g of the product obtained as described in stage B is dissolved in 600 ml of 1,2-dimethoxyethane. 14.8 g of lithium aluminium hydride is added to the solution over 30 minutes. The reaction medium is heated under agitation and under an inert gas at 75-80° C. for 16 hours then cooled down to 0° C. and 11 ml of water is added over 45 minutes, without exceeding 12° C. The reaction medium is agitated for 10 minutes, filtered and the precipitate is washed with methylene chloride. The filtrate is concentrated under reduced pressure. 17.8 g of expected product is obtained, in the form of an oil which is distilled under reduced pressure (boiling point: 114-121° C./0.8 mbar). 16 g of expected product is recovered, i.e. a yield of 86%.

Stage D:
6-(phenylmethyl)-1,6-diazabicyclo[3,2,1]octan-7-one
1.06 g of the product obtained in stage C is dissolved in 28 cm$^3$ of toluene, then cooled down to 0° C. and 337 µl of diphosgene is added under an inert gas. Then the temperature is left to rise and maintained for 2 hours at 20° C. The reaction medium is concentrated under reduced pressure then the residue is chromatographed on silica eluting successively with methylene chloride-acetone 95/5 then 80/20 and finally methylene chloride-methanol, triethylamine 92/8/3 and 362 mg of expected product C$_{13}$H$_{16}$N$_2$O (M=216.85 g) is obtained i.e. a yield of 30%.

CPV/Mass spectrometry (EI) m/z: [M]$^+$=216, 125, 91.
IR (CHCl$_3$): 1718; 1498 cm$^{-1}$.

Example 14

6-benzoyl-1,6-diazabicyclo[3,2,1]octan-7-one

Stage A:
3-(benzylamino)-1-piperidinecarboxylic
5 g of product obtained in stage B of Example 13 is dissolved in 1.25 l of anhydrous toluene under a nitrogen atmosphere then 3.4 ml of TEA is added and 1.47 ml of diphosgene is introduced at 0-5° C. over 3 minutes After 20 minutes at 0-5° C., the reaction medium is heated to 20° C., it is maintained under agitation for 75 minutes, then the solvent is evaporated off under reduced pressure. The residue is chromatographed on silica eluting with a methylene chloride-acetone mixture 8/2. 3.44 g of expected product is obtained (yield of 52.6%).

Stage B
6-benzoyl-1,6-diazabicyclo[3,2,1]octan-7-one
48 mg of sodium hydride at 50% dispersed in oil and 20 ml of THF are introduced under a nitrogen atmosphere. The reaction medium is cooled down to about 0-5° C., then 266 mg of the product obtained in stage A is added in one go.

The temperature is left to rise to ambient temperature, then 60 µl of acetic acid and 10 ml of phosphate buffer at pH 7 are added.

A little ethyl acetate is then added, then the reaction medium is decanted and re-extracted with ethyl acetate. The organic phase is dried over magnesium sulphate, then the solvents are evaporated off under reduced pressure.

The crude product is chromatographed on silica eluting with dichloromethane containing 2% acetone.

143 mg of the sought product C$_{13}$H$_{12}$N$_2$O$_2$ (M: 228.25 g) is thus obtained. The corresponding yield is 62%.

NMR Spectrum of the Proton
In CDCl$_3$, at 250 MHz, chemical shifts of the peaks in ppm and multiplicity:

1.20-2.15 (m) and 2.42 (m): NCH—CH$_2$—CH$_2$—; 2.80 (d)—2.93 (d); 3.11 (m); 3.28 to 3.58 (m): $\overline{\text{CH}_2}$—$\overline{\text{N}}$; 4.54 (m) CH—N; 7.43 (m); 7.55 (m); 7.69 (m): C$_6$$\overline{\text{H}_5}$ IR (CHCl$_3$): 1758, 1672; 1605, 1586, 1492;
MS (EI) m/z: [M]$^+$=230, 125, 105, 77

Example 15

7-oxo-1,6-diazabicyclo[3,2,1]octan-6-acetic acid

Stage A:
5-[(1,1-dimethylethyl)dimethylsilyl]-1,6-diazabicyclo[3-2-1]octan-7-one]
843 mg of lithium is placed under a nitrogen atmosphere and 320 ml of ammonia is condensed at −70° C. 7.56 g (34.8 mmoles) of the product obtained in Example 13 in 160 ml of tetrahydrofuran is added at −70° C. over 10 minutes. Agitation is carried out for 5 minutes then the ammonia is distilled under a stream of nitrogen whilst heating slowly at 20° C., 7.9 g of (1,1-dimethylethyl)dimethylsilyl chloride in 10 cm$^3$ of tetrahydrofuran is added slowly at 20° C. to the obtained suspension then maintained under agitation for 10 minutes. 160 cm$^3$ of ethyl acetate then 60 cm$^3$ of a 10% aqueous solution of tartaric acid is then added. Decanting is carried out followed by re-extracting with ethyl acetate, the organic phase is washed with water, dried over sodium sulphate and the solvent is evaporated off under reduced pressure. The oil obtained is chromatographed on silica with 10% water, eluting with methylene chloride then a methylene chloride-acetone mixture 8/2 and 3.04 g of expected product is obtained (yield: 36.2%)

NMR Spectrum of the Proton

In CDCl$_3$, at 250 MHz, chemical shifts of the peaks in ppm and multiplicity:

0.21(S) and 0.40(S): SiCH$_3$; 0.97(S): SitBu; 1.5 to 1.8(m) and 2.07(m): N—CH—CH$_2$—CH$_2$; 2.85 (d) and 3.32 (m); —CH—CH$_2$—N: 2.93 (dt) and 3.32 (m): —CH$_2$—CH$_2$—N; 3.65 (m): CH—N.

IR (CHCl$_3$): 1710; 842 cm$^1$.

MS (EI) m/z: [M]$^+$: 240, 225, 183, 100, 83, 57.

Stage B:

phenylmethyl 7-oxo-1,6-diazabicyclo[3,2,1]octan-6-acetate 1.44 g (5.99 mmoles) of the product obtained in stage A is dissolved under a nitrogen atmosphere in 14.4 ml of tetrahydrofuran then 941 µl of phenylmethyl bromoacetate is added and then 6 ml of a 1M solution of tetra-n-butyl ammonium fluoride in tetrahydrofuran is added dropwise. The reaction medium is agitated for 10 minutes at 20° C. then diluted with 15 ml of ethyl acetate and 5 ml of an aqueous phosphate buffer solution at pH=7 is added. The reaction medium is decanted, re-extracted with ethyl acetate, the organic phase is washed with water, dried over sodium sulphate and the solvent is evaporated off under reduced pressure. The oily residue is chromatographed on silica with 10% water eluting with a methylene chloride-acetone mixture 8/2. 140 mg of the expected product is obtained. The corresponding yield is 9%.

IR (CHCl$_3$): 1746, 1720 cm$^{-1}$.

MS (EI) m/z: [M]$^+$=274, 183, 155, 139, 91, 83.

Stage C: 7-oxo-1,6-diazabicyclo[3.2.1]octane-6-acetic acid 137 mg of the product obtained in stage B is dissolved in 1.5 ml of ethyl acetate, then added to the solution of 14 mg of palladium on carbon at 10% and placed under a hydrogen atmosphere. After 15 minutes another 15 mg of palladium on carbon is added and the reaction medium is maintained under agitation for 15 minutes. The catalyst is filtered out, followed by rinsing with ethyl acetate, then with acetone and methanol and the solvent is evaporated off under reduced pressure. A total of 68 mg of crude product is obtained which is crystallized from ether. 58 mg of the expected product with molecular formula C$_{15}$H$_{18}$N$_2$O$_3$ (M=274.321 g) is obtained. The corresponding yield is 63%.

NMR Spectrum of the Proton

In CDCl$_3$, at 400 MHz, chemical shifts of the peaks in ppm and multiplicity:

1.48 (m), 1.63 (m), 1.73 (m) and 1.86 (m): N—CH—CH$_2$—CH$_2$; 2.85 to 3.00 (m), 3.14 (dm) and 3.64 (m): CH$_2$—N—CH$_2$ and CH—N; 3.78 and 4.14 [AB]: CON—CH$_2$—CO.

MS (EI) m/z: [M]$^+$=184, 139, 125, 111, 97, 83.

Example 16

7-oxo-N-phenyl-1,6-diazabicyclo[3,2,1]octane-6-carboxamide 1 ml of tetrahydrofuran and 99 mg (0.41 mmole) of the compound obtained in stage A of Example 15 are mixed together under an inert gas.

50 µl of phenyl isocyanate then 450 µl of a 1M solution of tetrabutylammonium fluoride in THF are added successively.

The reaction medium is left to react for 10 minutes, then diluted with ethyl acetate, and washed with water. The reaction medium is decanted and the organic phase is dried over magnesium sulphate. The solvent is evaporated off under reduced pressure. 140 mg of crude product is thus obtained which is purified by chromatography on silica using a dichloromethane/ethyl acetate mixture 90/10 as eluent.

21 mg of the compound of the title, with molecular formula C$_{13}$H$_{15}$N$_3$O (M=245.283 g) is recovered which corresponds to a yield of 20%.

NMR Spectrum of the Proton

In CDCl$_3$, at 250 MHz, chemical shifts of the peaks in ppm and multiplicity:

1.78 (m), 2.02 (m) and 2.17 (m): N—CH—CH$_2$—CH$_2$; 2.88 (d), 3.13 (dt) and 3.42 (m): CH$_2$—N—CH$_2$; 4.49 (m): CH—N; 7.11(t); 7.34(t) and 7.54(d): C$_6$H$_5$; 10.05: NH.

IR (CHCl$_3$): 3302, 3266; 1734; 1700; 1602, 1553, 1501 cm$^{-1}$.

MS (EI) m/z: [M]$^+$: 245, 153, 126, 119, 98, 92.

Example 17a

6-[1-(phenylmethyl)-1H-tetrazole-5-yl]-1,6-diazabicyclo [3,2,1]octan-7-one 480 mg (2 mmoles) of the compound obtained in stage A of Example 15 is placed under an inert gas.

Then a solution of 712 mg of 5-fluoro-1-(phenylmethyl)-1H-tetrazole in 1.5 ml of tetrahydrofuran then 2 ml of a 1M solution of tetrabutylammonium fluoride in THF are added. The reaction medium is left to react for 1 minute.

The reaction medium is then diluted with ethyl acetate, washed with water, decanted, the organic phase is dried over magnesium sulphate and the solvent is evaporated off under reduced pressure.

1.06 g of an oily product is obtained which is chromatographed on silica in a dichloromethane/ethyl acetate mixture 90/10.

143 mg of the expected compound with molecular formula C$_{14}$H$_{16}$N$_6$O (M=284.324 g) is thus obtained in the form of an amorphous white product. The corresponding yield is 25%.

NMR Spectrum of the Proton

In CDCl$_3$, at 250 MHz, chemical shifts of the peaks in ppm and multiplicity:

1.80 (m), 2.04 (m) and 2.67 (m): N—CH—CH$_2$—CH$_2$; 2.83 (d), 2.85 (dm), 3.10 (dd) and 3.44 (dd): CH$_2$—N—CH$_2$; 3.99 (m): CH—N; 5.63 and 5.88 [AB]: C$_6$H$_5$—CH$_2$; 7.18 (m) and 7.32 (m): C$_6$H$_5$.

Example 17b 6-(1H-tetrazole-5-yl)-1,6-diazabicyclo[3,2,1]octan-7-one 120 mg of the product obtained in Example 17a and 2.4 ml of a methanol/ethyl acetate mixture 90/10 are mixed together then 2.4 ml of THF is added until total dissolution is obtained.

24 mg of palladium catalyst on carbon at 10% is then added, then the reaction medium is agitated under a hydrogen atmosphere. After 3 hours of reaction, the catalyst is filtered out, followed by rinsing with a tetrahydrofuran/methanol mixture, then the solvent is evaporated off under reduced pressure. The product is then crystallized from ethyl ether.

72 mg of the compound of the title with molecular formula $C_7H_{10}N_6O$ (M=194.198 g) is thus obtained, in the form of a white crystallized product. The corresponding yield is 88%.

NMR Spectrum of the Proton

In DMSO, at 300 MHz, chemical shifts of the peaks in ppm and multiplicity:

1.63 (m), 1.89 (m) and 2.07 (m): N—CH—CH$_2$—CH$_2$; 3.14 to 3.20 (m) and 3.43 (m): CH$_2$—N—CH$_2$; 4.51 (m) CH—N.

IR (Nujol): 1744; 1594 cm$^{-1}$.

MS (EI) m/z: [M]$^+$=194, 165, 124, 111, 98, 83, 68, 56, 41.

Example 18

6-acetyl-1,6-diazabicyclo[3,2,1]octan-7-one 140 mg (0.582 mmoles) of the compound obtained in stage A of Example 15 is dissolved in 1.4 ml of THF.

55 µl of acetic anhydride then 0.58 ml of a 1M solution of tetrabutylammonium fluoride in THF are added successively.

The reaction medium is then diluted with ethyl acetate, washed with water, decanted, the organic phase is dried over magnesium sulphate, then the solvent is evaporated off under reduced pressure.

In this way 116 mg of a crude oil is obtained which is chromatographed on silica with a dichloromethane/acetone mixture 80/20.

18 mg of expected compound, with molecular formula $C_8H_{12}N_2O_2$ (M=168.196 g) is thus obtained, which corresponds to a yield of 18%.

NMR Spectrum of the Proton

In DMSO, at 300 MHz, chemical shifts of the peaks in ppm and multiplicity:

1.65 to 2.20 (m): N—CH—CH$_2$—CH$_2$; 2.54 (s): CH$_3$CO—N; 2.83 (d), 3.33(dm), 3.10 (m) and 3.45 (dd) CH$_2$—N—CH$_2$; 4.55 (m): O=C—N—CH.

IR (CHCl$_3$): 1758, 1696 cm$^{-1}$.

MS (EI) m/z: [M]$^+$=168, 140, 126, 98, 43.

Example 19a 6-(phenylmethoxy)-1,6-diazabicyclo[3,2,1]octan-7-one 44.02 g (0.22 mole) of 1,1-dimethylethyl 3-oxo-1-piperidinecarboxylate ($C_{10}H_{17}NO_3$, M=199.251 g) (described in J. Med. Chem. 1986, 29, 224-229) is dissolved in 440 ml of ethanol.

38.79 g of O-benzyl-hydroxylamine hydrochloride is then added. 54 ml of pyridine is then introduced dropwise into the suspension.

The reaction medium is left to react whilst agitating for 4 hours at approximately 25° C., then the solvent is evaporated off under reduced pressure. The reaction medium is taken up by a mixture of dichloromethane and ethyl acetate, then filtered and rinsed with dichloromethane, then with a mixture of dichloromethane and ethyl acetate. The filtrate is then concentrated to dryness under reduced pressure.

69.8 g of a light yellow oil is thus obtained which is purified by chromatography on silica. The eluent used is a cyclohexane/ethyl acetate mixture 80/20.

57.21 g of 1,1-dimethylethyl 3-[(phenylmethoxy) imino]-1-piperidinecarboxylate, with molecular formula $C_{17}H_{24}N_2O_3$ (M=304.39 g) is recovered, in the form of a very pale yellow oil. The corresponding yield is 85%.

24.82 g (0.0815 mmole) of the oxime obtained previously is dissolved in 163 ml of ethanol cooled down to −10° C. under nitrogen. Then 25 ml of a borane-pyridine complex is added, then 204 ml of 2N hydrochloric acid is added dropwise over an hour and quarter. The solution is agitated for 1 hour and a quarter at −5° C., then treated with 100 ml of a saturated sodium hydrogen carbonate solution, then with 35 g of sodium carbonate, which are added in small fractions. The pH is then 7-8.

The reaction medium is extracted with ethyl acetate.

The organic phases are combined, dried over sodium sulphate, the solvent is evaporated off under reduced pressure. 39.0 g of a colourless oily liquid is thus obtained that is taken up in 400 ml of ethyl acetate.

The solution is washed with a 0.05 N aqueous solution of hydrochloric acid, then the organic phases are combined and the solvent is evaporated off under reduced pressure.

35.5 g of an oily colourless liquid is recovered which is purified by chromatography on silica, eluting with a dichloromethane/ethyl acetate mixture 95/5, then with a dichloromethane/ethyl acetate mixture 80/20.

17.89 of 1,1-dimethylethyl 3-[(phenylmethoxy)amino]-1-piperidinecarboxylate with molecular formula $C_{17}H_{26}N_2O_3$ (M=306.41 g) is thus recovered in the form of a colourless oil. The corresponding yield is 72%.

6.72 g (21.9 mmoles) of the piperidine obtained previously is dissolved in 22 ml of ethyl acetate cooled down to −10° C. 28 ml of a 4.0 mol/l solution of anhydrous hydrochloric acid in ethyl acetate is added dropwise over 30 minutes.

After 1 hour at 0° C., 40 ml of ethyl ether is added, the dihydrochloride precipitate is filtered and washed with ethyl ether.

In this way 3.87 g of a white solid is obtained.

Another 1.80 g of the desired product is obtained by crystallization of the filtrate.

The product obtained is taken up in 60 ml of 1N soda and 120 ml of ethyl acetate. After decantation, the aqueous phase is saturated with sodium chloride, then extracted twice with ethyl acetate. The organic phases are combined and dried over magnesium sulphate then concentrated to dryness under reduced pressure.

3.67 g of N-(phenylmethoxy)-3-piperidinamine, with molecular formula $C_{12}H_{18}N_2O$ (M=206.29 g) is thus obtained, which corresponds to a yield of 81%.

518 mg (2.5 mmoles) of the compound obtained previously is dissolved in 5 ml of anhydrous dichloromethane, then 0.5 ml of TEA is added.

The whitish suspension obtained is cooled down to −65° C., then 12.5 ml of a 0.10 mol/l solution of diphosgene in dichloromethane is added over 15 minutes.

After reaction for 45 minutes, the colourless solution is diluted with 15 ml of dichloromethane and treated with 15 ml of water.

The medium is left to settle, then the aqueous phase is extracted with 20 ml of dichloromethane.

The combined organic phases are dried over magnesium sulphate, then concentrated to dryness under reduced pressure. A pale yellow oil is thus obtained which is purified by chromatography on silica eluting with an ethyl acetate mixture 90/10, then a dichloromethane/ethyl acetate mixture 80/20.

In this way 196 mg of expected compound with molecular formula $C_{13}H_{16}N_2O_2$, (M=232.28 g) is recovered in the form of a colourless oil. The corresponding yield is 34%.

NMR Spectrum of the Proton

In CDCl$_3$, at 300 MHz, chemical shifts of the peaks in ppm and multiplicity:

1.59 (m) and 1.93 to 2.18 (m): N—CH—CH$_2$—CH$_2$; 2.73 (dt), 2.94 (dt), 3.17(dt) and 3.40 (dd): CH$_2$—N—CH$_2$; 3.29 (t): N—CH; 4.89 (d): N—O—CH$_2$—(C$_6$H$_5$); 7.38: C$_6$H$_5$.

IR (CHCl$_3$): 1747; 1498 cm$^{-1}$.
MS (EI) m/z: [M]$^+$=232, 91.

Example 19b 6-(acetyloxy)-1,6-diazabicyclo[3,2,1]octan-7-one 95 mg (0.41 mmole) of the compound obtained in Example 19a is dissolved in 5 ml of methanol, 8 mg of palladium on carbon at 10% by weight is agitated, then the suspension is placed under a hydrogen atmosphere under normal pressure for 1 hour at 25° C., then the catalyst is filtered out.

After evaporation of the solvent under reduced pressure, 70 mg of white crystals are obtained.

The crystals are taken up in 2 ml of anhydrous dichloromethane. The solution is cooled down to –10° C. under nitrogen. Then 70 µl of pyridine, then 40 µl of acetic anhydride are added and agitation is carried out for 20 minutes. The reaction medium is concentrated under reduced pressure and 75 mg of white crystals are obtained which are purified on silica, eluting with a dichloromethane ethyl acetate mixture 80/20.

49 mg of expected compound (M=184.20 g) is recovered in the form of a white solid. The corresponding yield is 65%.

NMR Spectrum of the Proton

In CDCl$_3$, at 300 MHz, chemical shifts of the peaks in ppm and multiplicity:

1.60 to 2.2: N—CH—CH$_2$—CH$_2$; 2.24 (s): CH$_3$; 2.95 (d) and 3.54 (dm): N—CH$_2$—CH; 3.07 (dt) and 3.54 (bdd): N—CH$_2$—CH$_2$; 3.94 (bt): O=C—N—CH.

IR (CHCl$_3$): 1798; 1764 cm$^{-1}$.
MS (EI) m/z: [M]$^+$=184, 142, 125, 43.

Example 19c 6-(benzoyloxy)-1,6-diazabicyclo[3,2,1]octan-7-one

The operation is carried out in a similar manner to that described in Example 19b starting with 205 mg of the compound prepared in Example 19a and 200 mg of benzoic anhydride.

In this way 64 mg of expected compound with molecular formula C$_{13}$H$_{14}$N$_2$O$_3$ (M=246.27 g) is obtained i.e. a yield 30%.

NMR Spectrum of the Proton

In CDCl$_3$, at 250 MHz, chemical shifts of the peaks in ppm and multiplicity:

1.64 to 1.95 (m) and 2.10 to 2.35 (m): CH—CH$_2$—CH$_2$; 3.02 (d) and 3.65 (dm): N—CH$_2$—CH; 3.13 (dt) and 3.55 (bdd): N—CH$_2$—CH$_2$; 4.09 (bt): O=C—N—CH; 7.49 (m): 7.65 (tt); 8.12 (m): C$_6$H$_5$.

IR (CHCl$_3$): 1774, 1756; 1602, 1585, 1495 cm$^{-1}$.
MS (EI) m/z: [M]$^+$=246, 105, 77.

Example 19d 6-(1-oxopropoxy)-1,6-diazabicyclo[3,2,1]octane-7-one

The operation is carried out in a similar manner to that described in Example 19c, starting with 163 mg of the compound prepared in Example 19a and 70 µl of propionyl chloride.

In this way 17 mg of expected compound with molecular formula C$_9$H$_{14}$N$_2$O$_3$ (M=198.23 g) is obtained, i.e. a yield of 12%.

NMR Spectrum of the Proton

In CDCl$_3$, at 300 MHz, chemical shifts of the peaks in ppm and multiplicity:

1.25 (t): O=C—CH$_2$—CH$_3$; 1.65 (m), 1.78 (m) and 2.10 (m):
N—CH—CH$_2$—CH$_2$; 2.52 (m) O=C—CH$_2$—CH$_3$; 2.94 (d) and 3.55 (bd): N—CH$_2$—CH; 3.07 (dt) and 3.48 (dd): N—CH$_2$—CH$_2$; 3.93 (m): N—CH$_2$—CH.

IR (CHCl$_3$): 1792; 1763 cm$^{-1}$.
MS (EI) m/z: [M]$^+$=198, 170, 142, 125, 97, 57.

Example 19e

6-[[(4-methylphenyl)sulphonyl]oxy]-1,6-diazabicyclo [3,2,1]octan-7-one

The operation is carried out in a similar manner to that described in Example 19d, staring with 139 mg of the compound prepared in Example 19a and 126 mg of tosyl chloride.

In this way 77 mg of expected compound with molecular formula C$_{13}$H$_{16}$N$_2$O$_4$S (M=296.35 g) is obtained, i.e. a yield of 44%.

NMR Spectrum of the Proton

In CDCl$_3$, at 250 MHz, chemical shifts of the peaks in ppm and multiplicity:

1.55 and 2.99 (m): N—CH—CH$_2$—CH$_2$; 2.45 (s): CH$_3$; 2.89 (d), 3.00 (dt), 3.29 (dt) and 3.39 (dd): CH$_2$—N—CH$_2$; 4.04 (m): N—CH; 7.35 and 7.91 [AA'BB'] CH$_3$—C$_6$H$_4$—SO$_2$.

IR (CHCl$_3$): 1775; 1599, 1495, 1383; 1193, 1180 cm$^1$.
MS (EI) m/z: [M]$^+$=296, 155, 141, 125, 91.

Example 19f

6-[(methylsulphonyl)oxy]-1,6-diazabicyclo[3,2,1] octan-7-one

The operation is carried out in a similar manner to that described in Example 19e starting with 211 mg of the compound prepared in stage 19a and 80 µl of mesyl chloride.

In this way 50 mg of expected compound with molecular formula C$_{17}$H$_{12}$N$_2$O$_4$S (M 220.25 g) is obtained i.e. a yield of 25%.

NMR Spectrum of the Proton

In CDCl$_3$, at 250 MHz, chemical shifts of the peaks in ppm and multiplicity:

1.56 and 2.38 (m): N—CH—CH$_2$—CH$_2$; 3.00 (d), 3.12 (dt) and 3.49 (m): N—(CH$_2$)$_2$; 3.26 (s): CH$_3$; 4.12 (m): N—CH.

IR (CHCl$_3$): 1775; 1381, 1187 cm$^{-1}$.
MS (EI) m/z: [M]$^+$=220, 141, 125, 97, 79.

Example 19g

6-[(4-nitrophenyl)sulphonyl]oxy]-1,6-diazabicyclo [3,2,1-octan-7-one-

The operation is carried out in a similar manner to that described in Example 19f starting with 270 mg of the compound prepared in Example 19a and 283 mg of 4-nitrobenzenesulphonyl chloride.

In this way 205.5 mg of expected compound with molecular formula $C_{12}H_{13}N_3O_6S$ (M=327.32 g) is obtained i.e. a yield of 54%.

NMR Spectrum of the Proton

In $CDCl_3$, at 250 MHz, chemical shifts of the peaks in ppm and multiplicity:

1.64 (dt), 1.84 (m), 1.99 (m), 2.31 (dm): NCH—$CH_2$—$CH_2$; 2.94 (d), 3.30 (dt), 3.04 (dt), 3.40 (bdd): $N(CH_2)_2$; 4.14: O=C—N—CH; 8.25 and 8.41 [AA'BB']: $NO_2$—$C_6H_4SO_2$.

IR ($CHCl_3$): 1776; 1610, 1590, 1538; 1393, 1191 $cm^{-1}$.

MS (EI) m/z: $[M]^+$=327, 186, 141, 125, 111.

Example 20

6-[[(4-methylphenyl)sulphonyl]amino]-1,6-diazabicyclo [3,2,1] octan-7-one 5 g (25.1 mmole) of 1,1-dimethylethyl 3-oxo-1-piperidine carboxylate (described in J. Med. Chem. 1986, 29, 224-229) ($C_{10}H_{17}NO_3$, M=199.251 g) is dissolved in 50 ml of dichloromethane.

4.67 of tosylhydrazine is then added to the solution and left to react for 2 hours under agitation, then the solvent is evaporated off under reduced pressure.

9.56 g of 1,1-dimethylethyl 3-[2-[(4-methylphenyl) sulphonyl]hydrazono]-1-piperidinecarboxylate, with molecular formula $C_{17}H_{25}N_3O_4S$ (M=367.47 g) is thus obtained, with a quantitative yield.

4.5 g (12.2 mmoles) of the compound obtained previously, 90 ml of a methanol/tetrahydrofuran mixture 50/50, and a few grains of bromocresol green are mixed together under an inert gas.

1.62 g of $NaBH_3CN$ is then added, then the reaction medium is cooled down to 0-5° C., and, a solution of 0.7 mol/l of gaseous hydrogen chloride in methanol is introduced in such a way as to keep the pH of the medium between 3.8 and 5.4.

The reaction medium is left to react whilst agitating for 2 and a half hours.

⅔rds of the solvent is evaporated off under reduced pressure, then 200 ml of dichloromethane is added and the medium is washed with a saturated aqueous solution of sodium bicarbonate.

The organic phase is dried over sodium sulphate and the solvent is evaporated off under reduced pressure.

In this way 4.48 g of 1,1-dimethylethyl 3-[2-[(4-methylphenyl) sulphonyl]hydrazino]-1-piperidine carboxylate with molecular formula $C_{17}H_{27}N_3O_4S$ (M=369.486 g) is obtained.

The corresponding yield is 99%.

4.48 g of the compound obtained previously and 9 ml of ethyl acetate are mixed together under an inert gas at 0° C.

30 ml of a 4 mol/l solution of gaseous hydrogen chloride in ethyl acetate is added, agitation is carried out for 15 minutes followed by filtering and the hydrochloride is washed with ethyl acetate. Drying is carried out under reduced pressure and 3.48 g of 2-(3-piperidinyl)hydrazide dihydrochloride of 4-methyl-benzenesulphonic acid, with molecular formula $C_{12}H_{19}N_3O_2S$, 2HCl (M=342.289 g) is obtained. The corresponding yield is 84%.

3.48 g of the compound obtained previously and 5 ml of demineralized water are then dissolved. 10.2 ml of an aqueous solution of 2 N soda is added under vigorous agitation.

A precipitate is formed after 1 to 2 minutes of contact. Agitation is then carried out for 10 minutes, then the precipitate is filtered and washed with water, then ethyl acetate.

The solid obtained is dried under reduced pressure.

In this way 2.21 g of 2-(3-piperidinyl)hydrazide of 4-methyl-benzenesulphonic acid, with molecular formula $C_{12}H_{19}N_3O_2S$ (M=269.328 g) is obtained. The corresponding yield is 81%.

500 mg (1.85 mmole) of the amine obtained previously and 20 ml of tetrahydrofuran are mixed together under an inert gas.

112 µl of diphosgene then 517 µl of TEA and 23 mg of DMAP are added to the suspension obtained, at a temperature comprised between 0 and 5° C.

The reaction medium is left to react whilst agitating and leaving the temperature to rise to 20° C.

The reaction medium is then diluted with ethyl acetate, then washed with a 10% aqueous solution of tartaric acid, then with demineralized water.

The organic phase is dried over magnesium sulphate, then the solvent is evaporated off under reduced pressure.

769 mg of a crude product is obtained which is dissolved in 7 ml of dichloromethane and 517 µl of TEA.

The reaction medium is left to react overnight under agitation.

The reaction medium is diluted with dichloromethane, washed with water, dried over sodium sulphate and the solvent is evaporated off under reduced pressure.

The foam obtained (395 mg) is purified by chromatography on silica with a dichloromethane/ethyl acetate mixture 80/20.

44 mg of the expected compound, with molecular formula $C_{13}H_{17}N_3O_2S$ (M=295.362 g) is recovered. The corresponding yield is 8%.

NMR Spectrum of the Proton

In $CDCl_3$, at 250 MHz, chemical shifts of the peaks in ppm and multiplicity:

1.55 to 1.80 (m) and 2.18 (m): N—CH—$CH_2$—$CH_2$; 2.42 (s): $CH_3$; 2.88 (d) and 2.93 (m); N—$CH_2$—CH; 3.18 to 3.32 (m): N—$CH_2$—$CH_2$; 4.08 (m): N—CH—$CH_2$; 6.98 (bs): NH.

IR ($CHCl_3$): 3264, 1737, 1599, 1490 $cm^{-1}$.

MS (positive electrospray) m/z: $[M+Na]^+$=318, $[M+H]^+$=296

Example 21

6-[(4-methylphenyl)sulphonyl]-1,6 diazabicyclo[3,2,1] octan-7-one 305 mg (1.52 mmole) of 1,1-dimethylethyl 3-amino-1-piperidinecarboxylate (described in J. Med. Chem. 1992, 35, 4334-4343), with molecular formula $C_{10}H_{20}N_2O_2$ (M=200.282 g) is dissolved in 3 ml of anhydrous dichloromethane.

212 µl of TEA is then added, then the solution is cooled down to 5° C. and 278 mg of tosyl chloride is added. The reaction medium is agitated whilst allowing the temperature to return to 20° C. and left to react for 2 hours.

The reaction medium is then diluted with dichloromethane and washed firstly with a 10% aqueous solution of tartaric acid then with a phosphate buffer solution at pH=7.

The organic phase is separated and dried over magnesium sulphate, then the solvent is evaporated off under reduced pressure. An oil is thus obtained which is purified by chromatography on silica eluting with a dichloromethane/ethyl acetate mixture 9/1.

440 mg of 1,1-dimethylethyl 3-[[(4-methylphenyl) sulphonyl]amino]-1-piperidinecarboxylate (described in J. Med.

Chem. 1992, 35, 4334-4343) with molecular formula $C_{17}H_{26}N_2O_4S$ (M=354.472 g) is recovered. The corresponding yield is 82%.

A mixture of 425 mg of the compound obtained previously and 2.1 ml of a trifluoroacetic acid/dichloromethane mixture 50/50 are cooled down to 0-5°.

The reaction medium is kept under agitation at 5° C. for 30 minutes.

The solvent is then evaporated off under reduced pressure in order to obtain 403 mg of 4-methyl-N-(3-piperidinyl)-benzenesulphonamide trifluoroacetate with molecular formula $C_{14}H_{19}F_3N_2O_4S$ (M=368.377 g). 228 mg of the compound obtained previously is placed in suspension in 2 ml of methanol. The reaction medium is treated with an excess of DOWEX 21K 20-50 Mesh resin activated with soda.

After filtering, the resin is rinsed with the methanol, then the filtrate is evaporated under reduced pressure.

In this way 123 mg of 4-methyl-N-(3-piperidinyl)-benzenesulphonamide with molecular formula $C_{12}H_{18}N_2O_2S$ (M=254.353 g) is recovered.

118 mg of the amine obtained previously is dissolved under an inert gas in 1.2 ml of dichloromethane.

98 µl of TEA then 28 µl of diphosgene are then introduced successively. The reaction medium is left to react whilst agitating for 30 minutes at 0-5° C. The reaction medium is diluted with dichloromethane, the organic phase is washed with a 10% aqueous solution of tartaric acid, then with water. After drying over sodium sulphate, filtration and evaporation of the solvent under reduced pressure are carried out, the crude product is purified by chromatography on silica using a dichloromethane/acetone mixture 95/5 as eluent.

In this way 112 mg of the chloride of 3-[[(4-methylphenyl) sulphonyl] amino]-1-piperidinecarboxylic acid, with molecular formula $C_{13}H_{17}ClN_2O_3S$ (M=316.308 g) is obtained. The corresponding yield is 76%.

Under an inert atmosphere, 10 mg of sodium hydride (in suspension at 55-65% in oil) and 2 ml of anhydrous tetrahydrofuran are mixed together.

71 mg of the product obtained previously is then added.

The reaction medium is agitated at ambient temperature for 15 minutes, then 12 µl of acetic acid and 2 ml of phosphate buffer solution at pH=7 are added.

Agitation is carried out-again for 5 minutes, then 5 ml of ethyl acetate is added, the reaction medium is left to settle, then re-extracted with ethyl acetate. The organic phase is then separated and dried over magnesium sulphate, filtered, and the solvent is evaporated off under reduced pressure.

In this way 65 mg of crude product is obtained which is purified by chromatography on silica, eluting with a dichloromethane/acetone mixture 95/5.

In this way 40 mg of expected compound, with molecular formula $C_{13}H_{16}N_2O_3S$ (M=280.348 g) is recovered. The corresponding yield is 64%.

NMR Spectrum of the Proton

In $CDCl_3$, at 250 MHz, chemical shifts of the peaks in ppm and multiplicity (presence of two conformers 90/10):

1.46 (m), 1.76 (m) and 2.08 (dm): $NCH-CH_2-CH_2$; 2.44 (s) and 2.45 (s): $CH_3$; 2.82 (d) and 2.98 (m) and 3.28 to 3.50 (m) — $N-(CH_2)_2$; 4.55 (m) and 4.65 (m): $CO-N-CH$; 7.33 and 7.78, 7.35 and 8.02 [AA'BB'] $CH_3-C_6H_4-SO_2$.

IR ($CHCl_3$): 1758, 1598, 1995, 1367, 1169 cm$^{-1}$.

MS (EI) m/z: [M]$^+$: 280, 216, 155, 125, 97, 91.

Example 22

6-oxa-1-azabicyclo[3,2,1]oct-3-en-7-one 5 ml of dichloromethane and 68 mg of 1,2,3,6-tetrahydropyridin-3-ol hydrochloride (M=135.5 g) (described in Chem. Pharm. Bull. 30(10)3617-3623(1982)) are mixed together under an inert gas.

33 µl of diphosgene is added and agitation is carried out for 5 minutes at 0° C. Then 140 µl of TEA and 61 mg of DMAP are added.

The reaction medium is left to react at ambient temperature for 2 hours: then diluted with dichloromethane and washed with a 10% aqueous solution of tartaric acid then with water. After decanting the organic phase is dried over magnesium sulphate. The solvent is evaporated off under reduced pressure. 5 mg of crude product is thus obtained which is purified by chromatography on silica, eluting with dichloromethane then a dichloromethane/ethyl acetate mixture 95/5.

In this way 3 mg of expected compound, with molecular formula $C_6H_7NO_2$ (M=125 g) is recovered. The corresponding yield is 5%.

Example 23 phenylmethyl trans-3-benzoyl-2-oxo-4-oxa-1,3-diazabicyclo [3,2,1]octane-7-carboxylate 5.50 g (13.7 mmoles) of 1-(1,1-dimethylethyl) and 2-(phenylmethyl) cis-4-[(methylsulphonyl)oxy]-1,2-pyrrolidine dicarboxylate (described in J. Org. Chem. 1991, 56, 3009-3016), with molecular formula $C_{18}H_{25}NO_7S$ (M=399.466 g) and 110 ml of dimethylformamide are mixed together under inert gas, then 2.58 g of N-hydroxyphthalimide, then 1.52 g of potassium hydrogen carbonate are added.

The reaction medium is heated under agitation at 100° C. and kept at this temperature for 4 hours.

The reaction medium is cooled down to 20° C., 220 ml of water and ice are added, then the medium is extracted with isopropyl ether.

Followed by drying over magnesium sulphate, then evaporating to dryness under reduced pressure.

The residue is chromatographed on silica, eluting with a dichloromethane/ethyl acetate mixture 90/10.

In this way 3.06 g of 1-(1,1-dimethylethyl) and 2-(phenylmethyl)trans-4-[(1,3-dihydro-1,3-dioxo-2H-isoindol-2-yl) oxy]-1,2-pyrrolidinedicarboxylate, with molecular formula $C_{25}H_{26}N_2O_7$ (M=466.494 g) is recovered. The corresponding yield is 47%.

3.24 g (6.94 mmoles) of the phthalimide obtained as before is dissolved in 33 ml of dichloromethane.

372 µl of hydrazine hydrate is added.

The reaction medium is again agitated for 2 hours 30 minutes at 20° C.

The precipitate formed is filtered, rinsed with dichloromethane, then the solvent is evaporated off under reduced pressure.

2.91 g of crude product is obtained which is purified by chromatography on silica, eluting with a 90/10, then 80/20 and 50/50 dichloromethane/ethyl acetate mixture.

In this way 942 mg of 1-(1,1-dimethylethyl) and 2-(phenylmethyl) trans-4-(aminooxy)-1,2-pyrrolidine dicarboxylate, with molecular formula $C_{17}H_{24}N_2O_5$ (M 336.39 g) is recovered in total. The corresponding yield is 40%.

853 mg of the compound obtained previously (2.53 mmoles) and 8.5 ml of anhydrous dichloromethane are mixed under an inert gas.

The reaction medium is cooled down to about 0-5° C., then 706 µl of TEA and 588 µl of benzoyl chloride are added.

The reaction medium is agitated for 10 minutes at 0-5° C., then left to heat up to 20° C. and left to react for another 30 minutes.

The organic phase is washed with a 10% aqueous solution of tartaric acid, then with water, then decanted and the organic phase is dried over sodium sulphate. The solvent is evaporated off under reduced pressure.

In this way 1.38 g of product is obtained, which is mixed with 25 ml of dichloromethane. The reaction medium is cooled to about 10-15° C. and 123 µl of hydrazine hydrate is added.

The reaction medium is left to react whilst agitating at 20° C. for two and a half hours.

The solvent is evaporated off under reduced pressure.

1.13 g of crude product is thus obtained which is purified by chromatography on silica, eluting with a dichloromethane/ethyl acetate mixture 80/20.

In this way 948 mg of 1-(1,1-dimethylethyl) and 2-(phenylmethyl)trans-4-[(benzoylamino)oxy]-1,2-pyrrolidine dicarboxylate, with molecular formula $C_{24}H_{28}N_2O_6$ (M=440.50 g) is recovered.

The overall yield is therefore 85%.

948 mg of the compound obtained previously is dissolved in 2 ml of ethyl acetate.

The reaction medium is cooled down to 0-5° C., then 4.7 ml of an approximately 4.6 M solution of gaseous hydrogen chloride in ethyl acetate is added in one go.

After 1 hour, the solvent is evaporated off under reduced pressure and the product is taken up 3 times with ethyl ether.

The solvent is evaporated off under reduced pressure. In this way 842 mg of phenylmethyl trans-4-[(benzoylamino) oxy]-2-pyrrolidinecarboxylate hydrochloride, in the form of a friable white foam with formula $C_{19}H_{20}N_2O_4$, HCl (M=376.84 g) is obtained.

The yield is quantitative.

47 mg (0.125 mmole) of the hydrochloride obtained previously under an inert gas is dissolved in 0.5 ml of dichloromethane. 25.2 µl of pyridine is added, then the reaction medium is cooled down to 0-5° C. and 9.5 µl of diphosgene is added.

The temperature is left to rise to 20° C., the reaction medium is diluted with dichloromethane, then washed with a 10% aqueous solution of tartaric acid then with water.

The organic phase is decanted and dried over sodium sulphate. The solvent is then evaporated off under reduced pressure.

In this way 43.8 mg of crude product is obtained which is purified by chromatography on silica eluting with a dichloromethane/ethyl acetate mixture 90/10.

34.9 mg of phenylmethyl trans-4-[(benzoylamino)oxy]-1-(chlorocarbonyl)-2-pyrrolidinecarboxylate, with molecular formula $C_{20}H_{19}ClN_2O_5$ (M=402.83 g) is recovered.

The corresponding yield is 69%.

13 mg (0.032 mmole) of the compound obtained previously is dissolved in 4 ml of toluene.

9 µl of TEA and 7.8 mg of DMAP are added.

The reaction medium is heated at 100° C. overnight.

The solvent is evaporated off under reduced pressure then the residue is purified by chromatography eluting with dichloromethane.

In this way 4.3 mg of the expected compound, with molecular formula $C_{20}H_{18}N_2O_5$ (M=336.37 g) is recovered. The corresponding yield is 40%.

NMR Spectrum of the Proton

In CDCl$_3$, at 300 MHz, chemical shifts of the peaks in ppm and multiplicity:

1.97 (ddd) and 2.85 (ddd): N—O—CH—CH$_2$—CH; 3.80 (dd) and 4.14 (dd): N—O—CH—CH$_2$—N; 4.75 (dd): N—CH—CH$_2$; 4.93 (t): N—O—CH—CH$_2$; 5.04 and 5.31 [AB]: O—CH$_2$—C$_6$H$_9$; 7.77: and 7.25 to 7.50 (m) CH$_2$—C$_6$H$_5$ and OC—C$_6$H$_5$.

IR (CHCl$_3$): 1735; 1612, 1575, 1496 cm$^{-1}$

Example 24

3-benzoyl-1,3-diazabicyclo[2,2,2]octan-2-one

Under a nitrogen atmosphere, 2.4 g (10 mmoles) of N-(4-piperidinyl)-benzamide hydrochloride (described in J. Med. Chem. IN. 17(1974), 736-739), with molecular formula $C_{12}H_{16}N_2O$ are dissolved in 30 ml of dichloromethane.

The reaction medium is cooled down to 0° C., 2.8 ml of TEA and 0.66 ml of diphosgene are added.

After a few minutes, the reaction medium is diluted with dichloromethane, then washed with a 10% aqueous solution of tartaric acid, then with water. The organic phase is decanted, dried over magnesium sulphate and the solvent is evaporated off under reduced pressure. The residue is purified on silica eluting with a dichloromethane/ethyl acetate mixture 90/10.

1.62 g of the chloride of 4-(benzoylamino)-1-piperidinecarboxylic acid, with molecular formula $C_{13}H_{15}ClN_2O_5$ (M=266.5 g) is obtained. The corresponding yield is 61%.

1.21 g (48 mmoles) of the compound obtained previously is dissolved under a nitrogen atmosphere in 37 ml of tetrahydrofuran.

The solution is cooled down to −78° C., then 5 ml of a 1M solution of lithium bis(trimethylsilyl) amide in tetrahydrofuran is added dropwise.

The reaction medium is maintained at −78° C. for 15 minutes then the temperature is left to rise to ambient temperature and left to react again for an hour.

The solution is cooled down to 0° C., 720 µl of acetic acid is added. A precipitate forms. Dilution with ethyl acetate followed by washing with a 10% aqueous solution of tartaric acid and with a phosphate buffer solution at pH=7.0.

The organic phase is decanted and dried over magnesium sulphate. Filtration is carried out, then the solvent is evaporated off under reduced pressure. The crude product is purified by chromatography on silica eluting with a dichloromethane and ethyl acetate mixture 90/10.

In this way 0.214 g of expected compound, with formula $C_{18}H_{14}N_2O_2$ (M=230 g) is obtained crystallized from ethyl ether.

The corresponding yield is 20%.

NMR Spectrum of the Proton

In DMSO, at 250 MHz, chemical shifts of the peaks in ppm and multiplicity:

1.71 to 2.02 (m) (CH$_2$)$_2$—CHN; 3.14 (t): N—(CH$_2$)$_2$; 4.84 (m): (CH$_2$)$_2$—CHN; 7.39 to 7.65 (m): C$_6$H$_5$.

IR (CHCl$_3$): 1735, 1682; 1618, 1602, 1582; 1488 cm$^{-1}$.

MS (positive electrospray) m/z: $[2M+Na]^+$=483; $[M+Na+CH_3CN]^+$=294; $[M+Na]^+$=253

Example 25 diphenylmethyl trans-7-oxo-6-oxa-1-azabicyclo[3,2,1] octane-2-carboxylate 15 ml of dichloromethane and 197 mg (0.633 mmole) of diphenylmethyl trans-5-hydroxy-2-piperidinecarboxylate (described in Rec. Trav. Chim. (1959), 78, 648-658), with molecular formula $C_{19}H_{21}NO_3$ are mixed together under an inert atmosphere.

The reaction medium is cooled down to 0° C., then 42 µl of diphosgene, 177 µl of TEA then 77 mg of DMAP are added successively.

The reaction medium is left to react for 4 hours at ambient temperature.

Followed by washing with a 10% aqueous solution of tartaric acid, then with a saturated aqueous solution of sodium chloride.

The organic phases are combined and dried over magnesium sulphate, the solvent is evaporated off under reduced pressure and 195 mg of crude product is thus obtained which is purified by chromatography on silica, eluting with dichloromethane containing 0.1% water.

An oil is recovered which crystallizes from a pentane/ethyl ether mixture.

In this way 108 mg of the expected compound is recovered in the form of white crystals corresponding to the molecular formula $C_{20}H_{19}NO_4$ (M=337.338 g).

The corresponding yield is 51%.

NMR Spectrum of the Proton

In $CDCl_3$, at 400 MHz, chemical shifts of the peaks in ppm and multiplicity:

1.86 (m) and 2.03 (m): N—CH—$CH_2$—$CH_2$—CO; 2.27 (m): N—CH—$CH_2$—$CH_2$—CO; 3.07 (d) and 3.29 (m): N—$CH_2$—CHO; 4.31 (dd): N—CH—$CH_2$; 4.73 (m): N—CH$_2$—CHO; 6.93 (s): $CO_2$—CH—$(C_6H_5)_2$; 7.27 to 7.41 (m): $\underline{CH}(C_6H_5)_2$;

IR ($\overline{CH}Cl_3$): 1788, 1736; 1496 cm$^{-1}$;

MS (SIMS) m/z: $[M+Na]^+$360, $[M+Na]^+$344; $[M]^+$=337, 167

Example 26a (4-nitrophenyl)methyl trans-7-oxo-6-oxa-1-azabicyclo [3,2,1]octane-2-carboxylate 66 ml of dichloromethane and 1 g (3.56 mmole) of (4-nitrophenyl)methyl trans-5-hydroxy-2-piperidine carboxylate with molecular formula $C_{13}H_{16}N_2O_5$ (M=280.282 g) are mixed together under an inert atmosphere.

The reaction medium is cooled down to 0° C., and 0.24 ml of diphosgene is added. The reaction medium is left to react whilst agitating for 10 minutes at 0° C., then left to warm up to ambient temperature. The solvent is evaporated off under reduced pressure.

The residue is dissolved in 66 ml of toluene and 0.99 ml of TEA is added.

The flask is immersed in an oil bath at 110° C. and kept there for 15 minutes. It is then left to return to ambient temperature.

The reaction medium is washed with a 10% aqueous solution of tartaric acid, then with a saturated aqueous solution of sodium chloride.

The organic phase is dried over magnesium sulphate then the solvent is evaporated off under reduced pressure.

In this way 0.885 g of crude product is obtained which is purified by chromatography on silica eluting with a toluene/ethyl acetate mixture 85/15.

In this way 0.184 g of expected compound, with molecular formula $C_{14}H_{14}N_2O_6$ (M=306.276 g) is recovered in the form of a yellow oil.

The corresponding yield is 17%.

NMR Spectrum of the Proton

In $CDCl_{13}$, at 400 MHz, chemical shifts of the peaks in ppm and multiplicity:

1.92 (m) and 2.07 (m): N—CH—$CH_2$—$CH_2$—CO; 2.22 (m) and 2.30 (m): N—CH—$CH_2$—$CH_2$—CO; 3.17 (d) and 3.35 (dm): N—$CH_2$—CHO; 4.28 (dd): N—CH—$CH_2$; 4.79 (m): N—$CH_2$—$\overline{CH}O$; 5.33 [AB]: $CO_2$—$CH_2$—$C_6H_4NO_2$; 7.56 and 8.25 [AA'BB']: $CH_2$—$C_6H_4$—$NO_2$ IR ($CHCl_3$): 1791, 1745; 1609, 1526, 1495 cm$^{-1}$;

MS (EI) m/z: $[M]^+$=306, 262, 136, 126, 82, 55

Example 26b trans-7-oxo-6-oxa-1-azabicyclo[3,2,1,]octane-2 carboxylic acid 140 mg (0.457 mmole) of the ester obtained in Example 26a, 7 ml of acetone and 28 mg of Pd/C catalyst at 20% by weight are mixed together.

The reaction medium is then left to react for 25 minutes under agitation and a hydrogen atmosphere at normal pressure.

The catalyst is filtered out and the solvent is then evaporated off under reduced pressure.

In this way 137 mg of the expected compound, with molecular formula $C_7H_9NO_4$ (M=171.152 g), is obtained in the form of an oil, mixed with one mole of p-toluidine.

The corresponding yield is 97%.

NMR Spectrum of the Proton

In DMSO, at 400 MHz, chemical shifts of the peaks in ppm and multiplicity:

1.84 (m) and 1.95 to 2.05 (m): N—CH—$CH_2$—$CH_2$—CO; 3.13 (d) and 3.24 (dd): N—$CH_2$—CHO; 4.02 (dd): N—CH—$CH_2$; 4.81 (dm): N—$CH_2$—$\underline{CH}O$.

Example 26c methyl trans-7-oxo-6-oxa-1-azabicyclo[3,2,1]octane-2-carboxylate 17.25 mg (0.1 mmole) of the acid obtained in Example 26b is dissolved in 3 ml of dichloromethane.

The reaction medium is treated with an excess of diazomethane in solution in dichloromethane, then the solvent is evaporated off under reduced pressure.

30 mg of crude product is thus obtained which is purified by chromatography on silica, eluting with a toluene/ethyl acetate mixture 90/10.

6.7 mg of the expected compound (M=485.187 g) is recovered.

The corresponding yield is 36%.

Example 27

(4-nitrophenyl)methyl cis-7-oxo-6-oxa-1-azabicyclo [3,2,1]octane-2-carboxylate 0.802 g (2.034 mmoles) of (4-nitrophenyl)methyl cis-5-hydroxy-2-piperidine-carboxylate trifluoroacetate (described in Rec. Trav. Chim. (1959), 78, 648-658), with molecular formula $C_{13}H_{16}N_2O_5$, $CF_3CO_2H$ (M=394.303 g) is introduced under a nitrogen atmosphere into 40 ml of dichloromethane is introduced followed by cooling to 0° C. 0.135 ml of diphosgene is added. The reaction medium is agitated for 15 minutes at 0° C., then the temperature is left to rise to ambient temperature and agitation is continued for 35 minutes.

The solvent is evaporated off under reduced pressure.

This product is dissolved in 40 ml of toluene and 1.1 ml of triethylamine. The reaction mixture is taken to 100° C. for 35 minutes, then left to cool down to ambient temperature.

The reaction medium is washed with water then with a phosphate buffer solution at pH=7.

The organic phase is dried over sodium sulphate and the solvent is evaporated off under reduced pressure.

0.56 g of a crude product is thus obtained which is purified by chromatography on silica, eluting with a dichloromethane/acetone mixture 95/5.

In this way 110 mg of the expected compound, with molecular formula $C_{14}H_{14}N_2O_6$, (M=306.275 g), is recovered in the form of an oil.

The corresponding yield is 17%.

NMR Spectrum of the Proton

In $CDCl_3$, at 300 MHz, chemical shifts of the peaks in ppm and multiplicity:

1.80 to 1.94 and 2.10 to 2.45: N—CH—CH$_2$—CH$_2$—CO; 3.07 (d), 3.04 (dm) and 3.86 (dd): CH—N—CH$_2$; 4.80 (t): O═C—O—CH; 5.28 and 5.43 [AB]: O═C—O—C H$_2$—C$_6$H$_5$; 7.61 and 8.24 [AA'BB'] C$_6$H$_4$NO$_2$.

IR (CHCl$_3$): 1801, 1794, 1745, 1704, 1609, 1525, 1498 cm$^{-1}$. MS (EI) m/z: [M]$^+$=306, 262, 136, 126, 83, 55

Example 28a 1-propenyltriphenylphosphonium salt of phenylmethyl trans-7-oxo-6-(sulphooxy)-1,6-diazabicyclo[3,2,1]octane-2-carboxylate Stage A
phenylmethyl cis-5-hydroxy-1-(trifluoroacetyl-2-piperidine carboxylate 6.19 g (22.77 mmoles) of the hydrochloride of phenylmethyl 5-hydroxy-2-piperidinecarboxylate with molecular formula $C_{13}H_{18}ClNO_3$ (M=271.746 g) (described in Rec. Trav. Chim. (1959), 78, 648-658) is dissolved under an inert atmosphere in 80 ml of anhydrous dichloromethane.

The reaction medium is cooled down to 5° C. and 9.5 ml of TEA is added then, 6.46 ml of trifluoroacetic anhydride is added dropwise.

The reaction medium is left to react under agitation at 5° C. for one hour, then diluted with dichloromethane, washed successively with a 10% solution of tartaric acid, an aqueous phosphate buffer solution at pH=7 and an aqueous solution of sodium chloride.

The organic phase is decanted and dried over magnesium sulphate. Then the solvent is evaporated off under reduced pressure.

10 g of a red oil is thus obtained which is dissolved in 100 ml of methanol. The reaction medium is cooled down to about 10° C., and 6.8 g (78 mmoles) of sodium hydrogen carbonate in solution in 100 ml of water is added slowly, at a maximum of 20° C.

The reaction medium is left to react under agitation at 20° C. for 30 minutes, and extracted with dichloromethane.

The organic phase is decanted, washed with a saturated aqueous solution of sodium chloride and dried over magnesium sulphate.

The solvent is evaporated off under reduced pressure and 7.6 g of an orange oil is thus recovered which is purified by chromatography on silica, eluting with a dichloromethane/ethyl acetate mixture 95/5.

In this way 6 g of expected compound with molecular formula $C_{15}H_{16}F_3NO_4$ (M=331.294 g) is recovered. The corresponding yield is 68%.

Stage B
phenylmethyl trans-5-[(2-propenyloxy)amino]-1-(trifluoroacetyl)-2-piperidinecarboxylate, 1.74 g (5.26 mmoles) of the alcohol obtained previously is introduced into 29 ml of acetonitrile. The reaction medium is cooled down to −40° C. and 0.61 ml of 2,6-lutidine ($C_5H_3N$ $(CH_3)_2$) then 0.91 ml of trifluoro methanesulphonic anhydride are added at this temperature.

The reaction medium is left to react under agitation for 30 minutes at −40° C. Then, still at −40° C., 0.7 ml (10.52 mmoles) of 0-allyl-hydroxylamine is added over one minute.

The reaction medium is left to return to 0° C. then 0.61 ml of 2,6 lutidine is added and left to react overnight (15 hours), at approximately 5° C., then for another 2 hours at 20° C.

The reaction medium is then diluted with dichloromethane, washed with an aqueous solution of sodium hydrogen carbonate, then a 10% aqueous solution of tartaric acid and a saturated aqueous solution of sodium chloride.

The organic phase is decanted, dried over magnesium sulphate and the solvent is evaporated off under reduced pressure.

2.1 g of a yellow oil is thus obtained which is purified by chromatography on silica, eluting with a toluene/ethyl acetate mixture 90/10.

1.23 g of expected compound with molecular formula $C_{18}H_{21}F_3N_2O_4$ (M=386.374 g) is recovered.

The corresponding yield is 61%.

Stage C
phenylmethyl trans-5-[(2-propenyloxy)amino]-2-piperidinecarboxylate 1.41 g (3.65 mmoles) of compound obtained previously is dissolved under an inert atmosphere in 25 of anhydrous methanol.

The reaction medium is cooled down to 0-5° C., then 3 additions are made, at 45 minutes intervals, of 145 mg of NaBH$_4$.

The reaction medium is then acidified to pH=2 with a 1N aqueous solution of hydrochloric acid previously cooled to 5° C.

Extraction is carried out with ethyl acetate.

The aqueous phase is cooled down to 5° C., 100 ml of ethyl acetate is added, followed by treatment with a saturated solution of sodium carbonate until a pH of 8.5 to 9 is obtained.

The amine is then extracted with ethyl acetate. The organic phase is washed with a saturated aqueous solution of sodium chloride, then dried over magnesium sulphate and concentrated by evaporation of the solvent under reduced pressure.

In this way 0.628 g of expected product with molecular formula $C_{16}H_{22}N_2O_3$ (M=290.364 g) is obtained.

The corresponding yield is 59%.

Stage D phenylmethyl trans-7-oxo-6-(2-propenyloxy)-1,6-diazabicyclo[3,2,1]octane-2-carboxylate 103 mg (0.35 mmoles) of the amine obtained previously is dissolved under an inert atmosphere in 35 ml of anhydrous dichloromethane.

The solution is cooled down to about 0-5° C., and 0.1 ml of TEA, then 21 μl of diphosgene are added dropwise at this temperature.

The reaction medium is left to react under agitation for 15 minutes at 0-5° C., then the temperature is left to rise to 20° C., and 42 mg of DMAP is added. Agitation is continued at 20° C. for approximately 5 hours.

The reaction medium is diluted with dichloromethane, washed with a 10% aqueous solution of tartaric acid, then with water.

The organic phase is dried over magnesium sulphate and concentrated by evaporation of the solvent under reduced pressure.

In this way 70 mg of crude product is obtained which is purified by chromatography on 5 g of silica, eluting with a dichloromethane/methanol mixture 98/2.

48 mg of expected product of formula $C_{17}H_{20}N_2O_4$ (M=316.36 g) is recovered.

The corresponding yield is 43%.

IR ($CHCl_3$): 1750; 1642; 1600, 1496 cm$^{-1}$.

MS (positive electrospray) m/z: [M+Na+$CH_3$CN]$^+$=380; [M+Na]$^+$=339; [M+H]$^+$=317.

Stage E 1-propenyltriphenylphosphonium salt of phenylmethyl trans-7-oxo-6-(sulphooxy)-1,6-diazabicyclo [3,2,1] octane-2-carboxylate 202 mg (0.638 mmoles) of the compound obtained in stage D is dissolved under an inert atmosphere in 5.5 ml of anhydrous dichloromethane.

73 μl of acetic acid, then 369 mg of $Pd(P(C_6H_5)_3)_4$ is added at 20° C. to the solution obtained.

After agitation for 30 minutes at ambient temperature, N-hydroxy-urea, formed by 5.5 ml of pyridine and 358 mg of the $SO_3$-pyridine complex is treated.

The reaction medium is left to react under agitation for 18 hours at 20° C., then the reaction medium is concentrated by evaporation of the solvent under reduced pressure.

The reaction medium is taken up with 50 ml of dichloromethane and washed with water. The organic phase is dried over magnesium sulphate and the dichloromethane is evaporated off under reduced pressure.

650 mg of crude product is thus obtained which is purified by chromatography on silica, eluting with a dichloromethane/acetone mixture 60/40 containing 0.1% by volume of TEA.

In this way 280 mg of the phosphonium salt of the expected compound, with molecular formula $C_{35}H_{35}N_2O_7PS$ (M=646.705 g) is recovered.

The corresponding yield is 68%.

NMR Spectrum of the Proton

In $CDCl_3$, at 300 MHz, chemical shifts of the peaks in ppm and multiplicity:

2.05 (m), 2.22 (dm) and 2.33 (m): N—CH—$CH_2$—$CH_2$; 2.95 (d) and 3.30 (dt): O=C—N—$CH_2$; 4.10 ($\overline{m}$) and $\overline{4.32}$ (m): O=C—N—CH and O=C—N=$CH_2$—CH; 5.12(s): COO—$CH_2$—$C_6\overline{H_5}$; 7.36: $C_6\overline{H_5}$; and $\overline{2.30}$ (m): $CH_3$—$\overline{CH=CH}$; 6.65 and 7.20 $C\overline{H_3}$—$\underline{CH=CH}$; 7.65-7.85 $\overline{P(C_6H_5)_3}$.

IR ($CHCl_3$): 1746; 1638, 1605, 1587, 1495 cm$^{-1}$.

MS (negative and positive electrospray) m/z: [Manion]$^-$=355; [Mcation]$^+$=303.

Example 28b

Sodium salt of phenylmethyl trans-7-oxo-6-(sulphooxy)-1,6-diazabicyclo [3,2,1] octane-2-carboxylate 236 mg (0.364 mmoles) of the phosphonium salt obtained in stage E of Example 28a is dissolved in 0.8 ml of tetrahydrofuran and 4 drops of water.

The solution obtained is passed over a column DOWEX 50WX8 resin in Na+ form, eluting with water.

After lyophilization, 127 mg of the expected sodium salt, with molecular formula $C_{14}H_{15}N_2O_7SNa$ (M=378.339 g) is obtained.

The corresponding yield is 92%.

NMR Spectrum of the Proton

In DMSO, at 300 MHz, chemical shifts of the peaks in ppm and multiplicity:

1.65 to 2.02: N—CH—$CH_2$—$CH_2$; 2.91 (d) and 3.04 (dt): O=C—N—$CH_2$; 4.00 to $4.\overline{05}$: O=$\overline{C}$—N—CH and O=C—N—$CH_2$—$\underline{CH}$; 5.20 [AB]: COO—$CH_2$—$C_6\underline{H_5}$; 7.39 (m): $C_6H_5$.

$\overline{IR}$ (Nujol): 1744; 1495 cm$^{-1}$.

MS (electrospray negative) m/z; [M]$^-$=355.

Example 28c phenylmethyl trans-7-oxo-6-[(phenylsulphonyl)oxy]-1,6-diazabicyclo [3,2,1] octane-2-carboxylate 48 mg (0.152 mmoles) of the derivative obtained in stage D of Example 28a is dissolved in 1.2 ml of dichloromethane.

26 μl of acetic acid then 88 mg of Pd $(PPh_3)_4$ are added to it at 20° C., and left to react for 2 hours at 20° C. under agitation.

The reaction medium is diluted by adding toluene and the solvents are evaporated off under reduced pressure.

1.5 ml of dichloromethane, 25 μl of pyridine and 24 μl of benzenesulphonyl chloride are added to the crude product obtained.

The reaction medium is left to react at 20° C. under agitation for 1 hour then 12.5 μl of pyridine and 10 μl of benzenesulphonyl chloride are added.

The reaction medium is agitated for 15 minutes at 20° C. and diluted with dichloromethane.

The reaction medium is then washed successively with a 10% aqueous solution of tartaric acid, a phosphate buffer solution at pH=7 and a saturated aqueous solution of sodium chloride.

The aqueous phase is dried over magnesium sulphate, and the solvent is evaporated off under reduced pressure. 180 mg of a yellow oil is obtained which is purified by chromatography on silica, eluting with a dichloromethane/methyl and t-butyl ether mixture 95/5.

In this way 20 mg of the expected compound, with molecular formula $C_{20}H_{20}N_2O_6S$ (M=416.456 g) is recovered. The corresponding yield is 31%.

NMR Spectrum of the Proton

In $CDCl_3$, at 300 MHz, chemical shifts of the peaks in ppm and multiplicity:

1.83 (m) and 2.00 to 2.25 (m): N—CH—$CH_2$—$CH_2$; 3.02 (d) and 3.16 (dm): O=C—N—$CH_2$; 4.04 ($\overline{m}$) and $\overline{4.11}$ (dd):

O=C—N—CH and O=C—N—CH$_2$—CH; 5.21 (s): COO—CH$_2$—C$_6$H$_5$; 7.34 (m): C$_6$H$_5$; 7.56 (m), 7.70 (m) and 8.03 (m): O$_2$S—C$_6$H$_5$.

IR (CHCl$_3$): 1780, 1738; 1600, 1585, 1498; 1386, 1193 cm$^{-1}$. MS (positive electrospray) m/z: [2M+Na]$^+$855; [M+Na+CH$_3$CH]$^+$=480; [M+Na]$^+$=439; [MH]$^+$=417.

Example 28d phenylmethyl trans-7-oxo-6-[(2-thienylsulphonyl)oxy]-1,6-diazabicyclo [3,2,1] octane-2-carboxylate Starting with 100 mg (0.316 mmoles) of the compound obtained in stage D of Example 28a, the process is carried out in a similar manner to the one which has just been described, except that instead of using benzenesulphonyl chloride, 2 thienyl sulphonyl chloride is used.

8 mg of expected compound, with molecular formula C$_{18}$H$_{18}$N$_2$O$_6$S$_2$ (M=422.481 g) is thus recovered. The corresponding yield is 30%.

NMR Spectrum of the Proton
In CDCl$_3$, at 300 MHz, chemical shifts of the peaks in ppm and multiplicity:

1.84 (m) and 2.10 to 2.25: N—CH—CH$_2$—CH$_2$; 3.02 (d) and 3.24 (dt): O=C—N—CH$_2$; 4.06 (m): O=C—N—CH$_2$—CH; 4.14 (dd): O=C—N—CH; 5.22 (s): COO—CH$_2$—C$_6$H$_5$; 7.17 (dd): SO$_3$—C—S—CH=CH; 7.35 (bs): C$_6$H$_5$; 7.80 (dd): SO$_3$—C=CH; 7.87 (m): SO$_3$—C—S—CH.

IR (CHCl$_3$): 1780, 1739; 1600, 1503, 1495 cm$^{-1}$.

MS (positive electrospray) m/z: [M+Na+CH$_3$CN]$^+$=867; [2M+Na]$^+$=445; 339, 298, 91.

Example 28e phenylmethyl trans-6-(2-hydroxy-2-oxoethoxy)-7-oxo-1,6-diazabicyclo [3,2,1]octane-2-carboxylate Stage A
phenylmethyl trans-7-oxo-6-[2-oxo-2-(2-propenyloxy)ethoxy]-1,6-diazabicyclo[3,2,1]octane-2-carboxylate 48 mg (0.15 mmoles) of the compound obtained in stage D of Example 28a is dissolved under an inert atmosphere in 1.5 ml of anhydrous dichloromethane.

18 µl of acetic acid then 88 mg of Pd(P(C$_6$H$_5$)3)4 is added at 20° C. and left under agitation for 1 hour at 20° C.

The reaction medium is filtered over silica, eluting with a dichloromethane/ether t-butyl and methyl mixture 7/3.

The solvent is evaporated off under reduced pressure and 70 mg of hydroxy urea is obtained which is taken up in 2 ml of dichloromethane, then 85 µl of TEA and 64 µl of allyl bromo-acetate are added.

The reaction medium is agitated at 20° C. for 3 and a half hours.

The reaction medium is washed successively with a 10% aqueous solution of tartaric acid, an aqueous phosphate buffer solution at pH=7, and water.

The organic phase is dried and the solvent is evaporated off under reduced pressure.

60 mg of crude product is thus obtained which is chromatographed on silica eluting with a dichloromethane/t-butyl and methyl ether mixture 90/10 containing 0.1% TEA.

22 mg with molecular formula C$_{19}$H$_{22}$N$_2$O$_6$, (M=374.396 g) is recovered. The corresponding yield is 39%.

Stage B
phenylmethyl trans-6-(2-hydroxy-2-oxoethoxy)-7-oxo-1,6-diazabicyclo [3,2,1] octane-2-carboxylate 22 mg (0.0587 mmoles) of the compound obtained previously is dissolved under an inert atmosphere in 1 ml of anhydrous dichloromethane.

10 µl of acetic acid and 34 mg of Pd(P(C$_6$H$_5$)$_3$)$_4$ are added and left to react under agitation at 20° C. for 30 minutes.

The reaction medium is concentrated and taken up in toluene in order to eliminate the acetic acid.

In this way 49 mg of crude product is obtained to which 2 ml of phosphate buffer at pH 7 is added, then washed twice with 1 ml of dichloromethane.

The solvent is evaporated off and 46 mg of crude product is obtained which is purified by chromatography on silica, eluting firstly with a dichloromethane/t-butyl and methyl ether mixture 90/10 then with a dichloromethane/ethanol mixture 60/40.

In this way 4.5 mg of the expected compound, with molecular formula C$_{37}$H$_{37}$N$_2$O$_6$P (M=636.691 g) is obtained. The corresponding yield is 12%.

Example 29a (4-nitrophenyl) methyl trans-6-benzoyl-7-oxo-1,6-diazabicyclo[3,2,1]octane-2-carboxylate Stage A
1-(1,1-dimethylethyl) and 2-[(4-nitrophenyl)methyl]cis-5-(methylsulphonyl)oxy-1,2-piperidinedicarboxylate 11.25 g (29.5 mmoles) of 1-(1,1-dimethylethyl) and 2-[(4-nitrophenyl)methyl] cis-5-hydroxy-1,2-piperidine dicarboxylate (described in Rec. Trav. Chim. (1959), 78, 648-658), with molecular formula C$_{18}$H$_{24}$N$_2$O$_7$ (M=380.398 g) is dissolved under an inert atmosphere in 112 ml of dichloromethane.

The reaction medium is cooled down to 0-5° C., then 5 ml of TEA then 2.44 ml of methanesulphonyl chloride are introduced successively.

The temperature is left to return to 20° C. under agitation and the medium is left to react for 1 hour. The reaction medium is then diluted with dichloromethane, washed twice with water, dried over sodium sulphate, and the solvent is evaporated off under reduced pressure.

16 g of a crude oil is thus obtained which is purified by chromatography on silica, eluting with dichloromethane containing 2% ethyl acetate.

9.14 g of expected product with molecular formula C$_1$H$_{26}$N$_2$O$_9$S (M=458.491 g) is recovered. The corresponding yield is 67%.

Stage B
1-(1,1-dimethylethyl) and 2-[(4-nitrophenyl) methyl] trans-5-azido-1,2-piperidinedicarboxylate 11.1 g (24.2 mmoles) of the mesylate obtained previously is dissolved under an inert atmosphere in 111 ml of dimethylformamide.

1.73 g of sodium nitride NaN$_3$ is then added.

The reaction medium is heated under agitation at 80° C. and kept at this temperature for 18 hours. It is left to return to 20° C., then the dimethylformamide is evaporated off under reduced pressure until a small volume is obtained, then diluted with ethyl acetate and washed with a 2 N soda solution, then with water. The reaction medium is dried over magnesium sulphate, then the solvents are evaporated off under reduced pressure.

The crude oil obtained is purified by chromatography on silica eluting with dichloromethane containing 2% ethyl acetate.

7.34 g of expected compound, with molecular formula $C_{18}H_{23}N_5O_6$ (M=405.413 g) is thus obtained in the form of a yellow oil which crystallizes.

The corresponding yield is 75%.

Stage C 1-(1,1-dimethyl-ethyl) and 2-[(4-nitrophenyl) methyl] trans-5-amino-1,2-piperidinedicarboxylate 7.34 g (18.1 mmoles) of the azide obtained previously is introduced into 150 ml of tetrahydrofuran and 30 ml of water.

7.2 g of triphenylphosphine is added, then left to react under agitation at 20° C. overnight.

The solvent is then evaporated off under reduced pressure and two entrainments with ethyl acetate are carried out.

In this way a dry extract is obtained which is purified by chromatography on silica, eluting with dichloromethane containing 5% methanol.

5.62 g of expected compound, with molecular formula $C_{18}H_{25}N_3O_6$ (M=379.416 g) is recovered. The corresponding yield is 82%.

Stage D 1-(1,1-dimethylethyl) and 2-[(4-nitrophenyl)methyl] trans-5-(benzoylamino)-1,2-piperidinedicarboxylate 700 mg (1.84 mmole) of the amine obtained previously is dissolved in 8 ml of dichloromethane.

The reaction medium is cooled down to 0° C., then 257 µl of TEA then 214 µl of benzoyl chloride is introduced.

The temperature is left to return to 20° C.

After reaction for 40 minutes, the reaction medium is diluted with dichloromethane, washed with a saturated solution of sodium hydrogen carbonate, then water.

Followed by drying over sodium sulphate, and the solvent is evaporated off under reduced pressure.

867 mg of expected compound, with molecular formula $C_{25}H_{29}N_3O_7$ (M=483.525 g) is thus obtained. The corresponding yield is 97%.

Stage E (4-nitrophenyl) methyl trans 5-(benzoylamino)-2-piperidine carboxylate hydrochloride 861 mg (8 mmole) of the amide obtained previously, 9 ml of methanol, and 2.3 ml of a solution of gaseous hydrogen chloride at 8 mol/l in methanol are mixed together.

The temperature is left to return to 20° C. and left to react over 3 hours. 1.15 ml of hydrogen chloride solution in methanol is then added.

The reaction medium is agitated for 20 minutes at 20° C., then the solvent is evaporated off under reduced pressure.

Two entrainments with dichloromethane, then two entrainments with ethyl ether are carried out.

The product crystallizes from ethyl ether.

In this way 715 mg of expected compound with molecular formula $C_{20}H_{22}ClN_3O_5$ (M=419.967 g) is obtained.

The corresponding yield is 96%.

Stage F (4-nitrophenyl)methyl trans-5-(benzoylamino)-1-(chlorocarbonyl)-2-piperidine carboxylate 1.08 g (2.58 mmole) of the hydrochloride obtained as previously and 11 ml of dichloromethane are mixed together.

The suspension obtained is cooled down to about 0-5° C. and 791 µl of TEA is added, then, 161 µl of diphosgene is then added to the solution obtained.

The reaction medium is agitated for 5 minutes at 0-5° C., then left to return to 20° C., and left under agitation for another 30 minutes.

The reaction medium is then diluted with dichloromethane, washed with a 10% aqueous solution of tartaric acid, then water.

Followed by drying over sodium sulphate and the solvent is evaporated off under reduced pressure.

The crude product is purified by chromatography on silica eluting with dichloromethane containing 5% acetone.

969 mg of expected compound with molecular formula $C_{21}H_{20}ClN_3O_6$ (M=445.862 g) is recovered.

The corresponding yield is 84%.

Stage G (4-nitro-phenyl) methyl trans-6-benzoyl-7-oxo-1,6-diazabicyclo[3,2,1]octane-2-carboxylate 928 mg (2.08 mmoles) of the compound obtained previously and 27 ml of tetrahydrofuran are mixed together under an inert gas.

The solution obtained is cooled down to −78° C. under agitation, then 2.1 ml of a 1M solution of lithium bis (trimethylsilyl) amide in tetrahydrofuran is introduced.

The reaction medium is left under agitation for 10 minutes to −78° C. then 130 µl of acetic acid is added and agitation is carried out whilst leaving the temperature to rise to 15° C.

The reaction medium is diluted with ethyl acetate then washed successively with a 10% aqueous solution of tartaric acid, with a phosphate buffer solution at pH=7 and water.

Followed by drying over magnesium sulphate and the solvent is evaporated off under reduced pressure.

1.6 g of a dry extract is thus obtained which is purified by chromatography on silica eluting with a dichloromethane/acetone mixture 98/2.

The product is then crystallized from ethyl ether in order to produce 204 mg of the expected compound, with molecular formula $C_{21}H_{19}N_3O_6$ (M=409.441 g).

The corresponding yield is 24%.

NMR Spectrum of the Proton

In CDCl$_3$, at 250 MHz, chemical shifts of the peaks in ppm and multiplicity:

1.98 (m), 2.22 (m) and 2.40 (m): N—CH—CH$_2$—CH$_2$; 3.08 (d) and 3.42 (dt): O=C—N—CH$_2$; 4.23 (dd): O=C—N—CH; 4.53 (m): O=C—N—CH$_2$—CH; 5.34 [AB]: COO—CH$_2$—C$_6$H$_5$; 7.69 (m): 8.25 (m): 7.44 (m) and 7.56 (m): C$_6$H$_5$ and C$_6$H$_4$NO$_2$.

IR (CHCl$_3$): 1763, 1744, 1676; 1609, 1603, 1583, 1526, 1492 cm$^{-1}$.

MS (EI) m/z: [M]$^+$=409, 304, 273, 201, 105, 77.

Example 29b trans-6-benzoyl-7-oxo-1,6-diazabicyclo[3,2,1]octane-2-carboxylic acid 89 mg of the ester obtained in Example 29a, 4 ml of acetone and 6 mg of 10% Pd/C catalyst are mixed together.

The reaction medium is left to react under agitation, at 20° C. and under a hydrogen atmosphere for 2 hours 45 minutes, then the catalyst is filtered out and the filtrate is evaporated under reduced pressure.

In this way 88 mg of a resin is obtained which crystallizes from 0.5 ml of ethyl ether.

In this way 54 mg of the expected compound, with molecular formula $C_{14}H_{14}N_2O_4$ (M=274.278 g) is obtained. The corresponding yield is 91%.

NMR Spectrum of the Proton

In CDCl$_3$, at 250 MHz, chemical shifts of the peaks in ppm and multiplicity:

1.96 (m), 2.10 (m) and 2.37 (m): N—CH—CH$_2$—CH$_2$; 3.13 (d) and 3.41 (dm): O=C—N—CH$_2$; 4.10 (bd): O=C—

N—CH; 4.52 (m): O=C—N—CH$_2$—CH; 7.44 (m): 7.56 (tt) and 7.69 (dd) C$_6$H$_5$. MS (EI) m/z: M$^+$=274, 229, 169, 105, 77.

Example 29c methyl trans-6-benzoyl-7-oxo-1,6-diazabicyclo[3,2,1]octane-2-carboxylate 2 ml of a solution of diazomethane at 12.7 g/l in dichloromethane is added under agitation to 28 mg (0.102 mmole) of the acid obtained in Example 29b.

The solvent is evaporated off under reduced pressure and the residue is purified by chromatography on silica eluting with a dichloromethane/ethyl acetate mixture 98/2.

18.4 mg of expected compound, with molecular formula C$_{15}$H$_{16}$N$_2$O$_4$ (M=288.305 g) is recovered. The corresponding yield is 63%.

NMR Spectrum of the Proton

In CDCl$_3$, at 300 MHz, chemical shifts of the peaks in ppm and multiplicity:

1.90 to 2.42: N—CH—CH$_2$—CH$_2$; 3.12 (d) and 3.44 (dt): O=C—N—CH$_2$; 3.83 (s): CH$_3$; 4.17 (dl): O=C—N—CH; 4.54 (m): O=C—N—CH$_2$—CH; 7.44 (t), 7.56 (t) and 7.69 (d): C$_6$H$_5$.

MS (EI) m/z: [M]$^+$=288, 229, 183, 155, 105, 77.

Example 29d trans-6-benzoyl-7-oxo-N-(phenylmethyl)-1,6-diazabicyclo [3,2,1] octane-2-carboxamide 30 mg (0.109 mmole) of trans-6-benzoyl-7-oxo-1,6-diazabicyclo[3,2,1]octane-2-carboxylic acid obtained in Example 29b, 0.5 ml of dichloromethane, 23 mg of EDCI and 13 µl of benzylamine are mixed together.

The reaction medium is left to react for 30 minutes under agitation. It is then diluted with dichloromethane, washed with a 10% aqueous solution of tartaric acid, decanted, and the organic phase is dried over sodium sulphate.

The solvent is evaporated off under reduced pressure in order to obtain a crude product which is purified by chromatography on silica eluting with a dichloromethane/acetone mixture 98/2.

In this way 19.5 mg of the expected compound, with molecular formula C$_{21}$H$_{21}$N$_3$O$_3$ (M=363.419 g) is obtained. The corresponding yield is 49%.

NMR Spectrum of the Proton

In CDCl$_3$, at 300 MHz, chemical shifts of the peaks in ppm and multiplicity:

1.97 (m), 2.34 (m) and 2.59 (m): N—CH—CH$_2$—CH$_2$; 2.90 (d), 3.33 (m), 3.99 (bd) and 4.50 (m): O=C—N—CH, O=C—N—CH$_2$—CH, O=C—N—CH$_2$, CO—NH—CH$_2$—C$_6$H$_5$; 6.94 (bt): NH; 7.24 to 7.58 (m) and 7.68 (m): C$_6$H$_5$—CO and C$_6$H$_5$—CH$_2$.

IR (CHCl$_3$): 3411, 1763, 1680; 1603, 1583, 1519, 1498 cm$^{-1}$.

Example 29e 6-benzoyl-N-[methyl(phenylmethyl)]-7-oxo-1,6-diazabicyclo [3,2,1]octane-2-carboxamide The operation is carried out in a similar manner as Example 29d starting with 50 mg (0.182 mmole) of the acid obtained in Example 29b and 45 µl of N-methyl-benzylamine.

In this way 12 mg of the expected compound, with molecular formula C$_{22}$H$_{23}$N$_3$O$_3$ (M=377.45 g) is recovered. The corresponding yield is 17%.

MS (EI) m/z: [M]$^+$=377, 272, 105.

Example 29f 6-benzoyl-2-(hydroxymethyl)-1,6-diazabicyclo[3,2,1]octan-7-one 100 mg (364 mmole) of trans-6-benzoyl-7-oxo-1,6-diazabicyclo[3,2,1]octane-2-carboxylic acid obtained in Example 29b is dissolved under an inert atmosphere, in 3 ml of tetrahydrofuran.

The reaction medium is cooled down to −10° C. and 40 µl of methylmorpholine, then 38 µl of ethyl chloroformate are added.

The reaction medium is left to react for 15 minutes at −10° C., then the temperature is left to rise to 0° C. and 27 mg of NaBH$_4$ is added, then 1.5 ml of methanol is added dropwise.

The reaction medium is left under agitation at 0° C. for 2 hours then left to return to ambient temperature.

3 ml of water is added, the reaction medium is left under agitation for 15 minutes, then a few drops of ammonium chloride are added. Extraction is carried out with ethyl acetate, followed, by drying over magnesium sulphate, filtering and the solvent is evaporated off under reduced pressure.

In this way 85 mg of a crude product is obtained which is purified by chromatography on silica, eluting with a dichloromethane/methanol mixture 98/2.

In this way 25 mg of expected compound, with molecular formula C$_{14}$H$_{16}$N$_2$O$_3$ (M=260.3 g) is recovered. The corresponding yield is 26%.

NMR Spectrum of the Proton

In CDCl$_3$, at 300 MHz, chemical shifts of the peaks in ppm and multiplicity:

1.61 (m, 1H), 2.00 (m, 2H) 2.30 (m, 1H): CH—CH$_2$—CH$_2$—CH; 2.19: 3.23 (d) and 3.26 (dt): N—CH$_2$; 3.60 (m): N—CH—CH$_2$—OH; 3.70 (m) and 3.77 (dd): CH—CH$_2$—O; 4.56 (m): N—CH—CH$_2$—N.

MS (SIMS) m/z: [M+Na]$^+$=283, [M+H]$^+$=261, [M]$^+$=260, 229, 105.

Example 30

(4-nitrophenyl)methyl trans-6-acetyl-7-oxo-1,6-diazabicyclo[3,2,1]octane-2-carboxylate 1 g (2.63 mmoles) of the product prepared in stage C of Example 29 is dissolved in 12 ml of dichloromethane.

250 µl of acetic anhydride is added, the reaction medium is left to react for 10 minutes under agitation, then diluted with dichloromethane and washed with a saturated aqueous solution of sodium hydrogen carbonate.

The organic phase is dried over sodium sulphate, evaporated to dryness under reduced pressure in order to obtain 1.2 g of 1-(1,1-dimethylethyl) and 2-[(4-nitrophenyl)methyl] trans-S-(acetylamino)-1,2-piperidinedicarboxylate with molecular formula C$_{20}$H$_{27}$N$_3$O$_7$ (M=421.453 g).

This product is used without purification in stages similar to stages E to G of Example 29 and 14 mg of expected compound, with molecular formula C$_{16}$H$_{17}$N$_3$O$_6$ (M=347.330 g) is thus recovered. The corresponding yield is 17%.

NMR Spectrum of the Proton

In CDCl$_3$, at 300 MHz, chemical shifts of the peaks in ppm and multiplicity:

1.87 (m), 2.00 to 2.30 (m): N—CH—CH$_2$—CH$_2$; 2.54 (s): N—CO—CH$_3$; 2.95 (d) and 3.21 (m): O=C—N—CH$_2$; 4.26 (bd): O=C—N—CH; 4.55 (m): O=C—N—CH$_2$—CH; 5.34 [AB]: CO$_2$—CH$_2$—C$_6$H$_4$; 7.57 and 8.25 [AA'BB']: C$_6$H$_4$—NO$_2$ MS (EI) m/z: [M]$^+$=347, 304, 211, 169, 125, 43.

Example 31

(4-nitrophenyl)methyl and 2-propenyl trans-7-oxo-1,6-diazabicyclo[3,2,1]octane-2,6-dicarboxylate 1.24 g (3.278 mmoles) of the product prepared in stage C of Example 29a is dissolved under a nitrogen atmosphere in 8 ml of dichloromethane.

The solution is cooled down to 0° C., then 0.45 ml of TEA then 0.35 ml of allyl chloroformate are added dropwise.

The reaction medium is maintained at 0° C. for 15 minutes, then left to react under agitation for 1 hour at ambient temperature.

The reaction medium is then diluted with 20 ml dichloromethane, washed with an aqueous solution of sodium bicarbonate, and twice with water.

The reaction medium is dried over magnesium sulphate, and the solvent is evaporated off under reduced pressure.

1.5 g of 1-(1,1-dimethylethyl) and 2-[(4-nitrophenyl)methyl]trans-5-[[(2-propenyloxy) carbonyl] amino]-1,2-piperidinedicarboxylate, with molecular formula C$_{22}$H$_{28}$N$_3$O$_8$, (M=462.486 g) is thus obtained The corresponding yield is 99%.

This product is used in stages similar to stages E to G of Example 29a and 30.6 mg of expected compound, with molecular formula C$_{18}$H$_{19}$N$_3$O$_7$, (M=389.368 g) is thus obtained in the form of a white solid. The corresponding yield is 40%.

NMR Spectrum of the Proton

In CDCl$_3$, at 300 MHz, chemical shifts of the peaks in ppm and multiplicity:

1.91 (m), 2.00 to 2.29 (m): N—CH—CH$_2$—CH$_2$; 2.98 (d) and 3.25 (bd): O=C—N—CH$_2$; 4.27 (t) O=C—N—CH; 4.37 (bs) O=C—N—CH$_2$—CH; 4.77 (bd): COO—CH$_2$—CH=; 5.33 (s): COO—CH$_2$—C$_6$H$_4$; 5.29 to 5.46: CH$_2$=CH; 5.98 (m): CH$_2$=CH; 7.96 and 8.29 [AA'BB']: C$_6$H$_4$—NO$_2$.

IR (CHCl$_3$): 1801, 1775, 1738, 1724; 1649; 1608, 1595, 1526 cm$^{-1}$.

MS (positive electrospray) m/z: [2M+Na]$^+$=801, [M+Na+CH$_3$CN]$^+$=453, [M+Na]$^+$=412

Example 31a phenylmethyl trans-6-benzoyl-7-oxo-1,6-diazabicyclo[3,2,1]octane-2-carboxylate 200 mg of phenylmethyl trans-5-(benzoylamino)-1-(chlorocarbonyl)-2-piperidinecarboxylate, with molecular formula C$_{21}$H$_{21}$ClN$_2$O$_4$ (M=400.87 g), prepared in a similar manner to stages A to F of Example 29a and 6 ml of anhydrous tetrahydrofuran are mixed together under an inert atmosphere and cooled down to −78° C.

0.55 ml of a 1M solution of lithium bis (trimethylsilyl) amide in tetrahydrofuran is added dropwise.

The reaction medium is left to react under agitation at −78° C. for 10 minutes then 25 µl of acetic acid is added.

The temperature is left to rise to ambient temperature, then the reaction medium is poured into 10 ml of a 10% aqueous solution of tartaric acid. Extraction is carried out with ethyl acetate, followed by washing with an aqueous phosphate buffer solution at pH=7, then with water and drying over magnesium sulphate.

The reaction medium is brought to dryness by evaporation of the solvent under reduced pressure.

158 mg of a crude product is thus obtained which is purified by chromatography on silica, eluting with a dichloromethane/acetone mixture 98/2.

70 mg of the expected compound, with molecular formula C$_{21}$H$_{20}$N$_2$O$_4$ (M=364.40 g) is thus recovered. The corresponding yield is 39%.

NMR Spectrum of the Proton

In CDCl$_3$, at 400 MHz, chemical shifts of the peaks in ppm and multiplicity:

2.15 (m) and 2.25 (m): NCH—CH$_2$—CH$_2$—CH—CO$_2$; 1.94 (m) and 2.36 (m): NCH—CH$_2$—CH$_2$—CH—CO$_2$; 4.20 (d) N—CH—CO$_2$; 4.50 (q): NCH—CH$_2$—CH$_2$—CH—CO$_2$; 3.08 (d) and 3.40 (dt): N—CH$_2$; 5.25 [AB]: CO$_2$—CH$_2$—C$_6$H$_5$; 7.38 (bs): CH$_2$—C$_6$H$_5$; 7.43 (bt) and 7.55 (bt) and 7.69 (bd) C$_6$H$_5$—CO.

IR (CHCl$_3$): 1764, 1744, 1675; 1602, 1584, 1498 cm$^1$.

MS (SIMS) m/z: [M+Na]$^+$=387, [M+H]$^+$=365, 259, 257, 229, 105, 91.

Example 31b phenylmethyl 6-benzoyl-7-oxo-1,6-diazabicyclo[3,2,1]oct-2-ene-2-carboxylate 46 mg (0.126 mmoles) of the product obtained in Example 31a and 0.5 ml of anhydrous tetrahydrofuran are mixed together.

The reaction medium is cooled down to −70° C. and 0.31 ml of 1M lithium bis (trimethylsilyl) amide in tetrahydrofuran is added.

The reaction medium is left to react for 2 hours at −70° C., then the temperature is allowed to rise to −15° C. and 0.41 ml of a solution of C$_6$H$_5$—SeCl at 0.7 mol/l in THF is added at this temperature.

The reaction medium is left under agitation at −15° C. for 15 minutes, then allowed to return to ambient temperature for 15 minutes and poured into a mixture of water and ice containing a few drops of a saturated aqueous solution of sodium bicarbonate.

The reaction medium is extracted with ethyl acetate, washed with water, dried and the solvent is evaporated off under reduced pressure.

The residue is purified by chromatography on silica eluting with a dichloromethane/acetone mixture 98/2 and 15 mg of phenylmethyl 6-benzoyl-7-oxo-2-(phenylselenyl)-1,6-diazabicyclo[3,2,1]octane-2-carboxylate, with molecular formula C$_{27}$H$_{24}$N$_2$O$_4$Se (M=519, 46 g) is thus recovered. The corresponding yield is 23%.

15 mg (0.029 mmole) of the compound obtained previously and 0.3 ml of dichloromethane are mixed together.

The reaction medium is cooled down to 0° C. and 15 mg of meta-chloroperbenzoic acid in solution in 0.15 ml of dichloromethane is added.

The reaction medium is left under agitation at 0° C. for 15 minutes, then left to return to ambient temperature.

The reaction medium is poured into approximately 20 ml of water, extracted with dichloromethane and the organic phase is washed with an aqueous solution of phosphate buffer at pH=7. Followed by drying over magnesium sulphate, filtering and the solvent is evaporated off under reduced pressure.

In this way 15 mg of crude product is obtained which is purified on silica eluting with a dichloromethane/acetone mixture 98/2.

In this way 5 mg of the expected compound, with molecular formula $C_{21}H_{18}N_2O_4$ (M=362.39 g) is recovered. The corresponding yield is 48%.

NMR Spectrum of the Proton

In $CDCl_3$, at 300 MHz, chemical shifts of the peaks in ppm and multiplicity: 2.66 (td) and 2.99 (tdd): N—CH—CH$_2$; 3.03 (d) and 3.77 (ddd): N—CH$_2$; 4.76 (tt): N—CH; 5.23 [AB]: CO2—CH$_2$—C$_6$H$_5$; 7.02 (dt) N—C=CH; 7.30 to 7.38 (m) CH$_2$—C$_6$H$_5$; 7.42 (tm), 7.54 (tm) and 7.62 (dm); C$_6$H$_5$—CO;

Example 31c 6-benzoyl-7-oxo-1,6-diazabicyclo[3,2,1]oct-2-ene-2-carboxylic acid 20 mg (0.055 mmole) of the product obtained in Example 31b is mixed, 0.4 ml of acetone and 4 mg of 10% Pd/C catalyst are added.

The reaction medium is placed under a hydrogen atmosphere and left to react for 3 hours under vigorous agitation.

The catalyst is filtered out and washed with acetone then with methanol. The filtrate is evaporated off under reduced pressure.

In this way 14 mg of expected compound, with molecular formula $C_{14}H_{12}N_2O_4$ (M=272.4 g) is obtained. The corresponding yield is 93%.
MS (EI) m/z: [M]$^+$: 272, 105.

Example 32a 2-propenyl trans-7-oxo-6-(2-phenylmethoxy)-1,6-diaza-bicyclo[3,2,1] octane-2-carboxylate Stage A
2-propenyl cis-5-hydroxy-1-[(trifluoroacetyl)-2-piperidine carboxylate 17 g (0.059 mole) of 1-(1,1-dimethylethyl) and 2-(2-propenyl) cis-5-hydroxy-1,2-piperidinedicarboxylate (described in Rec. Trav. Chim. (1959), 78, 648-658), with molecular formula $C_{14}H_{23}NO_5$ (M=285.3431 g) is dissolved in 17 ml of ethyl acetate.

A solution of 51 ml of hydrogen chloride in ethyl acetate at 150 g/l is added at 0° C.

The reaction medium is left to return to ambient temperature and left to react under agitation for 1 hour and 30 minutes.

The ethyl acetate is evaporated off under reduced pressure, followed by taking up in ethyl ether, which is eliminated in turn under reduced pressure.

In this way 12 g of a pale yellow solid is obtained which is mixed with 200 ml of tetrahydrofuran. The reaction medium is cooled down to 0° C., then 37.6 ml of TEA is added.

The temperature is maintained at 0° C., then 16.8 ml of trifluoroacetic anhydride is slowly added.

The temperature is allowed to rise to 20° C. and the reaction medium is left to react for another 20 minutes under agitation.

20 ml of water is then added.

The solution obtained is agitated for 1 hour at ambient temperature and poured into 300 ml of water. The solution is extracted with ethyl acetate, washed with water, dried over sodium sulphate, and the solvent is evaporated off under reduced pressure.

15.7 g of crude product is obtained which is purified by chromatography on silica eluting with a dichloromethane/ethyl acetate mixture 90/10.

12.3 g of expected compound, with molecular formula $C_{11}H_{14}F_3NO_4$ (M=281.23 g), is thus obtained in the form of a yellow oil. The corresponding yield is 73%.

Stage B
2-propenyl trans-5-[(phenylmethoxy)amino]-1-(trifluoroacetyl)-2-piperidinecarboxylate 10.9 g (38.7 mmoles) of the compound obtained in stage A, and 150 ml of acetonitrile are mixed together.

The pale yellow solution obtained is cooled down to −30° C., then 4.94 ml of 2.6-lutidine and 6.7 ml of trifluoromethanesulphonic anhydride are added. The reaction medium is agitated for 15 minutes then, still at −30° C., 9.57 g of O-benzylhydroxylamine is added.

At the end of the addition, the temperature is left to rise to 0° C. and the reaction medium is left to react for 1 hour at this temperature. 4.9 ml of 2,6-lutidine is then added and left in contact for 3 days at 0° C.

The reaction mixture is then poured into 500 ml of water and extracted with ethyl acetate. The reaction medium is washed successively with water, with an aqueous solution of phosphate buffer at pH=7.0, with a saturated aqueous solution of sodium chloride, then again with water.

Drying is carried out over sodium sulphate and the solvent is evaporated off under reduced pressure.

23 g of crude product is thus obtained which is dissolved in 150 ml of dichloromethane, followed by washing with a 10% aqueous solution of tartaric acid, then drying over sodium sulphate and the solvent is evaporated off under reduced pressure.

16.1 g of a yellow oil is thus recovered which is purified by chromatography on silica.

12.1 g of expected compound, with molecular formula $C_{18}H_{21}F_3N_2O_4$ (M=386.37 g) is recovered in crystallized form. The corresponding yield is 72%.

Stage C
2-propenyl trans-5-[(phenylmethoxy)amino]-2-piperidine carboxylate 80 ml of methanol is cooled down to −10° C., then 4.15 g (37.8 mmoles) of $NaBH_4$ is added.

A solution of 10.6 g (27.4 mmoles) of the compound obtained previously in 80 ml of methanol is slowly added, under agitation, to this mixture for a duration of 30 minutes, whilst maintaining the temperature at −10° C.

The temperature is then left to rise to 0° C., then this temperature is maintained for 3 hours.

The reaction mixture is poured into 450 ml of ice and water and 150 ml of ethyl acetate, followed by decanting, washing with water then the organic phase is dried over sodium sulphate and then the solvent is evaporated off under reduced pressure.

8.2 g of a yellow oil is thus obtained which is dissolved in 80 ml of tetrahydrofuran, a solution of 2.43 g of oxalic acid in 25 ml of THF is added. The oxalate which crystallizes is filtered out and washed with a little THF then dried under reduced pressure and dissolved in a saturated solution of sodium bicarbonate. Extraction is carried out with ethyl acetate, the organic phase is washed with water, dried over sodium sulphate and the solvent is evaporated off under reduced pressure.

4.39 g of expected compound, with molecular formula $C_{16}H_{22}N_2O_3$ (M=290.36 g) is thus obtained, in the form of an oil which crystallizes when the temperature is below 20 C.°. The corresponding yield is 55%.

Stage D 2-propenyl trans-7-oxo-6-(2-phenylmethoxy)-1,6-diazabicyclo[3,2,1]-octane-2-carboxylate 3.2 g (11 mmoles) of the oil obtained previously is dissolved under a nitrogen atmosphere in 500 ml of acetonitrile.

The solution obtained is cooled down to 0° C. using an ice bath and 3.37 ml of TEA, then 0.796 ml of diphosgene, and 1.48 g of DMAP are added.

The temperature is left to rise to 20° C. and the medium is left to react for 2 hours under agitation.

The reaction mixture is then poured into 200 ml of a 0.1N aqueous solution of hydrochloric acid, 400 ml of water is added, followed by extracting with dichloromethane, washing with water and drying over sodium sulphate.

The solvent is then evaporated off under reduced pressure in order to obtain 3.1 g of expected compound, with molecular formula $C_{17}H_{20}N_2O_4$ (M=316.36 g), in the form of crystals. The corresponding yield is 89%.

NMR Spectrum of the Proton 1.66 (m) and 2.00 to 2.16 (m) O=C—C$\underline{H}$—C$\underline{H}_2$—C$\underline{H}_2$; 2.94 (d) and 3.07 (dt) N—C$\underline{H}_2$; 3.31 (m) N—C$\overline{\underline{H_2—CH}}$; $\overline{4.14}$ (dd) O=C—C$\underline{H}$, 4.68 (dt) $\overline{C\underline{H}_2}$—CH=CH$_2$; 4.90 and 5.06 [AB] C$\underline{H}_2$—C$_6\underline{H}_5$; 5.26 (dq) $\overline{and}$ 5.34 (dq) CH$_2$—CH=C$\underline{H}_2$; 5.92 (m$\overline{)}$ $\overline{C\underline{H}_2}$—C$\underline{H}$=CH$_2$; 7.37 to 7.42 (m) C$_6\underline{H}_5$.

IR (CHCl$_3$): 1$\overline{7}$48; 1646; 1496 cm$^{-1}$.

MS (positive electrospray) m/z: [2M+Na]$^+$=655, [M+Na+CH$_3$CN]$^+$=380, [M+Na]$^+$=339, [M+H]$^+$=317, 289, 91.

Example 32b trans-7-oxo-6-(phenylmethoxy)-1,6-diazabicyclo [3,2,1] octane-2-carboxylic acid and its cyclohexylamine salt 2.21 g (6.98 mmoles) of the compound obtained in Example 32a is dissolved under a nitrogen atmosphere, in 44 ml of dichloromethane.

A 0.5 M solution of sodium ethyl-hexanoate in ethyl acetate is added.

Then 242 mg of tetrakistriphenylphosphine palladium is added in one go, then the medium is maintained under agitation for 1 hour, followed by diluting with 22 ml of ethyl acetate and pouring into 75 ml of a saturated solution of NaH$_2$PO$_4$.

Extraction is then carried out with ethyl acetate and the organic phase is dried over sodium sulphate. The solvent is evaporated off under reduced pressure in order to obtain 3.5 g of a yellow residue which is dissolved in a mixture of 11 ml of ethyl acetate and 0.8 ml of cyclohexylamine.

The crystallized cyclohexylamine salt is separated by filtration and washed with ethyl ether, then the solvent is evaporated off under reduced pressure. In this way a total of 2.51 g of crystallized salt is obtained which is dissolved in 25 ml of a saturated aqueous solution of NaH$_2$PO$_4$. After extracting with ethyl acetate, the organic phases are combined and dried over sodium sulphate, then the solvent is evaporated off under reduced pressure.

1.82 g of expected compound with molecular formula $C_{14}H_{16}N_2O_4$ (M=276.29 g) is thus recovered, in crystallized form. The corresponding yield is 94%.

NMR Spectrum of the Proton

In CDCl$_3$, at 300 MHz, chemical shifts of the peaks in ppm and multiplicity:

1.68 (m) and of 2.20 to 2.22 (m): CH—C$\underline{H}_2$—C$\underline{H}_2$—CH; 2.89 (d) and 3.11 (ddd): N—C$\underline{H}_2$; 3.34 (dd)$\overline{N—C\underline{H}_2}$—CH, 4.13 (bd): N—C$\underline{H}$—C=O; 4.$\overline{90}$ and 5.05 [AB]: C$\underline{H}_2$—O; 7.32 to 7.43: C$_6\underline{H}_5$.

MS (SIMS) $\overline{m/z}$: [M+Na]$^+$=299, [M+H]$^+$=277.91.

Example 33a

Pyridinium salt of trans-7-oxo-6-(sulphooxy)-1,6-diazabicyclo [3,2,1] octane-2-carboxamide Stage A trans-7-oxo-6-(phenylmethoxy)-1,6-diazabicyclo [3,2,1] octane-2-carboxamide 1.1 g (4 mmole) of the compound obtained in Example 32b is dissolved in 30 ml of dichloromethane.

0.67 ml of TEA is added to this solution.

The solution is cooled down to 5° C. and 0.57 ml of isobutyl chloroformate is added quite rapidly.

Agitation is maintained for 20 minutes at SOC, then 3 ml of concentrated ammonia is added, slowly, under vigorous agitation.

Agitation is maintained for one hour at ambient temperature, the reaction medium is diluted with 30 ml of water, followed by extracting with dichloromethane, washing with water, drying over sodium sulphate and concentrating under reduced pressure.

In this way 1.1 g of expected product with molecular formula $C_{14}H_{17}N_3O_3$ (M=275.31 g) is obtained.

The yield is quantitative.

Stage B trans-6-hydroxy-7-oxo-1,6-diazabicyclo[3,2,1]octane-2-carboxamide 1.1 g of the compound obtained in stage A, 30 ml of methanol and 300 mg of 10% Pd/C are mixed together.

The reaction medium is placed under a hydrogen atmosphere then the mixture is agitated vigorously for 45 minutes.

The catalyst is then filtered out, washed with methanol then with a dichloromethane/methanol mixture.

The filtrate is evaporated under reduced pressure.

800 mg of expected product with molecular formula $C_7H_{11}N_3O_3$ (M=185.18 g) is thus obtained, in the form of a colourless foam.

Stage C

Pyridinium salt of trans-7-oxo-6-(sulphooxy)-1,6-diazabicyclo [3,2,1] octane-2-carboxamide 800 mg of the compound obtained previously and 20 ml of anhydrous pyridine are mixed together under a nitrogen atmosphere.

Then 1.91 g of SO$_3$-pyridine complex is added.

The mixture is agitated for 20 hours at ambient temperature.

The reaction medium is then filtered and the solvent evaporated off under reduced pressure.

The expected product with molecular formula $C_{12}H_{16}N_4O_6S$, $C_5H_5N$ (M=344.35 g) is thus obtained in the form of a yellow product.

Example 33b

Tetrabutylammonium salt of trans-7-oxo-6-(sulphooxy)-1,6-diazabicyclo [3,2,1] octane-2-carboxamide The product obtained previously is introduced into 40 ml of a concentrated aqueous solution of $NaH_2PO_4$ so as to obtain a pH of 4.

Extraction is carried out with ethyl acetate then 1.01 g of tetrabutyl ammonium hydrogen sulphate is added to the aqueous phase.

Agitation is carried out for 10 minutes at ambient temperature, followed by extracting 4 times with 300 ml of ethyl acetate, drying the organic phase over sodium sulphate and concentrating under reduced pressure.

1.530 g of a colourless foam is thus obtained which is purified by chromatography on silica, eluting with an acetone/dichloromethane/TEA solvent 50/48/2.

In this way 1.02 g of expected product with molecular formula $C_{23}H_{46}N_4O_6S$ (M=506.71 g) is recovered, in the form of a colourless foam. The corresponding overall yield is 50%.

Example 33c

Sodium salt of trans-7-oxo-6-(sulphooxy)-1,6-diazabicyclo [3,2,1] octane-2-carboxamide The product obtained in Example 33b is dissolved in 7 ml of an acetone/water mixture 1/1 then deposited on a column of 180 g of DOWEX 50WX8 resin in $Na^+$ form and eluted with water. After evaporation of the water under reduced pressure, the product crystallizes.

542 mg of expected compound, of formula $C_7H_{10}N_3NaO_6S$ (M=287.23 g) is thus obtained. The corresponding yield is 94%.

NMR Spectrum of the Proton

In DMSO, at 300 MHz, chemical shifts of the peaks in ppm and multiplicity:

1.55 to 2.10 (3H): CH—$CH_2$—$CH_2$—CH; 2.91 (d) and 3.02 (bd): N—$CH_2$; 3.38 (bs): N—$CH_2$—CH; 3.68 (d): N—CH—C=O; 7.23 and 7.44: $NH_2$.

MS (negative electrospray) m/z: [M]⁻=264

Examples 34 to 47

The following carboxamides were prepared following an operating method similar to that which is used in Example 33 starting from 110 mg of the acid obtained in Example 32b.

The only difference is that in Stage 1, the reagent used, i.e. the ammonia solution, is replaced by a solution of the corresponding amine.

Thus, only the R1 group as defined in formula I varies.

Example 34

Starting from 49 µl of benzylamine, 64 mg of the sodium salt of trans-7-oxo-N-(phenylmethyl)-6-(sulphooxy)-1,6-diazabicyclo[3,2,1]octane-2-carboxamide is obtained i.e. an overall yield of 38%.

MS (positive electrospray) m/z: [M+Na]⁺=400, [M+H]⁺=378

Example 35

Starting from 43 µl of 2-pyridinemethanamine, 37 mg of the sodium salt of trans-7-oxo-N-(2-pyridinylmethyl)-6-(sulphooxy)-1,6-diazabicyclo[3,2,1]octane-2-carboxamide is obtained i.e. an overall yield of 14%.

MS (positive electrospray) m/z: [M+H]⁺=379

Example 36

Starting from 51.3 mg of 3-pyridineethanamine, 42 mg of the sodium salt of trans-7-oxo-N-[2-(3-pyridinyl)ethyl]-6-(sulphooxy)-1,6-diazabicyclo[3,2,1]octane-2-carboxamide is obtained i.e. an overall yield of 20%.

MS (positive electrospray) m/z: [M+H]⁺=393

Example 37

Starting from 51.3 mg of 4-pyridineethanamine, 40 mg of the sodium salt of trans-7-oxo-N-[2-(4-pyridinyl)ethyl]-6-(sulphooxy)-1,6-diazabicyclo[3,2,1]octane-2-carboxamide is obtained i.e. a yield of 20%.

MS (positive electrospray) m/z: [M+Na]⁺=415, [M+H]⁺=393

Example 38

Starting from 50.2 mg of 2-pyridineethanamine, 45 mg of the sodium salt of trans-7-oxo-N-[2-(2-pyridinyl)ethyl]-6-(sulphooxy)-1,6-diazabicyclo[3,2,1]octane-2-carboxamide is obtained i.e. a yield of 23%.

MS (positive electrospray) m/z: [M+H]⁺=393

Example 39

Starting from 58.3 mg of 3-amino-benzamide, 43 mg of the sodium salt of trans-N-[3-(aminocarbonyl)phenyl]-7-oxo-6-(sulphooxy)-1,6-diazabicyclo[3,2,1]octane-2-carboxamide is obtained i.e. a yield of 22%.

MS (negative electrospray) m/z: [M]⁻=383

Example 40

Starting from 58.3 mg of 4-dimethylamino-benzenamine, 65.3 mg the sodium salt of trans-N-[4-(dimethylamino)phenyl]-7-oxo-6-(sulphooxy)-1,6-diazabicyclo[3,2,1]octane-2-carboxamide is obtained i.e. a yield of 40%

MS (negative electrospray) m/z: [M]⁻=383

Example 41

Starting from 58.3 mg of 3-dimethylamino-benzenamine, 91 mg of the sodium salt of trans-N-[3-(dimethylamino)phenyl]-7-oxo-6-(sulphooxy)-1,6-diazabicyclo[3,2,1]octane-2-carboxamide is obtained i.e. a yield of 54%.

MS (negative electrospray) m/z: [M]⁻=383

Example 42

Starting from 43 µl of 4-pyridinemethanamine, 24.6 mg of the sodium salt of trans-7-oxo-N-[(4-pyridinyl)methyl]-6-(sulphooxy)-1,6-diazabicyclo[3,2,1]octane-2-carboxamide is obtained i.e. a yield of 15%.

MS (negative electrospray) m/z: [M]⁻=355

Example 43

Starting from 44 µl of 3-pyridinemethanamine, 44.7 mg of the sodium salt of trans-7-oxo-N-(3-pyridinylmethyl)-6-(sulphooxy)-1,6-diazabicyclo[3,2,1]octane-2-carboxamide is obtained i.e. a yield of 26%.

MS (negative electrospray) m/z: [M]⁻=355

Example 44

Starting from 84 mg (.+-.)-.alpha.-amino-benzene propanamide, 55 mg of the sodium salt of trans-N-(1-amino-1-oxo-3-phenyl-2-propyl)-7-oxo-6-(sulphooxy)-1,6-diazabicyclo[3,2,1]octane-2-carboxamide is obtained i.e. a yield of 27%.

MS (negative electrospray) m/z: [M]⁻=411, 321

Example 45

Starting from 46 mg of 2-amino-acetamide hydrochloride and 61 μl of TEA, 25 mg of the sodium salt of trans-N-(2-amino-2-oxoethyl)-7-oxo-6-(sulphooxy)-1,6-diazabicyclo[3,2,1]octane-2-carboxamide is obtained i.e. a yield of 13%.

MS (negative electrospray) m/z: [M]⁻=321, 249

Example 46

Starting from 64 mg of (3-aminophenyl)-urea, 43 mg of the sodium salt of trans-N-[3-[(aminocarbonyl)amino]phenyl ]-7-oxo-6-(sulphooxy)-1,6-diazabicyclo[3,2,1]octane-2-carboxamide is obtained i.e. a yield of 24%.

MS (negative electrospray) m/z: [M]⁻=398, 153, 111

Example 47

Starting from 63 mg of (.+-.)-.alpha.-amino-benzeneacetamide, 64 mg of the sodium salt of trans-N-(2-amino-2-oxo-1-phenylethyl)-7-oxo-6-(sulphooxy)-1,6-diazabicyclo[3,2,1] octane-2-carboxamide is obtained i.e. a yield of 38%

MS (negative electrospray) m/z: [M]⁻=397

Examples 48 to 51

The following compounds were prepared starting from 110 mg of compound obtained in stage E of Example 32, which is esterified each time with the appropriate alcohol in order to produce the final product.

Then, the operation is carried out in a similar manner to that described in stages B to E of Example 33.

Example 48

Starting from 31.5 mg of 2-hydroxy-acetamide, 54 mg of the sodium salt of 2-amino-2-oxoethyl trans-7-oxo-6-(sulphooxy)-1,6-diazabicyclo [3,2,1] octane-2-carboxylate is obtained i.e. a yield of 32%.

MS (negative electrospray) m/z: [M]⁻=322

Example 49

Starting from 51.7 mg of 4-pyridineethanol, 20 mg of the sodium salt of 2-(4-pyridinyl)ethyl trans-7-oxo-6-(sulphooxy)-1,6-diazabicyclo [3,2,1] octane-2-carboxylate is obtained i.e. a yield of 8.5%.

MS (negative electrospray) m/z: [M]⁻=370

Example 50

Starting from 47.3 mg of 2-pyridineethanol, 47 mg of the sodium salt of 2-(2-pyridinyl)ethyl trans-7-oxo-6-(sulphooxy)-1,6-diazabicyclo [3,2,1]octane-2-carboxylate is obtained i.e. a yield of 23.4%.

MS (negative electrospray) m/z: [M]⁻=370

Example 51

Starting from 57.7 mg of 3-pyridineethanol 50 mg of the sodium salt of 2-(3-pyridinyl)ethyl trans-7-oxo-6-(sulphooxy)-1,6-diazabicyclo[3,2,1]octane-2-carboxylate is obtained i.e. a yield of 26%.

MS (negative electrospray) m/z: [M]⁻=370

Pharmacological Study of the Products of the Invention

In vitro activity, method of dilution in liquid medium

A series of tubes are prepared in which the same quantity of sterile nutritive medium is distributed. Increasing quantities of the product to be studied are distributed into each tube, then each tube is sown with a bacterial strain. After incubation for twenty-four hours in a heating chamber at 37° C., the growth inhibition is evaluated by transillumination, which allows the minimal inhibitory concentrations (M.I.C.) to be determined, expressed in μg/cml.

The tests were carried out with the following products of the invention:

Test A: Sodium salt of trans-N-(2-amino-2-oxoethyl)-7-oxo-6-(sulphooxy)-1,6-diazabicyclo[3,2,1]octane-2-carboxamide, the preparation of which is described in Example 45

Test B: Sodium salt of trans-7-oxo-6-(sulphooxy)-1,6-diazabicyclo[3,2,1]octane-2-carboxamide, the preparation of which is described in Example 33c Test C: Sodium salt of trans-7-oxo-N-(3-pyridinylmethyl)-6-(sulphooxy)-1,6-diazabicyclo[3,2,1]octane-2-carboxamide, the preparation of which is described in Example 43

Test D: Sodium salt of trans-7-oxo-N-[(4-pyridinyl)methyl]-6-(sulphooxy)-1,6-diazabicyclo[3,2,1]octane-2-carboxamide, the preparation of which is described in Example 42

Test E: Sodium salt of trans-7-oxo-N-(phenylmethyl)-6-(sulphooxy)-1,6-diazabicyclo[3,2,1]octane-2-carboxamide, the preparation of which is described in Example 34

Test F: Sodium salt of phenylmethyl trans-7-oxo-6-(sulphooxy)-1,6-diazabicyclo[3,2,1]octane-2-carboxylate, the preparation of which is described in Example 28b.

The results are set out in the following table:

| | | M.I.C. measured in μg/ml TEST No. | | | | | |
|---|---|---|---|---|---|---|---|
| Strains | Code | A | B | C | D | E | F |
| S. aureus SG511 | 011 HT3 | >160 | >160 | >80 | >80 | 5 | 160 |
| S. aureus Exp 54146 | 011UC4 | >160 | >160 | >80 | >80 | 5 | 160 |
| S. Pyogenes A561 | 02A1UC1 | 160 | >160 | >80 | >80 | 1.2 | * |
| E. coli | 250HT11 | 160 | 80 | 20 | 20 | >80 | * |
| E. coli DC2 (permeable) | 250HT6 | 80 | 40 | 20 | 20 | >80 | * |
| E. coli (hyperpermeable) | 250IP5 | 20 | 10 | 5 | 2.5 | 20 | * |

* not determined

The compounds according to the invention therefore show an anti-bacterial activity.

Example of Pharmaceutical Composition

A pharmaceutical composition for injection is prepared containing:

Compound of Example 33c-500 mg
Sterile aqueous excipient q.s.f. 5 cm³.

The invention claimed is:
1. A compound having a formula selected from the group consisting of:

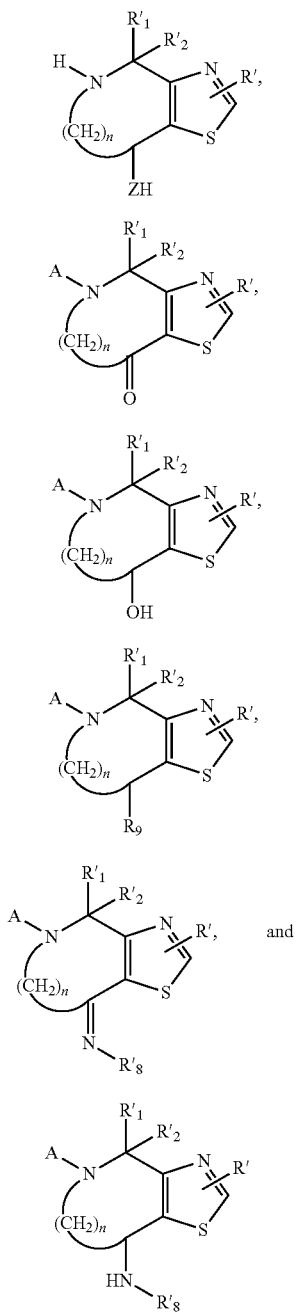

wherein
a) R'₁ is selected from the group consisting of hydrogen, —CN, protected —COOH, —COOR", —(CH₂)ₙ'—R'₅, —CONR₆R₇ and —C(=NR₆)NHR₇, R" is selected from the group consisting of alkyl of 1 to 6 carbon atoms, optionally substituted by pyridyl, —CH₂-alkenyl of 3 to 9 carbon atoms, aryl of 6 to 10 carbon atoms and aralkyl of 7 to 11 carbon atoms, the aryl and aralkyl optionally substituted on the aromatic ring by at least one member of the group consisting of —NO₂, protected OH, protected —NH₂, alkyl of 1 to 6 carbon atoms, alkoxy of 1 to 6 carbon atoms and halogen;

R'₅ is selected from the group consisting of protected —OH, —CN, protected —NH₂, —CO —NR₆R₇, protected —COOH, —COO'R", —OR", —OCOH, —OCOR", OCOOR", OCONH₂, OCONHR", protected NHR", NHCOR", NHSO₂R", —NHCOOR", —NH—CO—NHR" and —NH—CONH₂;

n' is 1 or 2,
R₆ and R₇ are individually selected from the group consisting of hydrogen, alkyl of 1 to 6 carbon atoms, optionally substituted by pyridyl, aryl of 6 to 10 carbon atoms and aralkyl of 7 to 11 carbon atoms;

R'₄ and R₃ together form heterocyclic aromatic of 5 to 6 vertices with 1 to 4 heteroatoms selected from the group consisting of oxygen, sulfur and nitrogen optionally substituted by at least one R';

R' is selected from the group consisting of hydrogen, alkyl of 1 to 6 carbon atoms optionally substituted by at least one oxo, halo, nitro, cyano, alkenyl of 2 to 6 carbon atoms, halogen, amino, —OH, protected —OH, —OR, —NHCOH, —NHCOR", —NHCOOR", —COOH, —COOR", —C(C₆H₅)₃ and —CH₂—CH₂—S(O)ₘ—R";

m is 0, 1 or 2;
R'₂ is selected from the group consisting of hydrogen, halogen, R", —S(O)ₘR", —OR", —NHCOH, —NHCOR", —NHCOOR" and —NHSO₂R";

m is 0, 1 or 2;
n is 1 or 2;
—ZH is selected from the group consisting of —(CH₂)ₙ"—OH, —NHR'₈—(CH₂)ₙ"— and —O—NHR₈;
n" is 0 or 1,
R'₈ is selected from the group consisting of hydrogen, R", protected —OH, —OR", —Y', —OY', —Y'₁, —OY'₁', —Y'₂, —OY'₂, —Y'₃, —OCH₂—CH₂—S(O)ₘ—R", —SiRₐR_bR_c and —OSiRₐR_bR_c; Rₐ, R_b and R_c are individually alkyl of 1 to 6 carbon atoms or aryl 6 to 10 carbon atoms;

m is defined above with the proviso that ZH is not —(CH₂)ₙ"—OH when R'₁ is —(CH₂)ₙ'—R'₅;

Y' is selected from the group consisting of —COH, —COR", —COOR", —CONH₂, —CONHR", —CONHSO₂R", —CH₂COOR", protected —CH₂tetrazol, —CH₂SO₂R", —CH₂PO(OR")₂, protected —CONHOH, protected CH₂COOH, protected CH₂CONHOH, protected CH₂SO₃H, protected —CH₂PO(OR), protected —CH₂PO(R)(OH) and protected —CH₂PO(OH)₂;

Y'₁ is selected from the group consisting of —SO₂R", —SO₂NHCOH, —SO₂NHCOR", —SO₂NHCOOR", —SO₂NHCONH₂, —SO₂NHCONHR" and protected —SO₃H;

Y'₂ is selected from the group consisting of —PO(OR")₂, protected —PO(OH)₂, protected —PO(OH)(OR) and protected —PO(OH)(R);

Y'₃ is selected from the group consisting of protected tetrazol, tetrazol substituted by R", protected squarate, protected —NH-tetrazole, protected —NR"-tetrazol, protected —NH—, —NR"-tetrazole substituted by R", —NHSO₂R" and —NSO₂R";

A is hydrogen or a nitrogen protective group,
and R9 is a leaving group and their acid addition salts.

2. A compound of the formula

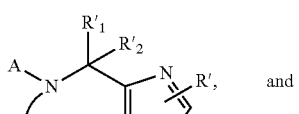
(VII)

and

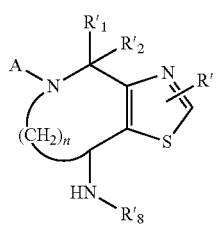
(VIII)

wherein $R'_1$, $R'_2$, $R'_4$, n, A and $R'_8$ have the definition of claim 1 and their acid addition salts.

3. A compound of the formula

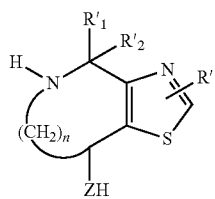
(II)

wherein —ZH, $R'_1$, $R'_2$, $R'_4$ and n have the definition of claim 1.

4. A compound of a formula selected from the group consisting of

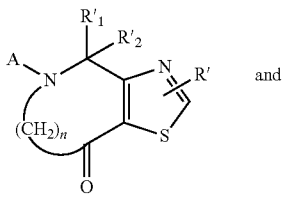
(IV)

and

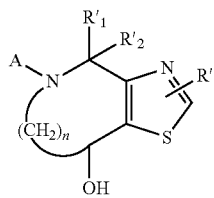
(V)

wherein $R'_1$, $R'_2$, $R'_4$, A and n are as defined in claim 1 and their acid addition salts.

* * * * *